(12) United States Patent
Witt et al.

(10) Patent No.: US 11,033,323 B2
(45) Date of Patent: Jun. 15, 2021

(54) SYSTEMS AND METHODS FOR MANAGING FLUID AND SUCTION IN ELECTROSURGICAL SYSTEMS

(71) Applicant: Ethicon LLC, Guaynabo, PR (US)

(72) Inventors: David A. Witt, Maineville, OH (US); David C. Yates, West Chester, OH (US); Frederick E. Shelton, IV, Hillsboro, OH (US); Cory G. Kimball, Hamilton, OH (US); Barry C. Worrell, Centerville, OH (US); Monica L. Rivard, Cincinnati, OH (US)

(73) Assignee: Cilag GmbH International, Zug (CH)

( * ) Notice: Subject to any disclaimer, the term of this patent is extended or adjusted under 35 U.S.C. 154(b) by 657 days.

(21) Appl. No.: 15/720,831

(22) Filed: Sep. 29, 2017

(65) Prior Publication Data

US 2019/0099213 A1     Apr. 4, 2019

(51) Int. Cl.
*A61B 18/14* (2006.01)
*A61B 18/00* (2006.01)
(Continued)

(52) U.S. Cl.
CPC .......... *A61B 18/14* (2013.01); *A61B 18/1402* (2013.01); *A61B 2018/00023* (2013.01);
(Continued)

(58) Field of Classification Search
CPC ................ A61B 18/14; A61B 18/1402; A61B 2018/00589; A61B 2018/00595;
(Continued)

(56) References Cited

U.S. PATENT DOCUMENTS

| 2,366,274 A | 1/1945 | Luth et al. |
| 2,458,152 A | 1/1949 | Eakins |

(Continued)

FOREIGN PATENT DOCUMENTS

| CN | 1634601 A | 7/2005 |
| CN | 1922563 A | 2/2007 |

(Continued)

OTHER PUBLICATIONS

Weir, C.E., "Rate of shrinkage of tendon collagen—heat, entropy and free energy of activation of the shrinkage of untreated tendon. Effect of acid salt, pickle, and tannage on the activation of tendon collagen." Journal of the American Leather Chemists Association, 44, pp. 108-140 (1949).

(Continued)

*Primary Examiner* — Thomas A Giuliani

(57) ABSTRACT

Aspects of the present disclosure include control systems of an electrosurgical system for managing the flow of fluid, such as saline, and rates of aspiration or suction, in response to various states of conditions at a surgical site. The control system(s) may monitor and adjust to impedance at the surgical site, temperature of the surgical tissue, and/or RF current of electrodes, and may account for certain undesirable conditions, such as the electrodes sticking. The control systems may include various automatic sensing scenarios, while also allowing for several manual conditions.

17 Claims, 26 Drawing Sheets

(51) Int. Cl.
  *A61B 18/12* (2006.01)
  *A61M 39/28* (2006.01)
  *A61B 18/04* (2006.01)

(52) U.S. Cl.
  CPC .............. *A61B 2018/00035* (2013.01); *A61B 2018/00196* (2013.01); *A61B 2018/00589* (2013.01); *A61B 2018/00595* (2013.01); *A61B 2018/00648* (2013.01); *A61B 2018/00678* (2013.01); *A61B 2018/00744* (2013.01); *A61B 2018/00779* (2013.01); *A61B 2018/00791* (2013.01); *A61B 2018/00827* (2013.01); *A61B 2018/00863* (2013.01); *A61B 2018/00875* (2013.01); *A61B 2018/00892* (2013.01); *A61B 2018/00922* (2013.01); *A61B 2018/00946* (2013.01); *A61B 2018/00952* (2013.01); *A61B 2018/048* (2013.01); *A61B 2018/126* (2013.01); *A61B 2018/1465* (2013.01); *A61B 2218/002* (2013.01); *A61B 2218/007* (2013.01); *A61M 39/283* (2013.01); *A61M 39/288* (2013.01)

(58) Field of Classification Search
  CPC ........... A61B 2018/00892; A61B 2018/00779; A61B 2018/00648; A61B 2018/00744; A61B 2018/122; A61B 2018/1472; A61B 2018/00791; A61B 2018/00875; A61B 2018/00583; A61B 2018/00011; A61B 2018/00029; A61B 2018/00023; A61B 2018/00035; A61B 2018/00827; A61B 2018/046; A61B 2018/126; A61B 2218/002; A61B 2218/007; A61B 2018/00625; A61B 2018/1213; A61B 2018/1467; A61B 2018/147; A61B 2217/007
  USPC ........ 606/32, 34, 38, 40–42, 49; 607/98, 99, 607/101, 102, 104, 105, 113, 115, 116
  See application file for complete search history.

(56) References Cited

U.S. PATENT DOCUMENTS

| | | | |
|---|---|---|---|
| 2,510,693 A | 6/1950 | Green |
| 2,736,960 A | 3/1956 | Armstrong |
| 2,849,788 A | 9/1958 | Creek |
| 2,867,039 A | 1/1959 | Zach |
| 3,015,961 A | 1/1962 | Roney |
| 3,043,309 A | 7/1962 | McCarthy |
| 3,166,971 A | 1/1965 | Stoecker |
| 3,358,676 A | 12/1967 | Frei et al. |
| 3,525,912 A | 8/1970 | Wallin |
| 3,526,219 A | 9/1970 | Balamuth |
| 3,580,841 A | 5/1971 | Cadotte et al. |
| 3,614,484 A | 10/1971 | Shoh |
| 3,636,943 A | 1/1972 | Balamuth |
| 3,703,651 A | 11/1972 | Blowers |
| 3,710,399 A | 1/1973 | Hurst |
| 3,776,238 A | 12/1973 | Peyman et al. |
| 3,777,760 A | 12/1973 | Essner |
| 3,805,787 A | 4/1974 | Banko |
| 3,862,630 A | 1/1975 | Balamuth |
| 3,900,823 A | 8/1975 | Sokal et al. |
| 3,906,217 A | 9/1975 | Lackore |
| 3,918,442 A | 11/1975 | Nikolaev et al. |
| 3,946,738 A | 3/1976 | Newton et al. |
| 3,955,859 A | 5/1976 | Stella et al. |
| 3,956,826 A | 5/1976 | Perdreaux, Jr. |
| 3,988,535 A | 10/1976 | Hickman et al. |
| 4,005,714 A | 2/1977 | Hiltebrandt |
| 4,034,762 A | 7/1977 | Cosens et al. |
| 4,047,136 A | 9/1977 | Satto |
| 4,058,126 A | 11/1977 | Leveen |
| 4,063,561 A | 12/1977 | McKenna |
| 4,099,192 A | 7/1978 | Aizawa et al. |
| 4,156,187 A | 5/1979 | Murry et al. |
| 4,188,927 A | 2/1980 | Harris |
| 4,200,106 A | 4/1980 | Douvas et al. |
| 4,203,430 A | 5/1980 | Takahashi |
| 4,220,154 A | 9/1980 | Semm |
| 4,237,441 A | 12/1980 | van Konynenburg et al. |
| 4,278,077 A | 7/1981 | Mizumoto |
| 4,281,785 A | 8/1981 | Brooks |
| 4,304,987 A | 12/1981 | van Konynenburg |
| 4,314,559 A | 2/1982 | Allen |
| 4,384,584 A | 5/1983 | Chen |
| 4,445,063 A | 4/1984 | Smith |
| 4,463,759 A | 8/1984 | Garito et al. |
| 4,491,132 A | 1/1985 | Aikins |
| 4,492,231 A | 1/1985 | Auth |
| 4,535,773 A | 8/1985 | Yoon |
| 4,545,926 A | 10/1985 | Fouts, Jr. et al. |
| 4,550,870 A | 11/1985 | Krumme et al. |
| 4,582,236 A | 4/1986 | Hirose |
| 4,585,282 A | 4/1986 | Bosley |
| 4,597,390 A | 7/1986 | Mulhollan et al. |
| 4,617,927 A | 10/1986 | Manes |
| 4,633,874 A | 1/1987 | Chow et al. |
| 4,634,420 A | 1/1987 | Spinosa et al. |
| 4,640,279 A | 2/1987 | Beard |
| 4,655,746 A | 4/1987 | Daniels et al. |
| 4,671,287 A | 6/1987 | Fiddian-Green |
| 4,708,127 A | 11/1987 | Abdelghani |
| 4,735,603 A | 4/1988 | Goodson et al. |
| 4,761,871 A | 8/1988 | O'Connor et al. |
| 4,777,951 A | 10/1988 | Cribier et al. |
| 4,797,803 A | 1/1989 | Carroll |
| 4,798,588 A | 1/1989 | Aillon |
| 4,802,461 A | 2/1989 | Cho |
| 4,803,506 A | 2/1989 | Diehl et al. |
| 4,830,462 A | 5/1989 | Karny et al. |
| 4,832,683 A | 5/1989 | Idemoto et al. |
| 4,838,853 A | 6/1989 | Parisi |
| 4,849,133 A | 7/1989 | Yoshida et al. |
| 4,850,354 A | 7/1989 | McGurk-Burleson et al. |
| 4,860,745 A | 8/1989 | Farin et al. |
| 4,865,159 A | 9/1989 | Jamison |
| 4,878,493 A | 11/1989 | Pasternak et al. |
| 4,880,015 A | 11/1989 | Nierman |
| 4,896,009 A | 1/1990 | Pawlowski |
| 4,910,389 A | 3/1990 | Sherman et al. |
| 4,910,633 A | 3/1990 | Quinn |
| 4,911,148 A | 3/1990 | Sosnowski et al. |
| 4,919,129 A | 4/1990 | Weber, Jr. et al. |
| 4,920,978 A | 5/1990 | Colvin |
| 4,922,902 A | 5/1990 | Wuchinich et al. |
| 4,936,842 A | 6/1990 | D'Amelio et al. |
| 4,961,738 A | 10/1990 | Mackin |
| 4,967,670 A | 11/1990 | Morishita et al. |
| 4,981,756 A | 1/1991 | Rhandhawa |
| 5,007,919 A | 4/1991 | Silva et al. |
| 5,019,075 A | 5/1991 | Spears et al. |
| 5,020,514 A | 6/1991 | Heckele |
| 5,026,387 A | 6/1991 | Thomas |
| 5,061,269 A | 10/1991 | Muller |
| 5,093,754 A | 3/1992 | Kawashima |
| 5,099,216 A | 3/1992 | Pelrine |
| 5,099,840 A | 3/1992 | Goble et al. |
| 5,104,025 A | 4/1992 | Main et al. |
| 5,106,538 A | 4/1992 | Barma et al. |
| 5,108,383 A | 4/1992 | White |
| 5,112,300 A | 5/1992 | Ureche |
| 5,123,903 A | 6/1992 | Quaid et al. |
| 5,150,102 A | 9/1992 | Takashima |
| 5,150,272 A | 9/1992 | Danley et al. |
| 5,156,633 A | 10/1992 | Smith |
| 5,160,334 A | 11/1992 | Billings et al. |
| 5,162,044 A | 11/1992 | Gahn et al. |
| 5,167,725 A | 12/1992 | Clark et al. |
| D332,660 S | 1/1993 | Rawson et al. |
| 5,176,695 A | 1/1993 | Dulebohn |

(56) References Cited

U.S. PATENT DOCUMENTS

| | | |
|---|---|---|
| 5,184,605 A | 2/1993 | Grzeszykowski |
| 5,188,102 A | 2/1993 | Idemoto et al. |
| 5,190,541 A | 3/1993 | Abele et al. |
| 5,196,007 A | 3/1993 | Ellman et al. |
| 5,205,459 A | 4/1993 | Brinkerhoff et al. |
| 5,205,817 A | 4/1993 | Idemoto et al. |
| 5,209,719 A | 5/1993 | Baruch et al. |
| 5,213,569 A | 5/1993 | Davis |
| 5,217,460 A | 6/1993 | Knoepfler |
| 5,221,282 A | 6/1993 | Wuchinich |
| 5,226,910 A | 7/1993 | Kajiyama et al. |
| 5,234,428 A | 8/1993 | Kaufman |
| 5,241,236 A | 8/1993 | Sasaki et al. |
| 5,253,647 A | 10/1993 | Takahashi et al. |
| 5,254,130 A | 10/1993 | Poncet et al. |
| 5,257,988 A | 11/1993 | L'Esperance, Jr. |
| 5,258,004 A | 11/1993 | Bales et al. |
| 5,258,006 A | 11/1993 | Rydell et al. |
| 5,261,922 A | 11/1993 | Hood |
| 5,263,957 A | 11/1993 | Davison |
| 5,267,091 A | 11/1993 | Chen |
| 5,282,800 A | 2/1994 | Foshee et al. |
| 5,285,945 A | 2/1994 | Brinkerhoff et al. |
| 5,290,286 A | 3/1994 | Parins |
| 5,293,863 A | 3/1994 | Zhu et al. |
| 5,304,115 A | 4/1994 | Pflueger et al. |
| D347,474 S | 5/1994 | Olson |
| 5,309,927 A | 5/1994 | Welch |
| 5,312,023 A | 5/1994 | Green et al. |
| 5,313,306 A | 5/1994 | Kuban et al. |
| 5,318,563 A | 6/1994 | Malis et al. |
| 5,318,564 A | 6/1994 | Eggers |
| 5,318,565 A | 6/1994 | Kuriloff et al. |
| 5,318,570 A | 6/1994 | Hood et al. |
| 5,318,589 A | 6/1994 | Lichtman |
| 5,322,055 A | 6/1994 | Davison et al. |
| 5,324,260 A | 6/1994 | O'Neill et al. |
| 5,324,299 A | 6/1994 | Davison et al. |
| 5,326,013 A | 7/1994 | Green et al. |
| 5,330,471 A | 7/1994 | Eggers |
| 5,330,502 A | 7/1994 | Hassler et al. |
| 5,333,624 A | 8/1994 | Tovey |
| 5,339,723 A | 8/1994 | Huitema |
| 5,342,359 A | 8/1994 | Rydell |
| 5,344,420 A | 9/1994 | Hilal et al. |
| 5,346,502 A | 9/1994 | Estabrook et al. |
| 5,352,219 A | 10/1994 | Reddy |
| 5,359,992 A | 11/1994 | Hori et al. |
| 5,361,583 A | 11/1994 | Huitema |
| 5,366,466 A | 11/1994 | Christian et al. |
| 5,370,640 A | 12/1994 | Kolff |
| D354,564 S | 1/1995 | Medema |
| 5,381,067 A | 1/1995 | Greenstein et al. |
| 5,383,874 A | 1/1995 | Jackson et al. |
| 5,387,207 A | 2/1995 | Dyer et al. |
| 5,389,098 A | 2/1995 | Tsuruta et al. |
| 5,395,033 A | 3/1995 | Byrne et al. |
| 5,395,312 A | 3/1995 | Desai |
| 5,395,331 A | 3/1995 | O'Neill et al. |
| 5,395,363 A | 3/1995 | Billings et al. |
| 5,395,364 A | 3/1995 | Anderhub et al. |
| 5,396,266 A | 3/1995 | Brimhall |
| 5,396,900 A | 3/1995 | Slater et al. |
| 5,403,312 A | 4/1995 | Yates et al. |
| 5,409,483 A | 4/1995 | Campbell et al. |
| D358,887 S | 5/1995 | Feinberg |
| 5,411,481 A | 5/1995 | Allen et al. |
| 5,413,575 A | 5/1995 | Haenggi |
| 5,417,709 A | 5/1995 | Slater |
| 5,419,761 A | 5/1995 | Narayanan et al. |
| 5,421,829 A | 6/1995 | Olichney et al. |
| 5,428,504 A | 6/1995 | Bhatla |
| 5,429,131 A | 7/1995 | Scheinman et al. |
| 5,431,640 A | 7/1995 | Gabriel |
| 5,443,463 A | 8/1995 | Stern et al. |
| 5,445,615 A | 8/1995 | Yoon |
| 5,445,638 A | 8/1995 | Rydell et al. |
| 5,449,370 A | 9/1995 | Vaitekunas |
| 5,451,227 A | 9/1995 | Michaelson |
| 5,456,684 A | 10/1995 | Schmidt et al. |
| 5,458,598 A | 10/1995 | Feinberg et al. |
| 5,462,604 A | 10/1995 | Shibano et al. |
| 5,465,895 A | 11/1995 | Knodel et al. |
| 5,472,443 A | 12/1995 | Cordis et al. |
| 5,476,479 A | 12/1995 | Green et al. |
| 5,477,788 A | 12/1995 | Morishita |
| 5,478,003 A | 12/1995 | Green et al. |
| 5,480,409 A | 1/1996 | Riza |
| 5,483,501 A | 1/1996 | Park et al. |
| 5,484,436 A | 1/1996 | Eggers et al. |
| 5,486,162 A | 1/1996 | Brumbach |
| 5,486,189 A | 1/1996 | Mudry et al. |
| 5,489,256 A | 2/1996 | Adair |
| 5,496,317 A | 3/1996 | Goble et al. |
| 5,500,216 A | 3/1996 | Julian et al. |
| 5,501,654 A | 3/1996 | Failla et al. |
| 5,504,650 A | 4/1996 | Katsui et al. |
| 5,505,693 A | 4/1996 | Mackool |
| 5,509,922 A | 4/1996 | Aranyi et al. |
| 5,511,556 A | 4/1996 | DeSantis |
| 5,520,704 A | 5/1996 | Castro et al. |
| 5,522,839 A | 6/1996 | Pilling |
| 5,531,744 A | 7/1996 | Nardella et al. |
| 5,540,648 A | 7/1996 | Yoon |
| 5,540,681 A | 7/1996 | Strul et al. |
| 5,542,916 A | 8/1996 | Hirsch et al. |
| 5,542,938 A | 8/1996 | Avellanet et al. |
| 5,558,671 A | 9/1996 | Yates |
| 5,562,609 A | 10/1996 | Brumbach |
| 5,562,610 A | 10/1996 | Brumbach |
| 5,562,657 A | 10/1996 | Griffin |
| 5,563,179 A | 10/1996 | Stone et al. |
| 5,569,164 A | 10/1996 | Lurz |
| 5,571,121 A | 11/1996 | Heifetz |
| 5,573,534 A | 11/1996 | Stone |
| 5,584,830 A | 12/1996 | Ladd et al. |
| 5,599,350 A | 2/1997 | Schulze et al. |
| 5,601,601 A | 2/1997 | Tal et al. |
| 5,604,531 A | 2/1997 | Iddan et al. |
| 5,607,436 A | 3/1997 | Pratt et al. |
| 5,607,450 A | 3/1997 | Zvenyatsky et al. |
| 5,611,813 A | 3/1997 | Lichtman |
| 5,618,307 A | 4/1997 | Donlon et al. |
| 5,618,492 A | 4/1997 | Auten et al. |
| 5,624,452 A | 4/1997 | Yates |
| 5,626,578 A | 5/1997 | Tihon |
| 5,628,760 A | 5/1997 | Knoepfler |
| 5,630,420 A | 5/1997 | Vaitekunas |
| 5,632,432 A | 5/1997 | Schulze et al. |
| D381,077 S | 7/1997 | Hunt |
| 5,643,175 A | 7/1997 | Adair |
| 5,645,065 A | 7/1997 | Shapiro et al. |
| 5,647,871 A | 7/1997 | Levine et al. |
| 5,651,780 A | 7/1997 | Jackson et al. |
| 5,653,677 A | 8/1997 | Okada et al. |
| 5,653,713 A | 8/1997 | Michelson |
| 5,657,697 A | 8/1997 | Murai |
| 5,658,281 A | 8/1997 | Heard |
| 5,662,667 A | 9/1997 | Knodel |
| 5,665,085 A | 9/1997 | Nardella |
| 5,665,100 A | 9/1997 | Yoon |
| 5,669,922 A | 9/1997 | Hood |
| 5,674,219 A | 10/1997 | Monson et al. |
| 5,674,220 A | 10/1997 | Fox et al. |
| 5,674,235 A | 10/1997 | Parisi |
| 5,681,260 A | 10/1997 | Ueda et al. |
| 5,688,270 A | 11/1997 | Yates et al. |
| 5,690,269 A | 11/1997 | Bolanos et al. |
| 5,693,051 A | 12/1997 | Schulze et al. |
| 5,694,936 A | 12/1997 | Fujimoto et al. |
| 5,700,243 A | 12/1997 | Narciso, Jr. |
| 5,700,261 A | 12/1997 | Brinkerhoff |
| 5,704,900 A | 1/1998 | Dobrovolny et al. |
| 5,709,680 A | 1/1998 | Yates et al. |

(56) References Cited

U.S. PATENT DOCUMENTS

| | | |
|---|---|---|
| 5,711,472 A | 1/1998 | Bryan |
| 5,713,896 A | 2/1998 | Nardella |
| 5,716,366 A | 2/1998 | Yates |
| 5,720,742 A | 2/1998 | Zacharias |
| 5,720,744 A | 2/1998 | Eggleston et al. |
| 5,722,326 A | 3/1998 | Post |
| 5,722,426 A | 3/1998 | Kolff |
| 5,732,636 A | 3/1998 | Wang et al. |
| 5,733,074 A | 3/1998 | Stock et al. |
| 5,735,848 A | 4/1998 | Yates et al. |
| 5,738,652 A | 4/1998 | Boyd et al. |
| 5,741,226 A | 4/1998 | Strukel et al. |
| 5,741,305 A | 4/1998 | Vincent et al. |
| 5,743,906 A | 4/1998 | Parins et al. |
| 5,752,973 A | 5/1998 | Kieturakis |
| 5,755,717 A | 5/1998 | Yates et al. |
| 5,762,255 A | 6/1998 | Chrisman et al. |
| 5,776,130 A | 7/1998 | Buysse et al. |
| 5,779,701 A | 7/1998 | McBrayer et al. |
| 5,782,834 A | 7/1998 | Lucey et al. |
| 5,792,135 A | 8/1998 | Madhani et al. |
| 5,792,138 A | 8/1998 | Shipp |
| 5,796,188 A | 8/1998 | Bays |
| 5,797,941 A | 8/1998 | Schulze et al. |
| 5,800,432 A | 9/1998 | Swanson |
| 5,800,449 A | 9/1998 | Wales |
| 5,805,140 A | 9/1998 | Rosenberg et al. |
| 5,807,393 A | 9/1998 | Williamson, IV et al. |
| 5,810,718 A | 9/1998 | Akiba et al. |
| 5,810,811 A | 9/1998 | Yates et al. |
| 5,810,859 A | 9/1998 | DiMatteo et al. |
| 5,817,033 A | 10/1998 | DeSantis et al. |
| 5,817,084 A | 10/1998 | Jensen |
| 5,817,093 A | 10/1998 | Williamson, IV et al. |
| 5,827,323 A | 10/1998 | Klieman et al. |
| 5,828,160 A | 10/1998 | Sugishita |
| 5,836,867 A | 11/1998 | Speier et al. |
| 5,836,909 A | 11/1998 | Cosmescu |
| 5,836,943 A | 11/1998 | Miller, III |
| 5,836,990 A | 11/1998 | Li |
| 5,843,109 A | 12/1998 | Mehta et al. |
| 5,853,412 A | 12/1998 | Mayenberger |
| 5,876,401 A | 3/1999 | Schulze et al. |
| 5,878,193 A | 3/1999 | Wang et al. |
| 5,879,364 A | 3/1999 | Bromfield et al. |
| 5,880,668 A | 3/1999 | Hall |
| 5,883,454 A | 3/1999 | Hones et al. |
| 5,887,018 A | 3/1999 | Bayazitoglu et al. |
| 5,891,142 A | 4/1999 | Eggers et al. |
| 5,893,835 A | 4/1999 | Witt et al. |
| 5,897,569 A | 4/1999 | Kellogg et al. |
| 5,902,239 A | 5/1999 | Buurman |
| 5,904,147 A | 5/1999 | Conlan et al. |
| 5,906,579 A | 5/1999 | Vander Salm et al. |
| 5,906,625 A | 5/1999 | Bito et al. |
| 5,910,129 A | 6/1999 | Koblish et al. |
| 5,921,956 A | 7/1999 | Grinberg et al. |
| 5,929,846 A | 7/1999 | Rosenberg et al. |
| 5,935,143 A | 8/1999 | Hood |
| 5,935,144 A | 8/1999 | Estabrook |
| 5,938,633 A | 8/1999 | Beaupre |
| 5,944,298 A | 8/1999 | Koike |
| 5,944,718 A | 8/1999 | Austin et al. |
| 5,944,737 A | 8/1999 | Tsonton et al. |
| 5,954,736 A | 9/1999 | Bishop et al. |
| 5,954,746 A | 9/1999 | Holthaus et al. |
| 5,957,849 A | 9/1999 | Munro |
| 5,957,882 A | 9/1999 | Nita et al. |
| 5,957,943 A | 9/1999 | Vaitekunas |
| 5,968,007 A | 10/1999 | Simon et al. |
| 5,968,060 A | 10/1999 | Kellogg |
| D416,089 S | 11/1999 | Barton et al. |
| 5,984,938 A | 11/1999 | Yoon |
| 5,989,182 A | 11/1999 | Hori et al. |
| 5,989,274 A | 11/1999 | Davison et al. |
| 5,989,275 A | 11/1999 | Estabrook et al. |
| 5,993,972 A | 11/1999 | Reich et al. |
| 6,003,517 A | 12/1999 | Sheffield et al. |
| 6,007,484 A | 12/1999 | Thompson |
| 6,013,052 A | 1/2000 | Durman et al. |
| 6,014,580 A | 1/2000 | Blume et al. |
| 6,024,741 A | 2/2000 | Williamson, IV et al. |
| 6,024,744 A | 2/2000 | Kese et al. |
| 6,033,375 A | 3/2000 | Brumbach |
| 6,033,399 A | 3/2000 | Gines |
| 6,039,734 A | 3/2000 | Goble |
| 6,050,996 A | 4/2000 | Schmaltz et al. |
| 6,053,172 A | 4/2000 | Hovda et al. |
| 6,063,098 A | 5/2000 | Houser et al. |
| 6,066,132 A | 5/2000 | Chen et al. |
| 6,068,629 A | 5/2000 | Haissaguerre et al. |
| 6,068,647 A | 5/2000 | Witt et al. |
| 6,074,389 A | 6/2000 | Levine et al. |
| 6,077,285 A | 6/2000 | Boukhny |
| 6,080,152 A | 6/2000 | Nardella et al. |
| 6,083,151 A | 7/2000 | Renner et al. |
| 6,083,191 A | 7/2000 | Rose |
| 6,086,584 A | 7/2000 | Miller |
| 6,090,120 A | 7/2000 | Wright et al. |
| 6,091,995 A | 7/2000 | Ingle et al. |
| 6,093,186 A | 7/2000 | Goble |
| 6,099,483 A | 8/2000 | Palmer et al. |
| 6,099,550 A | 8/2000 | Yoon |
| 6,109,500 A | 8/2000 | Alli et al. |
| 6,113,594 A | 9/2000 | Savage |
| 6,113,598 A | 9/2000 | Baker |
| 6,123,466 A | 9/2000 | Persson et al. |
| H1904 H | 10/2000 | Yates et al. |
| 6,127,757 A | 10/2000 | Swinbanks |
| 6,132,368 A | 10/2000 | Cooper |
| 6,139,320 A | 10/2000 | Hahn |
| 6,144,402 A | 11/2000 | Norsworthy et al. |
| 6,152,902 A | 11/2000 | Christian et al. |
| 6,152,923 A | 11/2000 | Ryan |
| 6,154,198 A | 11/2000 | Rosenberg |
| 6,159,160 A | 12/2000 | Hsei et al. |
| 6,159,175 A | 12/2000 | Strukel et al. |
| 6,162,208 A | 12/2000 | Hipps |
| 6,173,199 B1 | 1/2001 | Gabriel |
| 6,173,715 B1 | 1/2001 | Sinanan et al. |
| 6,174,309 B1 | 1/2001 | Wrublewski et al. |
| 6,176,857 B1 | 1/2001 | Ashley |
| 6,190,386 B1 | 2/2001 | Rydell |
| 6,193,709 B1 | 2/2001 | Miyawaki et al. |
| 6,206,844 B1 | 3/2001 | Reichel et al. |
| 6,206,876 B1 | 3/2001 | Levine et al. |
| 6,206,877 B1 | 3/2001 | Kese et al. |
| 6,210,403 B1 | 4/2001 | Klicek |
| 6,214,023 B1 | 4/2001 | Whipple et al. |
| 6,219,572 B1 | 4/2001 | Young |
| 6,221,007 B1 | 4/2001 | Green |
| 6,228,080 B1 | 5/2001 | Gines |
| 6,228,084 B1 | 5/2001 | Kirwan, Jr. |
| 6,231,565 B1 | 5/2001 | Tovey et al. |
| 6,233,476 B1 | 5/2001 | Strommer et al. |
| 6,238,366 B1 | 5/2001 | Savage et al. |
| 6,241,724 B1 | 6/2001 | Fleischman et al. |
| 6,248,074 B1 | 6/2001 | Ohno et al. |
| D444,365 S | 7/2001 | Bass et al. |
| 6,254,623 B1 | 7/2001 | Haibel, Jr. et al. |
| 6,258,034 B1 | 7/2001 | Hanafy |
| 6,258,086 B1 | 7/2001 | Ashley et al. |
| 6,259,230 B1 | 7/2001 | Chou |
| 6,267,761 B1 | 7/2001 | Ryan |
| 6,270,831 B2 | 8/2001 | Kumar et al. |
| 6,273,852 B1 | 8/2001 | Lehe et al. |
| 6,273,887 B1 | 8/2001 | Yamauchi et al. |
| 6,274,963 B1 | 8/2001 | Estabrook et al. |
| 6,277,115 B1 | 8/2001 | Saadat |
| 6,277,117 B1 | 8/2001 | Tetzlaff et al. |
| 6,278,218 B1 | 8/2001 | Madan et al. |
| 6,283,981 B1 | 9/2001 | Beaupre |
| 6,292,700 B1 | 9/2001 | Morrison et al. |
| 6,309,400 B2 | 10/2001 | Beaupre |

(56) References Cited

U.S. PATENT DOCUMENTS

| | | |
|---|---|---|
| 6,315,789 B1 | 11/2001 | Cragg |
| 6,319,221 B1 | 11/2001 | Savage et al. |
| 6,325,799 B1 | 12/2001 | Goble |
| 6,325,811 B1 | 12/2001 | Messerly |
| 6,328,751 B1 | 12/2001 | Beaupre |
| 6,340,878 B1 | 1/2002 | Oglesbee |
| 6,352,532 B1 | 3/2002 | Kramer et al. |
| 6,364,888 B1 | 4/2002 | Niemeyer et al. |
| 6,371,952 B1 | 4/2002 | Madhani et al. |
| 6,379,320 B1 | 4/2002 | Lafon et al. |
| 6,379,351 B1 | 4/2002 | Thapliyal et al. |
| D457,958 S | 5/2002 | Dycus et al. |
| 6,383,194 B1 | 5/2002 | Pothula |
| 6,387,094 B1 | 5/2002 | Eitenmuller |
| 6,387,109 B1 | 5/2002 | Davison et al. |
| 6,388,657 B1 | 5/2002 | Natoli |
| 6,391,026 B1 | 5/2002 | Hung et al. |
| 6,391,042 B1 | 5/2002 | Cimino |
| 6,398,779 B1 | 6/2002 | Buysse et al. |
| 6,409,722 B1 | 6/2002 | Hoey et al. |
| H2037 H | 7/2002 | Yates et al. |
| 6,416,469 B1 | 7/2002 | Phung et al. |
| 6,416,486 B1 | 7/2002 | Wampler |
| 6,419,675 B1 | 7/2002 | Gallo, Sr. |
| 6,423,073 B2 | 7/2002 | Bowman |
| 6,423,082 B1 | 7/2002 | Houser et al. |
| 6,430,446 B1 | 8/2002 | Knowlton |
| 6,432,118 B1 | 8/2002 | Messerly |
| 6,436,114 B1 | 8/2002 | Novak et al. |
| 6,436,115 B1 | 8/2002 | Beaupre |
| 6,443,968 B1 | 9/2002 | Holthaus et al. |
| 6,443,969 B1 | 9/2002 | Novak et al. |
| 6,454,781 B1 | 9/2002 | Witt et al. |
| 6,454,782 B1 | 9/2002 | Schwemberger |
| 6,458,128 B1 | 10/2002 | Schulze |
| 6,458,130 B1 | 10/2002 | Frazier et al. |
| 6,458,142 B1 | 10/2002 | Faller et al. |
| 6,461,363 B1 | 10/2002 | Gadberry et al. |
| 6,464,689 B1 | 10/2002 | Qin et al. |
| 6,464,702 B2 | 10/2002 | Schulze et al. |
| 6,464,703 B2 | 10/2002 | Bartel |
| 6,471,172 B1 | 10/2002 | Lemke et al. |
| 6,475,211 B2 | 11/2002 | Chess et al. |
| 6,475,216 B2 | 11/2002 | Mulier et al. |
| 6,480,796 B2 | 11/2002 | Wiener |
| 6,485,490 B2 | 11/2002 | Wampler et al. |
| 6,491,690 B1 | 12/2002 | Goble et al. |
| 6,491,691 B1 | 12/2002 | Morley et al. |
| 6,491,701 B2 | 12/2002 | Tierney et al. |
| 6,491,708 B2 | 12/2002 | Madan et al. |
| 6,497,715 B2 | 12/2002 | Satou |
| 6,500,112 B1 | 12/2002 | Khouri |
| 6,500,176 B1 | 12/2002 | Truckai et al. |
| 6,500,188 B2 | 12/2002 | Harper et al. |
| 6,503,248 B1 | 1/2003 | Levine |
| 6,506,208 B2 | 1/2003 | Hunt et al. |
| 6,511,480 B1 | 1/2003 | Tetzlaff et al. |
| 6,514,252 B2 | 2/2003 | Nezhat et al. |
| 6,517,565 B1 | 2/2003 | Whitman et al. |
| 6,520,960 B2 | 2/2003 | Blocher et al. |
| 6,522,909 B1 | 2/2003 | Garibaldi et al. |
| 6,524,316 B1 | 2/2003 | Nicholson et al. |
| 6,531,846 B1 | 3/2003 | Smith |
| 6,533,784 B2 | 3/2003 | Truckai et al. |
| 6,537,196 B1 | 3/2003 | Creighton, IV et al. |
| 6,537,272 B2 | 3/2003 | Christopherson et al. |
| 6,537,291 B2 | 3/2003 | Friedman et al. |
| 6,540,693 B2 | 4/2003 | Burbank et al. |
| 6,543,456 B2 | 4/2003 | Freeman |
| 6,544,260 B1 | 4/2003 | Markel et al. |
| 6,551,309 B1 | 4/2003 | LePivert |
| 6,554,829 B2 | 4/2003 | Schulze et al. |
| 6,558,376 B2 | 5/2003 | Bishop |
| 6,561,983 B2 | 5/2003 | Cronin et al. |
| 6,562,037 B2 | 5/2003 | Paton et al. |
| 6,572,632 B2 | 6/2003 | Zisterer et al. |
| 6,572,639 B1 | 6/2003 | Ingle et al. |
| 6,575,969 B1 | 6/2003 | Rittman, III et al. |
| 6,582,451 B1 | 6/2003 | Marucci et al. |
| 6,584,360 B2 | 6/2003 | Francischelli et al. |
| 6,585,735 B1 | 7/2003 | Frazier et al. |
| 6,589,200 B1 | 7/2003 | Schwemberger et al. |
| 6,589,239 B2 | 7/2003 | Khandkar et al. |
| 6,594,517 B1 | 7/2003 | Nevo |
| 6,599,321 B2 | 7/2003 | Hyde, Jr. |
| 6,602,252 B2 | 8/2003 | Mollenauer |
| 6,610,060 B2 | 8/2003 | Mulier et al. |
| 6,616,450 B2 | 9/2003 | Mossle et al. |
| 6,616,600 B2 | 9/2003 | Pauker |
| 6,619,529 B2 | 9/2003 | Green et al. |
| 6,620,129 B2 | 9/2003 | Stecker et al. |
| 6,620,161 B2 | 9/2003 | Schulze et al. |
| 6,622,731 B2 | 9/2003 | Daniel et al. |
| 6,623,482 B2 | 9/2003 | Pendekanti et al. |
| 6,623,501 B2 | 9/2003 | Heller et al. |
| 6,626,926 B2 | 9/2003 | Friedman et al. |
| 6,633,234 B2 | 10/2003 | Wiener et al. |
| 6,635,057 B2 | 10/2003 | Harano et al. |
| 6,644,532 B2 | 11/2003 | Green et al. |
| 6,648,817 B2 | 11/2003 | Schara et al. |
| 6,651,669 B1 | 11/2003 | Burnside |
| 6,656,177 B2 | 12/2003 | Truckai et al. |
| 6,656,198 B2 | 12/2003 | Tsonton et al. |
| 6,662,127 B2 | 12/2003 | Wiener et al. |
| 6,663,941 B2 | 12/2003 | Brown et al. |
| 6,669,690 B1 | 12/2003 | Okada et al. |
| 6,673,248 B2 | 1/2004 | Chowdhury |
| 6,676,660 B2 | 1/2004 | Wampler et al. |
| 6,678,621 B2 | 1/2004 | Wiener et al. |
| 6,679,882 B1 | 1/2004 | Kornerup |
| 6,679,899 B2 | 1/2004 | Wiener et al. |
| 6,682,501 B1 | 1/2004 | Nelson et al. |
| 6,682,544 B2 | 1/2004 | Mastri et al. |
| 6,695,840 B2 | 2/2004 | Schulze |
| 6,696,844 B2 | 2/2004 | Wong et al. |
| 6,716,215 B1 | 4/2004 | David et al. |
| 6,719,684 B2 | 4/2004 | Kim et al. |
| 6,719,765 B2 | 4/2004 | Bonutti |
| 6,722,552 B2 | 4/2004 | Fenton, Jr. |
| 6,726,686 B2 | 4/2004 | Buysse et al. |
| 6,731,047 B2 | 5/2004 | Kauf et al. |
| 6,733,498 B2 | 5/2004 | Paton et al. |
| 6,733,506 B1 | 5/2004 | McDevitt et al. |
| 6,736,813 B2 | 5/2004 | Yamauchi et al. |
| 6,743,229 B2 | 6/2004 | Buysse et al. |
| 6,746,443 B1 | 6/2004 | Morley et al. |
| 6,752,815 B2 | 6/2004 | Beaupre |
| 6,762,535 B2 | 7/2004 | Take et al. |
| 6,766,202 B2 | 7/2004 | Underwood et al. |
| 6,767,349 B2 | 7/2004 | Ouchi |
| 6,770,072 B1 | 8/2004 | Truckai et al. |
| 6,773,409 B2 | 8/2004 | Truckai et al. |
| 6,773,434 B2 | 8/2004 | Ciarrocca |
| 6,773,435 B2 | 8/2004 | Schulze et al. |
| 6,773,444 B2 | 8/2004 | Messerly |
| 6,775,575 B2 | 8/2004 | Bommannan et al. |
| 6,776,165 B2 | 8/2004 | Jin |
| 6,783,524 B2 | 8/2004 | Anderson et al. |
| 6,786,382 B1 | 9/2004 | Hoffman |
| 6,786,383 B2 | 9/2004 | Stegelmann |
| 6,789,939 B2 | 9/2004 | Schrodinger et al. |
| 6,790,216 B1 | 9/2004 | Lshikawa |
| 6,796,981 B2 | 9/2004 | Wham et al. |
| D496,997 S | 10/2004 | Dycus et al. |
| 6,800,085 B2 | 10/2004 | Selmon et al. |
| 6,802,843 B2 | 10/2004 | Truckai et al. |
| 6,806,317 B2 | 10/2004 | Morishita et al. |
| 6,808,491 B2 | 10/2004 | Kortenbach et al. |
| 6,811,842 B1 | 11/2004 | Ehrnsperger et al. |
| 6,814,731 B2 | 11/2004 | Swanson |
| 6,817,974 B2 | 11/2004 | Cooper et al. |
| 6,821,273 B2 | 11/2004 | Mollenauer |
| 6,828,712 B2 | 12/2004 | Battaglin et al. |
| 6,832,998 B2 | 12/2004 | Goble |

(56) References Cited

U.S. PATENT DOCUMENTS

| | | |
|---|---|---|
| 6,835,199 B2 | 12/2004 | McGuckin, Jr. et al. |
| 6,840,938 B1 | 1/2005 | Morley et al. |
| 6,860,880 B2 | 3/2005 | Treat et al. |
| 6,869,439 B2 | 3/2005 | White et al. |
| 6,875,220 B2 | 4/2005 | Du et al. |
| 6,877,647 B2 | 4/2005 | Green et al. |
| 6,893,435 B2 | 5/2005 | Goble |
| 6,905,497 B2 | 6/2005 | Truckai et al. |
| 6,908,463 B2 | 6/2005 | Treat et al. |
| 6,908,472 B2 | 6/2005 | Wiener et al. |
| 6,913,579 B2 | 7/2005 | Truckai et al. |
| 6,926,716 B2 | 8/2005 | Baker et al. |
| 6,929,622 B2 | 8/2005 | Chian |
| 6,929,632 B2 | 8/2005 | Nita et al. |
| 6,929,644 B2 | 8/2005 | Truckai et al. |
| 6,936,003 B2 | 8/2005 | Iddan |
| D509,589 S | 9/2005 | Wells |
| 6,939,347 B2 | 9/2005 | Thompson |
| 6,945,981 B2 | 9/2005 | Donofrio et al. |
| 6,953,461 B2 | 10/2005 | McClurken et al. |
| D511,145 S | 11/2005 | Donofrio et al. |
| 6,959,852 B2 | 11/2005 | Shelton, IV et al. |
| 6,974,462 B2 | 12/2005 | Sater |
| 6,976,844 B2 | 12/2005 | Hickok et al. |
| 6,976,969 B2 | 12/2005 | Messerly |
| 6,977,495 B2 | 12/2005 | Donofrio |
| 6,984,220 B2 | 1/2006 | Wuchinich |
| 6,986,738 B2 | 1/2006 | Glukhovsky et al. |
| 6,986,780 B2 | 1/2006 | Rudnick et al. |
| 6,994,709 B2 | 2/2006 | Iida |
| 7,000,818 B2 | 2/2006 | Shelton, IV et al. |
| 7,004,951 B2 | 2/2006 | Gibbens, III |
| 7,011,657 B2 | 3/2006 | Truckai et al. |
| 7,029,435 B2 | 4/2006 | Nakao |
| 7,039,453 B2 | 5/2006 | Mullick et al. |
| 7,041,083 B2 | 5/2006 | Chu et al. |
| 7,041,088 B2 | 5/2006 | Nawrocki et al. |
| 7,041,102 B2 | 5/2006 | Truckai et al. |
| 7,044,352 B2 | 5/2006 | Shelton, IV et al. |
| 7,044,937 B1 | 5/2006 | Kirwan et al. |
| 7,052,496 B2 | 5/2006 | Yamauchi |
| 7,055,731 B2 | 6/2006 | Shelton, IV et al. |
| 7,056,284 B2 | 6/2006 | Martone et al. |
| 7,063,699 B2 | 6/2006 | Hess et al. |
| 7,066,879 B2 | 6/2006 | Fowler et al. |
| 7,066,936 B2 | 6/2006 | Ryan |
| 7,070,597 B2 | 7/2006 | Truckai et al. |
| 7,074,219 B2 | 7/2006 | Levine et al. |
| 7,077,039 B2 | 7/2006 | Gass et al. |
| 7,077,853 B2 | 7/2006 | Kramer et al. |
| 7,083,579 B2 | 8/2006 | Yokoi et al. |
| 7,083,617 B2 | 8/2006 | Kortenbach et al. |
| 7,083,618 B2 | 8/2006 | Couture et al. |
| 7,083,619 B2 | 8/2006 | Truckai et al. |
| 7,087,054 B2 | 8/2006 | Truckai et al. |
| 7,090,673 B2 | 8/2006 | Dycus et al. |
| 7,094,235 B2 | 8/2006 | Francischelli |
| 7,096,560 B2 | 8/2006 | Oddsen, Jr. |
| 7,101,371 B2 | 9/2006 | Dycus et al. |
| 7,101,372 B2 | 9/2006 | Dycus et al. |
| 7,101,373 B2 | 9/2006 | Dycus et al. |
| 7,108,695 B2 | 9/2006 | Witt et al. |
| 7,112,201 B2 | 9/2006 | Truckai et al. |
| 7,118,564 B2 | 10/2006 | Ritchie et al. |
| 7,118,570 B2 | 10/2006 | Tetzlaff et al. |
| 7,120,498 B2 | 10/2006 | Imran et al. |
| 7,124,932 B2 | 10/2006 | Isaacson et al. |
| 7,125,409 B2 | 10/2006 | Truckai et al. |
| 7,131,970 B2 | 11/2006 | Moses et al. |
| 7,131,971 B2 | 11/2006 | Dycus et al. |
| 7,135,018 B2 | 11/2006 | Ryan et al. |
| 7,135,030 B2 | 11/2006 | Schwemberger et al. |
| 7,137,980 B2 | 11/2006 | Buysse et al. |
| 7,143,925 B2 | 12/2006 | Shelton, IV et al. |
| 7,147,138 B2 | 12/2006 | Shelton, IV |
| 7,147,638 B2 | 12/2006 | Chapman et al. |
| 7,147,650 B2 | 12/2006 | Lee |
| 7,153,315 B2 | 12/2006 | Miller |
| 7,156,189 B1 | 1/2007 | Bar-Cohen et al. |
| 7,156,846 B2 | 1/2007 | Dycus et al. |
| 7,156,853 B2 | 1/2007 | Muratsu |
| 7,157,058 B2 | 1/2007 | Marhasin et al. |
| 7,159,750 B2 | 1/2007 | Racenet et al. |
| 7,160,296 B2 | 1/2007 | Pearson et al. |
| 7,160,298 B2 | 1/2007 | Lawes et al. |
| 7,163,548 B2 | 1/2007 | Stulen et al. |
| 7,169,104 B2 | 1/2007 | Ueda et al. |
| 7,169,146 B2 | 1/2007 | Truckai et al. |
| 7,169,156 B2 | 1/2007 | Hart |
| 7,170,823 B2 | 1/2007 | Fabricius et al. |
| 7,179,271 B2 | 2/2007 | Friedman et al. |
| 7,186,253 B2 | 3/2007 | Truckai et al. |
| 7,189,233 B2 | 3/2007 | Truckai et al. |
| 7,195,631 B2 | 3/2007 | Dumbauld |
| D541,418 S | 4/2007 | Schechter et al. |
| 7,199,545 B2 | 4/2007 | Oleynikov et al. |
| 7,204,820 B2 | 4/2007 | Akahoshi |
| 7,207,471 B2 | 4/2007 | Heinrich et al. |
| 7,208,005 B2 | 4/2007 | Frecker et al. |
| 7,211,094 B2 | 5/2007 | Gannoe et al. |
| 7,220,951 B2 | 5/2007 | Truckai et al. |
| 7,223,229 B2 | 5/2007 | Inman et al. |
| 7,225,964 B2 | 6/2007 | Mastri et al. |
| 7,226,448 B2 | 6/2007 | Bertolero et al. |
| 7,229,455 B2 | 6/2007 | Sakurai et al. |
| 7,232,440 B2 | 6/2007 | Dumbauld et al. |
| 7,235,064 B2 | 6/2007 | Hopper et al. |
| 7,235,073 B2 | 6/2007 | Levine et al. |
| 7,241,290 B2 | 7/2007 | Doyle et al. |
| 7,241,294 B2 | 7/2007 | Reschke |
| 7,241,296 B2 | 7/2007 | Buysse et al. |
| 7,246,734 B2 | 7/2007 | Shelton, IV |
| 7,251,531 B2 | 7/2007 | Mosher et al. |
| 7,252,667 B2 | 8/2007 | Moses et al. |
| 7,255,697 B2 | 8/2007 | Dycus et al. |
| 7,267,677 B2 | 9/2007 | Johnson et al. |
| 7,267,685 B2 | 9/2007 | Butaric et al. |
| 7,270,658 B2 | 9/2007 | Woloszko et al. |
| 7,270,664 B2 | 9/2007 | Johnson et al. |
| 7,273,483 B2 | 9/2007 | Wiener et al. |
| 7,276,065 B2 | 10/2007 | Morley et al. |
| 7,282,773 B2 | 10/2007 | Li et al. |
| 7,287,682 B1 | 10/2007 | Ezzat et al. |
| 7,297,145 B2 | 11/2007 | Woloszko et al. |
| 7,297,149 B2 | 11/2007 | Vitali et al. |
| 7,300,450 B2 | 11/2007 | Vleugels et al. |
| 7,303,557 B2 | 12/2007 | Wham et al. |
| 7,307,313 B2 | 12/2007 | Ohyanagi et al. |
| 7,309,849 B2 | 12/2007 | Truckai et al. |
| 7,311,709 B2 | 12/2007 | Truckai et al. |
| 7,317,955 B2 | 1/2008 | McGreevy |
| 7,326,236 B2 | 2/2008 | Andreas et al. |
| 7,329,257 B2 | 2/2008 | Kanehira et al. |
| 7,331,410 B2 | 2/2008 | Yong et al. |
| 7,344,533 B2 | 3/2008 | Pearson et al. |
| 7,353,068 B2 | 4/2008 | Tanaka et al. |
| 7,354,440 B2 | 4/2008 | Truckai et al. |
| 7,357,287 B2 | 4/2008 | Shelton, IV et al. |
| 7,360,542 B2 | 4/2008 | Nelson et al. |
| 7,364,577 B2 | 4/2008 | Wham et al. |
| 7,367,973 B2 | 5/2008 | Manzo et al. |
| 7,367,976 B2 | 5/2008 | Lawes et al. |
| 7,371,227 B2 | 5/2008 | Zeiner |
| RE40,388 E | 6/2008 | Gines |
| 7,380,695 B2 | 6/2008 | Doll et al. |
| 7,381,209 B2 | 6/2008 | Truckai et al. |
| 7,384,420 B2 | 6/2008 | Dycus et al. |
| 7,390,317 B2 | 6/2008 | Taylor et al. |
| 7,396,356 B2 | 7/2008 | Mollenauer |
| 7,403,224 B2 | 7/2008 | Fuller et al. |
| 7,404,508 B2 | 7/2008 | Smith et al. |
| 7,407,077 B2 | 8/2008 | Ortiz et al. |
| 7,408,288 B2 | 8/2008 | Hara |
| 7,416,101 B2 | 8/2008 | Shelton, IV et al. |

(56) References Cited

U.S. PATENT DOCUMENTS

| | | |
|---|---|---|
| D576,725 S | 9/2008 | Shumer et al. |
| 7,422,139 B2 | 9/2008 | Shelton, IV et al. |
| 7,422,586 B2 | 9/2008 | Morris et al. |
| 7,422,592 B2 | 9/2008 | Morley et al. |
| 7,429,259 B2 | 9/2008 | Cadeddu et al. |
| D578,643 S | 10/2008 | Shumer et al. |
| D578,644 S | 10/2008 | Shumer et al. |
| D578,645 S | 10/2008 | Shumer et al. |
| 7,431,704 B2 | 10/2008 | Babaev |
| 7,435,249 B2 | 10/2008 | Buysse et al. |
| 7,435,582 B2 | 10/2008 | Zimmermann et al. |
| 7,439,732 B2 | 10/2008 | LaPlaca |
| 7,441,684 B2 | 10/2008 | Shelton, IV et al. |
| 7,442,193 B2 | 10/2008 | Shields et al. |
| 7,442,194 B2 | 10/2008 | Dumbauld et al. |
| 7,445,621 B2 | 11/2008 | Dumbauld et al. |
| 7,448,993 B2 | 11/2008 | Yokoi et al. |
| 7,449,004 B2 | 11/2008 | Yamada et al. |
| 7,450,998 B2 | 11/2008 | Zilberman et al. |
| 7,451,904 B2 | 11/2008 | Shelton, IV |
| 7,464,846 B2 | 12/2008 | Shelton, IV et al. |
| 7,472,815 B2 | 1/2009 | Shelton, IV et al. |
| 7,473,253 B2 | 1/2009 | Dycus et al. |
| 7,479,148 B2 | 1/2009 | Beau Pre |
| 7,479,160 B2 | 1/2009 | Branch et al. |
| 7,487,899 B2 | 2/2009 | Shelton, IV et al. |
| 7,488,319 B2 | 2/2009 | Yates |
| 7,491,201 B2 | 2/2009 | Shields et al. |
| 7,494,468 B2 | 2/2009 | Rabiner et al. |
| 7,494,501 B2 | 2/2009 | Ahlberg et al. |
| 7,498,080 B2 | 3/2009 | Tung et al. |
| 7,503,893 B2 | 3/2009 | Kucklick |
| 7,505,812 B1 | 3/2009 | Eggers et al. |
| 7,506,791 B2 | 3/2009 | Omaits et al. |
| 7,510,107 B2 | 3/2009 | Timm et al. |
| 7,510,556 B2 | 3/2009 | Nguyen et al. |
| 7,511,733 B2 | 3/2009 | Takizawa et al. |
| 7,513,025 B2 | 4/2009 | Fischer |
| 7,517,349 B2 | 4/2009 | Truckai et al. |
| 7,520,877 B2 | 4/2009 | Lee, Jr. et al. |
| 7,524,320 B2 | 4/2009 | Tierney et al. |
| 7,534,243 B1 | 5/2009 | Chin et al. |
| D594,983 S | 6/2009 | Price et al. |
| 7,540,872 B2 | 6/2009 | Schechter et al. |
| 7,543,730 B1 | 6/2009 | Marczyk |
| 7,544,200 B2 | 6/2009 | Houser |
| 7,550,216 B2 | 6/2009 | Ofer et al. |
| 7,553,309 B2 | 6/2009 | Buysse et al. |
| 7,559,452 B2 | 7/2009 | Wales et al. |
| 7,566,318 B2 | 7/2009 | Haefner |
| 7,567,012 B2 | 7/2009 | Namikawa |
| 7,582,086 B2 | 9/2009 | Privitera et al. |
| 7,582,087 B2 | 9/2009 | Tetzlaff et al. |
| 7,586,289 B2 | 9/2009 | Andruk et al. |
| 7,588,176 B2 | 9/2009 | Timm et al. |
| 7,588,177 B2 | 9/2009 | Racenet |
| 7,594,925 B2 | 9/2009 | Danek et al. |
| 7,597,693 B2 | 10/2009 | Garrison |
| 7,599,743 B2 | 10/2009 | Hassler, Jr. et al. |
| 7,601,119 B2 | 10/2009 | Shahinian |
| 7,604,150 B2 | 10/2009 | Boudreaux |
| 7,608,083 B2 | 10/2009 | Lee et al. |
| 7,611,512 B2 | 11/2009 | Ein-Gal |
| 7,617,961 B2 | 11/2009 | Viola |
| 7,621,910 B2 | 11/2009 | Sugi |
| 7,621,930 B2 | 11/2009 | Houser |
| 7,625,370 B2 | 12/2009 | Hart et al. |
| 7,628,791 B2 | 12/2009 | Garrison et al. |
| 7,628,792 B2 | 12/2009 | Guerra |
| 7,632,267 B2 | 12/2009 | Dahla |
| 7,632,269 B2 | 12/2009 | Truckai et al. |
| 7,637,410 B2 | 12/2009 | Marczyk |
| 7,640,447 B2 | 12/2009 | Qiu |
| 7,641,653 B2 | 1/2010 | Dalla Betta et al. |
| 7,641,671 B2 | 1/2010 | Crainich |
| 7,644,848 B2 | 1/2010 | Swayze et al. |
| 7,645,277 B2 | 1/2010 | McClurken et al. |
| 7,648,499 B2 | 1/2010 | Orszulak et al. |
| 7,658,311 B2 | 2/2010 | Boudreaux |
| 7,662,151 B2 | 2/2010 | Crompton, Jr. et al. |
| 7,665,647 B2 | 2/2010 | Shelton, IV et al. |
| 7,666,206 B2 | 2/2010 | Taniguchi et al. |
| 7,670,334 B2 | 3/2010 | Hueil et al. |
| 7,678,043 B2 | 3/2010 | Gilad |
| 7,678,105 B2 | 3/2010 | McGreevy et al. |
| 7,686,804 B2 | 3/2010 | Johnson et al. |
| 7,691,095 B2 | 4/2010 | Bednarek et al. |
| 7,691,098 B2 | 4/2010 | Wallace et al. |
| 7,691,103 B2 | 4/2010 | Fernandez et al. |
| 7,703,459 B2 | 4/2010 | Saadat et al. |
| 7,703,653 B2 | 4/2010 | Shah et al. |
| 7,708,735 B2 | 5/2010 | Chapman et al. |
| 7,708,751 B2 | 5/2010 | Hughes et al. |
| 7,708,758 B2 | 5/2010 | Lee et al. |
| 7,717,312 B2 | 5/2010 | Beetel |
| 7,717,914 B2 | 5/2010 | Kimura |
| 7,717,915 B2 | 5/2010 | Miyazawa |
| 7,722,527 B2 | 5/2010 | Bouchier et al. |
| 7,722,607 B2 | 5/2010 | Dumbauld et al. |
| 7,725,214 B2 | 5/2010 | Diolaiti |
| D618,797 S | 6/2010 | Price et al. |
| 7,726,537 B2 | 6/2010 | Olson et al. |
| 7,744,615 B2 | 6/2010 | Couture |
| 7,751,115 B2 | 7/2010 | Song |
| 7,753,904 B2 | 7/2010 | Shelton, IV et al. |
| 7,753,908 B2 | 7/2010 | Swanson |
| 7,753,909 B2 | 7/2010 | Chapman et al. |
| 7,762,445 B2 | 7/2010 | Heinrich et al. |
| D621,503 S | 8/2010 | Otten et al. |
| 7,766,210 B2 | 8/2010 | Shelton, IV et al. |
| 7,766,910 B2 | 8/2010 | Hixson et al. |
| 7,770,774 B2 | 8/2010 | Mastri et al. |
| 7,770,775 B2 | 8/2010 | Shelton, IV et al. |
| 7,775,972 B2 | 8/2010 | Brock et al. |
| 7,776,036 B2 | 8/2010 | Schechter et al. |
| 7,776,037 B2 | 8/2010 | Odom |
| 7,780,651 B2 | 8/2010 | Madhani et al. |
| 7,780,659 B2 | 8/2010 | Okada et al. |
| 7,780,663 B2 | 8/2010 | Yates et al. |
| 7,784,663 B2 | 8/2010 | Shelton, IV |
| 7,789,283 B2 | 9/2010 | Shah |
| 7,789,878 B2 | 9/2010 | Dumbauld et al. |
| 7,789,883 B2 | 9/2010 | Takashino et al. |
| 7,793,814 B2 | 9/2010 | Racenet et al. |
| 7,799,027 B2 | 9/2010 | Hafner |
| 7,803,156 B2 | 9/2010 | Eder et al. |
| 7,806,891 B2 | 10/2010 | Nowlin et al. |
| 7,810,692 B2 | 10/2010 | Hall et al. |
| 7,810,693 B2 | 10/2010 | Broehl et al. |
| 7,815,641 B2 | 10/2010 | Dodde et al. |
| 7,819,298 B2 | 10/2010 | Hall et al. |
| 7,819,299 B2 | 10/2010 | Shelton, IV et al. |
| 7,819,872 B2 | 10/2010 | Johnson et al. |
| D627,066 S | 11/2010 | Romero |
| 7,824,401 B2 | 11/2010 | Manzo et al. |
| 7,832,408 B2 | 11/2010 | Shelton, IV et al. |
| 7,832,612 B2 | 11/2010 | Baxter, III et al. |
| 7,837,699 B2 | 11/2010 | Yamada et al. |
| 7,845,537 B2 | 12/2010 | Shelton, IV et al. |
| 7,846,159 B2 | 12/2010 | Morrison et al. |
| 7,846,160 B2 | 12/2010 | Payne et al. |
| 7,850,688 B2 | 12/2010 | Hafner |
| D631,155 S | 1/2011 | Peine et al. |
| 7,861,906 B2 | 1/2011 | Doll et al. |
| 7,862,560 B2 | 1/2011 | Marion |
| 7,867,228 B2 | 1/2011 | Nobis et al. |
| 7,871,392 B2 | 1/2011 | Sartor |
| 7,871,423 B2 | 1/2011 | Livneh |
| D631,965 S | 2/2011 | Price et al. |
| 7,877,852 B2 | 2/2011 | Unger et al. |
| 7,877,853 B2 | 2/2011 | Unger et al. |
| 7,879,035 B2 | 2/2011 | Garrison et al. |
| 7,879,070 B2 | 2/2011 | Ortiz et al. |
| 7,887,535 B2 | 2/2011 | Lands et al. |

(56) References Cited

U.S. PATENT DOCUMENTS

| | | |
|---|---|---|
| 7,892,606 B2 | 2/2011 | Thies et al. |
| 7,896,875 B2 | 3/2011 | Heim et al. |
| 7,896,878 B2 | 3/2011 | Johnson et al. |
| 7,901,400 B2 | 3/2011 | Wham et al. |
| 7,901,423 B2 | 3/2011 | Stulen et al. |
| 7,905,881 B2 | 3/2011 | Masuda et al. |
| 7,909,220 B2 | 3/2011 | Viola |
| 7,919,184 B2 | 4/2011 | Mohapatra et al. |
| 7,922,061 B2 | 4/2011 | Shelton, IV et al. |
| 7,922,651 B2 | 4/2011 | Yamada et al. |
| 7,922,953 B2 | 4/2011 | Guerra |
| 7,931,649 B2 | 4/2011 | Couture et al. |
| D637,288 S | 5/2011 | Houghton |
| D638,540 S | 5/2011 | Ijiri et al. |
| 7,935,114 B2 | 5/2011 | Takashino et al. |
| 7,942,303 B2 | 5/2011 | Shah |
| 7,942,868 B2 | 5/2011 | Cooper |
| 7,947,039 B2 | 5/2011 | Sartor |
| 7,951,165 B2 | 5/2011 | Golden et al. |
| 7,955,331 B2 | 6/2011 | Truckai et al. |
| 7,959,050 B2 | 6/2011 | Smith et al. |
| 7,959,626 B2 | 6/2011 | Hong et al. |
| 7,963,963 B2 | 6/2011 | Francischelli et al. |
| 7,967,602 B2 | 6/2011 | Lindquist |
| 7,976,544 B2 | 7/2011 | McClurken et al. |
| 7,980,443 B2 | 7/2011 | Scheib et al. |
| 7,981,113 B2 | 7/2011 | Truckai et al. |
| 7,988,567 B2 | 8/2011 | Kim et al. |
| 7,997,278 B2 | 8/2011 | Utley et al. |
| 8,020,743 B2 | 9/2011 | Shelton, IV |
| 8,033,173 B2 | 10/2011 | Ehlert et al. |
| 8,038,612 B2 | 10/2011 | Paz |
| 8,038,693 B2 | 10/2011 | Allen |
| 8,048,070 B2 | 11/2011 | O'Brien et al. |
| 8,052,672 B2 | 11/2011 | Laufer et al. |
| 8,056,720 B2 | 11/2011 | Hawkes |
| 8,056,787 B2 | 11/2011 | Boudreaux et al. |
| 8,057,498 B2 | 11/2011 | Robertson |
| 8,058,771 B2 | 11/2011 | Giordano et al. |
| 8,061,014 B2 | 11/2011 | Smith et al. |
| 8,062,211 B2 | 11/2011 | Duval et al. |
| 8,066,167 B2 | 11/2011 | Measamer et al. |
| 8,070,036 B1 | 12/2011 | Knodel |
| 8,070,748 B2 | 12/2011 | Hixson et al. |
| 8,075,555 B2 | 12/2011 | Truckai et al. |
| 8,075,558 B2 | 12/2011 | Truckai et al. |
| 8,092,475 B2 | 1/2012 | Cotter et al. |
| 8,100,894 B2 | 1/2012 | Mucko et al. |
| 8,105,323 B2 | 1/2012 | Buysse et al. |
| 8,105,324 B2 | 1/2012 | Palanker et al. |
| 8,114,104 B2 | 2/2012 | Young et al. |
| 8,114,119 B2 | 2/2012 | Spivey et al. |
| 8,128,624 B2 | 3/2012 | Couture et al. |
| 8,128,657 B2 | 3/2012 | Shiono et al. |
| 8,133,218 B2 | 3/2012 | Daw et al. |
| 8,136,712 B2 | 3/2012 | Zingman |
| 8,141,762 B2 | 3/2012 | Bedi et al. |
| 8,142,461 B2 | 3/2012 | Houser et al. |
| 8,147,488 B2 | 4/2012 | Masuda |
| 8,147,508 B2 | 4/2012 | Madan et al. |
| 8,152,825 B2 | 4/2012 | Madan et al. |
| 8,157,145 B2 | 4/2012 | Shelton, IV et al. |
| 8,161,977 B2 | 4/2012 | Shelton, IV et al. |
| 8,162,940 B2 | 4/2012 | Johnson et al. |
| 8,177,794 B2 | 5/2012 | Cabrera et al. |
| 8,182,502 B2 | 5/2012 | Stulen et al. |
| 8,186,560 B2 | 5/2012 | Hess et al. |
| 8,187,166 B2 | 5/2012 | Kuth et al. |
| 8,187,267 B2 | 5/2012 | Pappone et al. |
| 8,192,433 B2 | 6/2012 | Johnson et al. |
| 8,197,472 B2 | 6/2012 | Lau et al. |
| 8,197,479 B2 | 6/2012 | Olson et al. |
| 8,197,494 B2 | 6/2012 | Jaggi et al. |
| 8,197,502 B2 | 6/2012 | Smith et al. |
| 8,206,212 B2 | 6/2012 | Iddings et al. |
| 8,221,415 B2 | 7/2012 | Francischelli |
| 8,221,416 B2 | 7/2012 | Townsend |
| 8,226,675 B2 | 7/2012 | Houser et al. |
| 8,236,019 B2 | 8/2012 | Houser |
| 8,236,020 B2 | 8/2012 | Smith et al. |
| 8,241,235 B2 | 8/2012 | Kahler et al. |
| 8,241,283 B2 | 8/2012 | Guerra et al. |
| 8,241,284 B2 | 8/2012 | Dycus et al. |
| 8,241,312 B2 | 8/2012 | Messerly |
| 8,244,368 B2 | 8/2012 | Sherman |
| 8,246,615 B2 | 8/2012 | Behnke |
| 8,246,618 B2 | 8/2012 | Bucciaglia et al. |
| 8,251,994 B2 | 8/2012 | McKenna et al. |
| 8,252,012 B2 | 8/2012 | Stulen |
| 8,257,352 B2 | 9/2012 | Lawes et al. |
| 8,257,377 B2 | 9/2012 | Wiener et al. |
| 8,262,563 B2 | 9/2012 | Bakos et al. |
| 8,267,300 B2 | 9/2012 | Boudreaux |
| 8,267,854 B2 | 9/2012 | Asada et al. |
| 8,267,935 B2 | 9/2012 | Couture et al. |
| 8,273,085 B2 | 9/2012 | Park et al. |
| 8,277,446 B2 | 10/2012 | Heard |
| 8,277,447 B2 | 10/2012 | Garrison et al. |
| 8,277,471 B2 | 10/2012 | Wiener et al. |
| 8,282,581 B2 | 10/2012 | Zhao et al. |
| 8,282,669 B2 | 10/2012 | Gerber et al. |
| 8,287,528 B2 | 10/2012 | Wham et al. |
| 8,292,886 B2 | 10/2012 | Kerr et al. |
| 8,292,888 B2 | 10/2012 | Whitman |
| 8,298,228 B2 | 10/2012 | Buysse et al. |
| 8,298,232 B2 | 10/2012 | Unger |
| 8,303,583 B2 | 11/2012 | Hosier et al. |
| 8,306,629 B2 | 11/2012 | Mioduski et al. |
| 8,308,040 B2 | 11/2012 | Huang et al. |
| 8,319,400 B2 | 11/2012 | Houser et al. |
| 8,322,455 B2 | 12/2012 | Shelton, IV et al. |
| 8,323,302 B2 | 12/2012 | Robertson et al. |
| 8,323,310 B2 | 12/2012 | Kingsley |
| 8,328,061 B2 | 12/2012 | Kasvikis |
| 8,328,761 B2 | 12/2012 | Widenhouse et al. |
| 8,328,834 B2 | 12/2012 | Isaacs et al. |
| 8,333,778 B2 | 12/2012 | Smith et al. |
| 8,333,779 B2 | 12/2012 | Smith et al. |
| 8,334,468 B2 | 12/2012 | Palmer et al. |
| 8,334,635 B2 | 12/2012 | Voegele et al. |
| 8,338,726 B2 | 12/2012 | Palmer et al. |
| 8,343,146 B2 | 1/2013 | Godara et al. |
| 8,344,596 B2 | 1/2013 | Nield et al. |
| 8,348,880 B2 | 1/2013 | Messerly et al. |
| 8,348,947 B2 | 1/2013 | Takashino et al. |
| 8,348,967 B2 | 1/2013 | Stulen |
| 8,353,297 B2 | 1/2013 | Dacquay et al. |
| 8,357,158 B2 | 1/2013 | McKenna et al. |
| 8,361,569 B2 | 1/2013 | Saito et al. |
| 8,372,064 B2 | 2/2013 | Douglass et al. |
| 8,372,099 B2 | 2/2013 | Deville et al. |
| 8,372,101 B2 | 2/2013 | Smith et al. |
| 8,377,053 B2 | 2/2013 | Orszulak |
| 8,377,059 B2 | 2/2013 | Deville et al. |
| 8,377,085 B2 | 2/2013 | Smith et al. |
| 8,382,754 B2 | 2/2013 | Odom et al. |
| 8,382,782 B2 | 2/2013 | Robertson et al. |
| 8,382,792 B2 | 2/2013 | Chojin |
| 8,388,646 B2 | 3/2013 | Chojin |
| 8,388,647 B2 | 3/2013 | Nau, Jr. et al. |
| 8,394,094 B2 | 3/2013 | Edwards et al. |
| 8,394,115 B2 | 3/2013 | Houser et al. |
| 8,397,971 B2 | 3/2013 | Yates et al. |
| 8,398,633 B2 | 3/2013 | Mueller |
| 8,403,926 B2 | 3/2013 | Nobis et al. |
| 8,403,948 B2 | 3/2013 | Deville et al. |
| 8,403,949 B2 | 3/2013 | Palmer et al. |
| 8,403,950 B2 | 3/2013 | Palmer et al. |
| 8,409,076 B2 | 4/2013 | Pang et al. |
| 8,414,577 B2 | 4/2013 | Boudreaux et al. |
| 8,418,349 B2 | 4/2013 | Smith et al. |
| 8,419,757 B2 | 4/2013 | Smith et al. |
| 8,419,758 B2 | 4/2013 | Smith et al. |
| 8,419,759 B2 | 4/2013 | Dietz |

(56) References Cited

U.S. PATENT DOCUMENTS

| | | |
|---|---|---|
| 8,425,410 B2 | 4/2013 | Murray et al. |
| 8,425,545 B2 | 4/2013 | Smith et al. |
| 8,430,811 B2 | 4/2013 | Hess et al. |
| 8,430,876 B2 | 4/2013 | Kappus et al. |
| 8,430,897 B2 | 4/2013 | Novak et al. |
| 8,430,898 B2 | 4/2013 | Wiener et al. |
| 8,435,257 B2 | 5/2013 | Smith et al. |
| 8,439,911 B2 | 5/2013 | Mueller |
| 8,439,939 B2 | 5/2013 | Deville et al. |
| 8,444,662 B2 | 5/2013 | Palmer et al. |
| 8,444,664 B2 | 5/2013 | Balanev et al. |
| 8,453,906 B2 | 6/2013 | Huang et al. |
| 8,454,599 B2 | 6/2013 | Inagaki et al. |
| 8,454,639 B2 | 6/2013 | Du et al. |
| 8,460,288 B2 | 6/2013 | Tamai et al. |
| 8,460,292 B2 | 6/2013 | Truckai et al. |
| 8,461,744 B2 | 6/2013 | Wiener et al. |
| 8,469,956 B2 | 6/2013 | McKenna et al. |
| 8,469,981 B2 | 6/2013 | Robertson et al. |
| 8,475,361 B2 | 7/2013 | Barlow et al. |
| 8,475,453 B2 | 7/2013 | Marczyk et al. |
| 8,480,703 B2 | 7/2013 | Nicholas et al. |
| 8,484,833 B2 | 7/2013 | Cunningham et al. |
| 8,485,413 B2 | 7/2013 | Scheib et al. |
| 8,485,970 B2 | 7/2013 | Widenhouse et al. |
| 8,486,057 B2 | 7/2013 | Behnke, II |
| 8,486,096 B2 | 7/2013 | Robertson et al. |
| 8,491,625 B2 | 7/2013 | Homer |
| 8,496,682 B2 | 7/2013 | Guerra et al. |
| 8,512,336 B2 | 8/2013 | Couture |
| 8,512,364 B2 | 8/2013 | Kowalski et al. |
| 8,512,365 B2 | 8/2013 | Wiener et al. |
| 8,523,889 B2 | 9/2013 | Stulen et al. |
| 8,529,437 B2 | 9/2013 | Taylor et al. |
| 8,529,565 B2 | 9/2013 | Masuda et al. |
| 8,531,064 B2 | 9/2013 | Robertson et al. |
| 8,535,311 B2 | 9/2013 | Schall |
| 8,535,340 B2 | 9/2013 | Allen |
| 8,535,341 B2 | 9/2013 | Allen |
| 8,540,128 B2 | 9/2013 | Shelton, IV et al. |
| 8,542,501 B2 | 9/2013 | Kyono |
| 8,553,430 B2 | 10/2013 | Melanson et al. |
| 8,562,516 B2 | 10/2013 | Saadat et al. |
| 8,562,592 B2 | 10/2013 | Conlon et al. |
| 8,562,598 B2 | 10/2013 | Falkenstein et al. |
| 8,562,604 B2 | 10/2013 | Nishimura |
| 8,568,390 B2 | 10/2013 | Mueller |
| 8,568,412 B2 | 10/2013 | Brandt et al. |
| 8,569,997 B2 | 10/2013 | Lee |
| 8,574,187 B2 | 11/2013 | Marion |
| 8,574,231 B2 | 11/2013 | Boudreaux et al. |
| 8,579,176 B2 | 11/2013 | Smith et al. |
| 8,579,928 B2 | 11/2013 | Robertson et al. |
| 8,579,937 B2 | 11/2013 | Gresham |
| 8,591,459 B2 | 11/2013 | Clymer et al. |
| 8,591,506 B2 | 11/2013 | Wham et al. |
| D695,407 S | 12/2013 | Price et al. |
| 8,596,513 B2 | 12/2013 | Olson et al. |
| 8,597,182 B2 | 12/2013 | Stein et al. |
| 8,597,297 B2 | 12/2013 | Couture et al. |
| 8,608,044 B2 | 12/2013 | Hueil et al. |
| 8,613,383 B2 | 12/2013 | Beckman et al. |
| 8,622,274 B2 | 1/2014 | Yates et al. |
| 8,623,011 B2 | 1/2014 | Spivey |
| 8,623,016 B2 | 1/2014 | Fischer |
| 8,623,027 B2 | 1/2014 | Price et al. |
| 8,623,044 B2 | 1/2014 | Timm et al. |
| 8,628,529 B2 | 1/2014 | Aldridge et al. |
| 8,632,461 B2 | 1/2014 | Glossop |
| 8,632,539 B2 | 1/2014 | Twomey et al. |
| 8,636,648 B2 | 1/2014 | Gazdzinski |
| 8,636,736 B2 | 1/2014 | Yates et al. |
| 8,636,761 B2 | 1/2014 | Cunningham et al. |
| 8,638,428 B2 | 1/2014 | Brown |
| 8,640,788 B2 | 2/2014 | Dachs, II et al. |
| 8,641,712 B2 | 2/2014 | Couture |
| 8,647,350 B2 | 2/2014 | Mohan et al. |
| 8,650,728 B2 | 2/2014 | Wan et al. |
| 8,652,120 B2 | 2/2014 | Giordano et al. |
| 8,652,155 B2 | 2/2014 | Houser et al. |
| 8,663,220 B2 | 3/2014 | Wiener et al. |
| 8,663,222 B2 | 3/2014 | Anderson et al. |
| 8,663,223 B2 | 3/2014 | Masuda et al. |
| 8,668,691 B2 | 3/2014 | Heard |
| RE44,834 E | 4/2014 | Dumbauld et al. |
| 8,684,253 B2 | 4/2014 | Giordano et al. |
| 8,685,020 B2 | 4/2014 | Weizman et al. |
| 8,685,056 B2 | 4/2014 | Evans et al. |
| 8,696,662 B2 | 4/2014 | Eder et al. |
| 8,696,665 B2 | 4/2014 | Hunt et al. |
| 8,702,609 B2 | 4/2014 | Hadjicostis |
| 8,702,704 B2 | 4/2014 | Shelton, IV et al. |
| 8,708,213 B2 | 4/2014 | Shelton, IV et al. |
| 8,709,035 B2 | 4/2014 | Johnson et al. |
| 8,715,270 B2 | 5/2014 | Weitzner et al. |
| 8,715,277 B2 | 5/2014 | Weizman |
| 8,721,640 B2 | 5/2014 | Taylor et al. |
| 8,734,443 B2 | 5/2014 | Hixson et al. |
| 8,747,238 B2 | 6/2014 | Shelton, IV et al. |
| 8,747,351 B2 | 6/2014 | Schultz |
| 8,747,404 B2 | 6/2014 | Boudreaux et al. |
| 8,752,264 B2 | 6/2014 | Ackley et al. |
| 8,752,749 B2 | 6/2014 | Moore et al. |
| 8,753,338 B2 | 6/2014 | Widenhouse et al. |
| 8,758,342 B2 | 6/2014 | Bales et al. |
| 8,764,747 B2 | 7/2014 | Cummings et al. |
| 8,770,459 B2 | 7/2014 | Racenet et al. |
| 8,784,418 B2 | 7/2014 | Romero |
| 8,789,740 B2 | 7/2014 | Baxter, III et al. |
| 8,790,342 B2 | 7/2014 | Stulen et al. |
| 8,795,274 B2 | 8/2014 | Hanna |
| 8,795,276 B2 | 8/2014 | Dietz et al. |
| 8,795,327 B2 | 8/2014 | Dietz et al. |
| 8,800,838 B2 | 8/2014 | Shelton, IV |
| 8,801,752 B2 | 8/2014 | Fortier et al. |
| 8,807,414 B2 | 8/2014 | Ross et al. |
| 8,808,319 B2 | 8/2014 | Houser et al. |
| 8,814,856 B2 | 8/2014 | Elmouelhi et al. |
| 8,814,865 B2 | 8/2014 | Reschke |
| 8,814,870 B2 | 8/2014 | Paraschiv et al. |
| 8,827,992 B2 | 9/2014 | Koss et al. |
| 8,827,995 B2 | 9/2014 | Schaller et al. |
| 8,834,466 B2 | 9/2014 | Cummings et al. |
| 8,834,488 B2 | 9/2014 | Farritor et al. |
| 8,834,518 B2 | 9/2014 | Faller et al. |
| 8,845,630 B2 | 9/2014 | Mehta et al. |
| 8,851,354 B2 | 10/2014 | Swensgard et al. |
| 8,852,184 B2 | 10/2014 | Kucklick |
| 8,864,757 B2 | 10/2014 | Klimovitch et al. |
| 8,864,761 B2 | 10/2014 | Johnson et al. |
| 8,870,867 B2 | 10/2014 | Walberg et al. |
| 8,876,858 B2 | 11/2014 | Braun |
| 8,882,766 B2 | 11/2014 | Couture et al. |
| 8,882,791 B2 | 11/2014 | Stulen |
| 8,887,373 B2 | 11/2014 | Brandt et al. |
| 8,888,776 B2 | 11/2014 | Dietz et al. |
| 8,888,783 B2 | 11/2014 | Young |
| 8,888,809 B2 | 11/2014 | Davison et al. |
| 8,906,012 B2 | 12/2014 | Conley et al. |
| 8,906,016 B2 | 12/2014 | Boudreaux et al. |
| 8,906,017 B2 | 12/2014 | Rioux et al. |
| 8,911,438 B2 | 12/2014 | Swoyer et al. |
| 8,911,460 B2 | 12/2014 | Neurohr et al. |
| 8,926,607 B2 | 1/2015 | Norvell et al. |
| 8,926,608 B2 | 1/2015 | Bacher et al. |
| 8,929,888 B2 | 1/2015 | Rao et al. |
| 8,931,682 B2 | 1/2015 | Timm et al. |
| 8,939,287 B2 | 1/2015 | Markovitch |
| 8,939,974 B2 | 1/2015 | Boudreaux et al. |
| 8,939,975 B2 | 1/2015 | Twomey et al. |
| 8,944,997 B2 | 2/2015 | Fernandez et al. |
| 8,945,125 B2 | 2/2015 | Schechter et al. |
| 8,951,248 B2 | 2/2015 | Messerly et al. |
| 8,951,272 B2 | 2/2015 | Robertson et al. |

(56) References Cited

U.S. PATENT DOCUMENTS

| | | |
|---|---|---|
| 8,956,349 B2 | 2/2015 | Aldridge et al. |
| 8,960,520 B2 | 2/2015 | McCuen |
| 8,961,515 B2 | 2/2015 | Twomey et al. |
| 8,961,547 B2 | 2/2015 | Dietz et al. |
| 8,968,276 B2 | 3/2015 | Zemlok et al. |
| 8,968,308 B2 | 3/2015 | Homer et al. |
| 8,968,312 B2 | 3/2015 | Marczyk et al. |
| 8,968,332 B2 | 3/2015 | Farritor et al. |
| 8,974,453 B2 | 3/2015 | Wang |
| 8,978,845 B2 | 3/2015 | Kim |
| 8,979,838 B2 | 3/2015 | Woloszko et al. |
| 8,979,843 B2 | 3/2015 | Timm et al. |
| 8,979,844 B2 | 3/2015 | White et al. |
| 8,979,890 B2 | 3/2015 | Boudreaux |
| 8,986,302 B2 | 3/2015 | Aldridge et al. |
| 8,989,855 B2 | 3/2015 | Murphy et al. |
| 8,992,422 B2 | 3/2015 | Spivey et al. |
| 8,992,520 B2 * | 3/2015 | Van Wyk ............ A61B 18/1402 606/41 |
| 8,992,526 B2 | 3/2015 | Brodbeck et al. |
| 9,005,199 B2 | 4/2015 | Beckman et al. |
| 9,011,437 B2 | 4/2015 | Woodruff et al. |
| 9,017,326 B2 | 4/2015 | DiNardo et al. |
| 9,017,372 B2 | 4/2015 | Artale et al. |
| 9,028,494 B2 | 5/2015 | Shelton, IV et al. |
| 9,028,519 B2 | 5/2015 | Yates et al. |
| 9,031,667 B2 | 5/2015 | Williams |
| 9,033,983 B2 | 5/2015 | Takashino et al. |
| 9,039,695 B2 | 5/2015 | Giordano et al. |
| 9,039,705 B2 | 5/2015 | Takashino |
| 9,039,731 B2 | 5/2015 | Joseph |
| 9,044,227 B2 | 6/2015 | Shelton, IV et al. |
| 9,044,243 B2 | 6/2015 | Johnson et al. |
| 9,044,245 B2 | 6/2015 | Condie et al. |
| 9,044,256 B2 | 6/2015 | Cadeddu et al. |
| 9,044,261 B2 | 6/2015 | Houser |
| 9,050,093 B2 | 6/2015 | Aldridge et al. |
| 9,050,098 B2 | 6/2015 | Deville et al. |
| 9,050,113 B2 * | 6/2015 | Bloom .................. A61B 18/14 |
| 9,055,961 B2 | 6/2015 | Manzo et al. |
| 9,060,770 B2 | 6/2015 | Shelton, IV et al. |
| 9,060,775 B2 | 6/2015 | Wiener et al. |
| 9,060,776 B2 | 6/2015 | Yates et al. |
| 9,066,723 B2 | 6/2015 | Beller et al. |
| 9,072,535 B2 | 7/2015 | Shelton, IV et al. |
| 9,072,536 B2 | 7/2015 | Shelton, IV et al. |
| 9,078,664 B2 | 7/2015 | Palmer et al. |
| 9,089,327 B2 | 7/2015 | Worrell et al. |
| 9,089,360 B2 | 7/2015 | Messerly et al. |
| 9,094,006 B2 | 7/2015 | Gravati et al. |
| 9,095,362 B2 | 8/2015 | Dachs, II et al. |
| 9,095,367 B2 | 8/2015 | Olson et al. |
| 9,101,385 B2 | 8/2015 | Shelton, IV et al. |
| 9,107,672 B2 | 8/2015 | Tetzlaff et al. |
| 9,113,889 B2 | 8/2015 | Reschke |
| 9,113,900 B2 | 8/2015 | Buysse et al. |
| 9,119,630 B2 | 9/2015 | Townsend et al. |
| 9,119,657 B2 | 9/2015 | Shelton, IV et al. |
| 9,119,957 B2 | 9/2015 | Gantz et al. |
| 9,125,662 B2 | 9/2015 | Shelton, IV |
| 9,125,667 B2 | 9/2015 | Stone et al. |
| 9,138,289 B2 | 9/2015 | Conley et al. |
| 9,149,324 B2 | 10/2015 | Huang et al. |
| 9,149,325 B2 | 10/2015 | Worrell et al. |
| 9,155,585 B2 | 10/2015 | Bales, Jr. et al. |
| 9,161,803 B2 | 10/2015 | Yates et al. |
| 9,168,054 B2 | 10/2015 | Turner et al. |
| 9,168,085 B2 | 10/2015 | Juzkiw et al. |
| 9,168,089 B2 | 10/2015 | Buysse et al. |
| 9,179,912 B2 | 11/2015 | Yates et al. |
| 9,186,204 B2 | 11/2015 | Nishimura et al. |
| 9,187,758 B2 | 11/2015 | Cai et al. |
| 9,192,380 B2 | 11/2015 | (Tarinelli) Racenet et al. |
| 9,192,421 B2 | 11/2015 | Garrison |
| 9,192,431 B2 | 11/2015 | Woodruff et al. |
| 9,198,714 B2 | 12/2015 | Worrell et al. |
| 9,198,715 B2 | 12/2015 | Livneh |
| 9,198,716 B2 | 12/2015 | Masuda et al. |
| 9,204,879 B2 | 12/2015 | Shelton, IV |
| 9,204,919 B2 | 12/2015 | Brandt et al. |
| 9,216,050 B2 | 12/2015 | Condie et al. |
| 9,220,559 B2 | 12/2015 | Worrell et al. |
| 9,226,751 B2 | 1/2016 | Shelton, IV et al. |
| 9,226,767 B2 | 1/2016 | Stulen et al. |
| 9,237,891 B2 | 1/2016 | Shelton, IV |
| 9,254,165 B2 | 2/2016 | Aronow et al. |
| 9,259,234 B2 | 2/2016 | Robertson et al. |
| 9,259,265 B2 | 2/2016 | Harris et al. |
| 9,265,567 B2 | 2/2016 | Orban, III et al. |
| 9,265,571 B2 | 2/2016 | Twomey et al. |
| 9,265,926 B2 | 2/2016 | Strobl et al. |
| 9,271,784 B2 | 3/2016 | Evans et al. |
| 9,274,988 B2 | 3/2016 | Hsu et al. |
| 9,277,962 B2 | 3/2016 | Koss et al. |
| 9,282,974 B2 | 3/2016 | Shelton, IV |
| 9,283,027 B2 | 3/2016 | Monson et al. |
| 9,283,045 B2 | 3/2016 | Rhee et al. |
| 9,289,256 B2 | 3/2016 | Shelton, IV et al. |
| 9,295,514 B2 | 3/2016 | Shelton, IV et al. |
| 9,308,014 B2 | 4/2016 | Fischer |
| 9,314,292 B2 | 4/2016 | Trees et al. |
| 9,326,788 B2 | 5/2016 | Batross et al. |
| 9,326,812 B2 | 5/2016 | Waaler et al. |
| 9,333,025 B2 | 5/2016 | Monson et al. |
| 9,339,323 B2 | 5/2016 | Eder et al. |
| 9,339,326 B2 | 5/2016 | McCullagh et al. |
| 9,344,042 B2 | 5/2016 | Mao |
| 9,345,481 B2 | 5/2016 | Hall et al. |
| 9,345,900 B2 | 5/2016 | Wu et al. |
| 9,351,754 B2 | 5/2016 | Vakharia et al. |
| 9,358,061 B2 | 6/2016 | Plascencia, Jr. et al. |
| 9,358,065 B2 | 6/2016 | Ladtkow et al. |
| 9,364,225 B2 | 6/2016 | Sniffin et al. |
| 9,364,230 B2 | 6/2016 | Shelton, IV et al. |
| 9,375,232 B2 | 6/2016 | Hunt et al. |
| 9,375,256 B2 | 6/2016 | Cunningham et al. |
| 9,375,267 B2 | 6/2016 | Kerr et al. |
| 9,381,060 B2 | 7/2016 | Artale et al. |
| 9,386,983 B2 | 7/2016 | Swensgard et al. |
| 9,393,037 B2 | 7/2016 | Olson et al. |
| 9,402,682 B2 | 8/2016 | Worrell et al. |
| 9,408,606 B2 | 8/2016 | Shelton, IV |
| 9,408,622 B2 | 8/2016 | Stulen et al. |
| 9,408,660 B2 | 8/2016 | Strobl et al. |
| 9,414,880 B2 | 8/2016 | Monson et al. |
| 9,421,060 B2 | 8/2016 | Monson et al. |
| 9,456,863 B2 | 10/2016 | Moua |
| 9,456,864 B2 | 10/2016 | Witt et al. |
| 9,456,876 B2 | 10/2016 | Hagn |
| 9,468,490 B2 | 10/2016 | Twomey et al. |
| 9,492,224 B2 | 11/2016 | Boudreaux et al. |
| 9,504,524 B2 | 11/2016 | Behnke, II |
| 9,510,906 B2 | 12/2016 | Boudreaux et al. |
| 9,522,029 B2 | 12/2016 | Yates et al. |
| 9,526,564 B2 | 12/2016 | Rusin |
| 9,526,565 B2 | 12/2016 | Strobl |
| 9,549,663 B2 | 1/2017 | Larkin |
| 9,554,845 B2 | 1/2017 | Arts |
| 9,554,846 B2 | 1/2017 | Boudreaux |
| 9,554,854 B2 | 1/2017 | Yates et al. |
| 9,561,038 B2 | 2/2017 | Shelton, IV et al. |
| 9,585,709 B2 | 3/2017 | Krapohl |
| 9,597,143 B2 | 3/2017 | Madan et al. |
| 9,610,091 B2 | 4/2017 | Johnson et al. |
| 9,610,114 B2 | 4/2017 | Baxter, III et al. |
| 9,615,877 B2 | 4/2017 | Tyrrell et al. |
| 9,622,810 B2 | 4/2017 | Hart et al. |
| 9,627,120 B2 | 4/2017 | Scott et al. |
| 9,629,629 B2 | 4/2017 | Leimbach et al. |
| 9,642,669 B2 | 5/2017 | Takashino et al. |
| 9,649,111 B2 | 5/2017 | Shelton, IV et al. |
| 9,649,144 B2 | 5/2017 | Aluru et al. |
| 9,649,151 B2 | 5/2017 | Goodman et al. |
| 9,662,131 B2 | 5/2017 | Omori et al. |

(56) References Cited

U.S. PATENT DOCUMENTS

| | | |
|---|---|---|
| 9,668,806 B2 | 6/2017 | Unger et al. |
| 9,687,295 B2 | 6/2017 | Joseph |
| 9,700,339 B2 | 7/2017 | Nield |
| 9,707,005 B2 | 7/2017 | Strobl et al. |
| 9,707,027 B2 | 7/2017 | Ruddenklau et al. |
| 9,707,030 B2 | 7/2017 | Davison et al. |
| 9,713,491 B2 | 7/2017 | Roy et al. |
| 9,724,118 B2 | 8/2017 | Schulte et al. |
| 9,724,152 B2 | 8/2017 | Horlle et al. |
| 9,737,355 B2 | 8/2017 | Yates et al. |
| 9,737,358 B2 | 8/2017 | Beckman et al. |
| 9,743,929 B2 | 8/2017 | Leimbach et al. |
| 9,757,128 B2 | 9/2017 | Baber et al. |
| 9,757,142 B2 | 9/2017 | Shimizu |
| 9,757,186 B2 | 9/2017 | Boudreaux et al. |
| 9,775,669 B2 | 10/2017 | Marczyk et al. |
| 9,782,214 B2 | 10/2017 | Houser et al. |
| 9,782,220 B2 | 10/2017 | Mark et al. |
| 9,788,891 B2 | 10/2017 | Christian et al. |
| 9,795,436 B2 | 10/2017 | Yates et al. |
| 9,802,033 B2 | 10/2017 | Hibner et al. |
| 9,808,244 B2 | 11/2017 | Leimbach et al. |
| 9,808,308 B2 | 11/2017 | Faller et al. |
| 9,814,460 B2 | 11/2017 | Kimsey et al. |
| 9,814,514 B2 | 11/2017 | Shelton, IV et al. |
| 9,820,768 B2 | 11/2017 | Gee et al. |
| 9,820,771 B2 | 11/2017 | Norton et al. |
| 9,833,239 B2 | 12/2017 | Yates et al. |
| 9,848,937 B2 | 12/2017 | Trees et al. |
| 9,848,939 B2 | 12/2017 | Mayer et al. |
| 9,861,428 B2 | 1/2018 | Trees et al. |
| 9,872,725 B2 | 1/2018 | Worrell et al. |
| 9,877,720 B2 | 1/2018 | Worrell et al. |
| 9,877,776 B2 | 1/2018 | Boudreaux |
| 9,877,782 B2 | 1/2018 | Voegele et al. |
| 9,888,954 B2 * | 2/2018 | Van Wyk ............. A61B 18/149 |
| 9,888,958 B2 | 2/2018 | Evans et al. |
| 9,901,390 B2 | 2/2018 | Allen, IV et al. |
| 9,901,754 B2 | 2/2018 | Yamada |
| 9,907,563 B2 | 3/2018 | Germain et al. |
| 9,913,680 B2 | 3/2018 | Voegele et al. |
| 9,918,730 B2 | 3/2018 | Trees et al. |
| 9,931,157 B2 | 4/2018 | Strobl et al. |
| 9,937,001 B2 | 4/2018 | Nakamura |
| 9,943,357 B2 | 4/2018 | Cunningham et al. |
| 9,949,620 B2 | 4/2018 | Duval et al. |
| 9,949,785 B2 | 4/2018 | Price et al. |
| 9,949,788 B2 | 4/2018 | Boudreaux |
| 9,974,539 B2 | 5/2018 | Yates et al. |
| 9,993,289 B2 | 6/2018 | Sobajima et al. |
| 10,010,339 B2 | 7/2018 | Witt et al. |
| 10,016,207 B2 | 7/2018 | Suzuki et al. |
| 10,022,142 B2 | 7/2018 | Aranyi et al. |
| 10,034,707 B2 | 7/2018 | Papaioannou et al. |
| 10,041,822 B2 | 8/2018 | Zemlok |
| 10,052,044 B2 | 8/2018 | Shelton, IV et al. |
| 10,058,376 B2 | 8/2018 | Horner et al. |
| 10,070,916 B2 | 9/2018 | Artale |
| 10,080,606 B2 | 9/2018 | Kappus et al. |
| 10,092,310 B2 | 10/2018 | Boudreaux et al. |
| 10,092,348 B2 | 10/2018 | Boudreaux |
| 10,092,350 B2 | 10/2018 | Rothweiler et al. |
| 10,105,174 B2 | 10/2018 | Krapohl |
| 10,111,699 B2 | 10/2018 | Boudreaux |
| 10,117,702 B2 | 11/2018 | Danziger et al. |
| 10,130,410 B2 | 11/2018 | Strobl et al. |
| 10,130,414 B2 | 11/2018 | Weiler et al. |
| 10,135,242 B2 | 11/2018 | Baber et al. |
| 10,159,524 B2 | 12/2018 | Yates et al. |
| 10,166,060 B2 | 1/2019 | Johnson et al. |
| 10,172,669 B2 | 1/2019 | Felder et al. |
| 10,194,911 B2 | 2/2019 | Miller et al. |
| 10,194,972 B2 | 2/2019 | Yates et al. |
| 10,194,976 B2 | 2/2019 | Boudreaux |
| 10,194,977 B2 | 2/2019 | Yang |
| 10,211,586 B2 | 2/2019 | Adams et al. |
| 10,231,776 B2 | 3/2019 | Artale et al. |
| 10,238,387 B2 | 3/2019 | Yates et al. |
| 10,245,095 B2 | 4/2019 | Boudreaux |
| 10,258,404 B2 | 4/2019 | Wang |
| 10,265,118 B2 | 4/2019 | Gerhardt |
| 10,278,721 B2 | 5/2019 | Dietz et al. |
| 10,307,203 B2 | 6/2019 | Wyatt |
| 10,314,638 B2 | 6/2019 | Gee et al. |
| 10,321,950 B2 | 6/2019 | Yates et al. |
| 10,342,602 B2 | 7/2019 | Strobl et al. |
| 10,413,352 B2 | 9/2019 | Thomas et al. |
| 10,420,601 B2 | 9/2019 | Marion et al. |
| 10,420,607 B2 | 9/2019 | Woloszko et al. |
| 10,433,900 B2 | 10/2019 | Harris et al. |
| 10,441,345 B2 | 10/2019 | Aldridge et al. |
| 10,463,421 B2 | 11/2019 | Boudreaux et al. |
| 10,478,243 B2 | 11/2019 | Couture et al. |
| 10,485,607 B2 | 11/2019 | Strobl et al. |
| 10,524,852 B1 | 1/2020 | Cagle et al. |
| 10,524,854 B2 | 1/2020 | Woodruff et al. |
| 10,575,868 B2 | 3/2020 | Hall et al. |
| 2001/0025184 A1 | 9/2001 | Messerly |
| 2001/0031950 A1 | 10/2001 | Ryan |
| 2001/0039419 A1 | 11/2001 | Francischelli et al. |
| 2002/0002377 A1 | 1/2002 | Cimino |
| 2002/0019649 A1 | 2/2002 | Sikora et al. |
| 2002/0022836 A1 | 2/2002 | Goble et al. |
| 2002/0049551 A1 | 4/2002 | Friedman et al. |
| 2002/0077550 A1 | 6/2002 | Rabiner et al. |
| 2002/0095175 A1 | 7/2002 | Brock et al. |
| 2002/0107517 A1 | 8/2002 | Witt et al. |
| 2002/0133149 A1 | 9/2002 | Bessette |
| 2002/0156493 A1 | 10/2002 | Houser et al. |
| 2003/0014053 A1 | 1/2003 | Nguyen et al. |
| 2003/0055443 A1 | 3/2003 | Spotnitz |
| 2003/0066938 A1 | 4/2003 | Zimmerman |
| 2003/0109875 A1 | 6/2003 | Tetzlaff et al. |
| 2003/0114731 A1 | 6/2003 | Cadeddu et al. |
| 2003/0114851 A1 | 6/2003 | Truckai et al. |
| 2003/0130693 A1 | 7/2003 | Levin et al. |
| 2003/0139741 A1 | 7/2003 | Goble et al. |
| 2003/0158548 A1 | 8/2003 | Phan et al. |
| 2003/0171747 A1 | 9/2003 | Kanehira et al. |
| 2003/0181910 A1 | 9/2003 | Dycus et al. |
| 2003/0204199 A1 | 10/2003 | Novak et al. |
| 2003/0212332 A1 | 11/2003 | Fenton et al. |
| 2003/0229344 A1 | 12/2003 | Dycus et al. |
| 2004/0030254 A1 | 2/2004 | Babaev |
| 2004/0047485 A1 | 3/2004 | Sherrit et al. |
| 2004/0054364 A1 | 3/2004 | Aranyi et al. |
| 2004/0092921 A1 | 5/2004 | Kadziauskas et al. |
| 2004/0092992 A1 | 5/2004 | Adams et al. |
| 2004/0093039 A1 | 5/2004 | Schumert |
| 2004/0097919 A1 | 5/2004 | Wellman et al. |
| 2004/0097996 A1 | 5/2004 | Rabiner et al. |
| 2004/0102804 A1 | 5/2004 | Chin |
| 2004/0133089 A1 | 7/2004 | Kilcoyne et al. |
| 2004/0138621 A1 | 7/2004 | Jahns et al. |
| 2004/0167508 A1 | 8/2004 | Wham et al. |
| 2004/0193150 A1 | 9/2004 | Sharkey et al. |
| 2004/0199193 A1 | 10/2004 | Hayashi et al. |
| 2004/0249367 A1 | 12/2004 | Saadat et al. |
| 2004/0249374 A1 | 12/2004 | Tetzlaff et al. |
| 2004/0260273 A1 | 12/2004 | Wan |
| 2004/0260300 A1 | 12/2004 | Gorensek et al. |
| 2005/0015125 A1 | 1/2005 | Mioduski et al. |
| 2005/0033278 A1 | 2/2005 | McClurken et al. |
| 2005/0033337 A1 | 2/2005 | Muir et al. |
| 2005/0090817 A1 | 4/2005 | Phan |
| 2005/0096502 A1 | 5/2005 | Khalili |
| 2005/0119640 A1 | 6/2005 | Sverduk et al. |
| 2005/0131390 A1 | 6/2005 | Heinrich et al. |
| 2005/0143769 A1 | 6/2005 | White et al. |
| 2005/0149108 A1 | 7/2005 | Cox |
| 2005/0165429 A1 | 7/2005 | Douglas et al. |
| 2005/0171522 A1 | 8/2005 | Christopherson |
| 2005/0177184 A1 | 8/2005 | Easley |
| 2005/0192610 A1 | 9/2005 | Houser et al. |

(56) References Cited

U.S. PATENT DOCUMENTS

| | | |
|---|---|---|
| 2005/0215858 A1 | 9/2005 | Vail |
| 2005/0256405 A1 | 11/2005 | Makin et al. |
| 2005/0261588 A1 | 11/2005 | Makin et al. |
| 2005/0267464 A1 | 12/2005 | Truckai et al. |
| 2005/0272972 A1 | 12/2005 | Iddan |
| 2005/0273139 A1 | 12/2005 | Krauss et al. |
| 2005/0288555 A1 | 12/2005 | Binmoeller |
| 2005/0288659 A1 | 12/2005 | Kimura et al. |
| 2006/0030797 A1 | 2/2006 | Zhou et al. |
| 2006/0058825 A1 | 3/2006 | Ogura et al. |
| 2006/0063130 A1 | 3/2006 | Hayman et al. |
| 2006/0064086 A1 | 3/2006 | Odom |
| 2006/0159731 A1 | 7/2006 | Shoshan |
| 2006/0190034 A1 | 8/2006 | Nishizawa et al. |
| 2006/0211943 A1 | 9/2006 | Beaupre |
| 2006/0253050 A1 | 11/2006 | Yoshimine et al. |
| 2006/0270916 A1 | 11/2006 | Skwarek et al. |
| 2006/0293656 A1 | 12/2006 | Shadduck et al. |
| 2007/0008744 A1 | 1/2007 | Heo et al. |
| 2007/0010709 A1 | 1/2007 | Reinschke |
| 2007/0016235 A1 | 1/2007 | Tanaka et al. |
| 2007/0016236 A1 | 1/2007 | Beaupre |
| 2007/0020065 A1 | 1/2007 | Kirby |
| 2007/0032701 A1 | 2/2007 | Fowler et al. |
| 2007/0032704 A1 | 2/2007 | Gandini et al. |
| 2007/0032785 A1 | 2/2007 | Diederich et al. |
| 2007/0051766 A1 | 3/2007 | Spencer |
| 2007/0055228 A1 | 3/2007 | Berg et al. |
| 2007/0063618 A1 | 3/2007 | Bromfield |
| 2007/0073185 A1 | 3/2007 | Nakao |
| 2007/0073341 A1 | 3/2007 | Smith et al. |
| 2007/0106317 A1 | 5/2007 | Shelton et al. |
| 2007/0118115 A1 | 5/2007 | Artale et al. |
| 2007/0123748 A1 | 5/2007 | Meglan |
| 2007/0130771 A1 | 6/2007 | Ehlert et al. |
| 2007/0135686 A1 | 6/2007 | Pruitt et al. |
| 2007/0149881 A1 | 6/2007 | Rabin |
| 2007/0173803 A1 | 7/2007 | Wham et al. |
| 2007/0173813 A1 | 7/2007 | Odom |
| 2007/0173872 A1 | 7/2007 | Neuenfeldt |
| 2007/0182842 A1 | 8/2007 | Sonnenschein et al. |
| 2007/0185474 A1 | 8/2007 | Nahen |
| 2007/0191713 A1 | 8/2007 | Eichmann et al. |
| 2007/0203483 A1 | 8/2007 | Kim et al. |
| 2007/0208340 A1 | 9/2007 | Ganz et al. |
| 2007/0219481 A1 | 9/2007 | Babaev |
| 2007/0232926 A1 | 10/2007 | Stulen et al. |
| 2007/0232928 A1 | 10/2007 | Wiener et al. |
| 2007/0236213 A1 | 10/2007 | Paden et al. |
| 2007/0249941 A1 | 10/2007 | Salehi et al. |
| 2007/0260242 A1 | 11/2007 | Dycus et al. |
| 2007/0265560 A1 | 11/2007 | Soltani et al. |
| 2007/0265613 A1 | 11/2007 | Edelstein et al. |
| 2007/0265616 A1 | 11/2007 | Couture et al. |
| 2007/0270651 A1 | 11/2007 | Gilad et al. |
| 2007/0275348 A1 | 11/2007 | Lemon |
| 2007/0276424 A1 | 11/2007 | Mikkaichi et al. |
| 2007/0287933 A1 | 12/2007 | Phan et al. |
| 2008/0015413 A1 | 1/2008 | Barlow et al. |
| 2008/0015575 A1 | 1/2008 | Odom et al. |
| 2008/0058775 A1 | 3/2008 | Darian et al. |
| 2008/0058845 A1 | 3/2008 | Shimizu et al. |
| 2008/0071269 A1 | 3/2008 | Hilario et al. |
| 2008/0077129 A1* | 3/2008 | Van Wyk ............ A61B 18/149 606/46 |
| 2008/0082039 A1 | 4/2008 | Babaev |
| 2008/0082098 A1 | 4/2008 | Tanaka et al. |
| 2008/0103495 A1 | 5/2008 | Mihori et al. |
| 2008/0114355 A1 | 5/2008 | Whayne et al. |
| 2008/0147058 A1 | 6/2008 | Horrell et al. |
| 2008/0147062 A1 | 6/2008 | Truckai et al. |
| 2008/0171938 A1 | 7/2008 | Masuda et al. |
| 2008/0177268 A1 | 7/2008 | Daum et al. |
| 2008/0188755 A1 | 8/2008 | Hart |
| 2008/0200940 A1 | 8/2008 | Eichmann et al. |
| 2008/0208231 A1 | 8/2008 | Ota et al. |
| 2008/0214967 A1 | 9/2008 | Aranyi et al. |
| 2008/0228179 A1 | 9/2008 | Eder et al. |
| 2008/0234709 A1 | 9/2008 | Houser |
| 2008/0281200 A1 | 11/2008 | Voic et al. |
| 2008/0281315 A1 | 11/2008 | Gines |
| 2008/0287948 A1 | 11/2008 | Newton et al. |
| 2008/0300588 A1 | 12/2008 | Groth et al. |
| 2008/0312502 A1 | 12/2008 | Swain et al. |
| 2009/0012516 A1 | 1/2009 | Curtis et al. |
| 2009/0048589 A1 | 2/2009 | Takashino et al. |
| 2009/0076506 A1 | 3/2009 | Baker |
| 2009/0082716 A1 | 3/2009 | Akahoshi |
| 2009/0082766 A1 | 3/2009 | Unger et al. |
| 2009/0143678 A1 | 6/2009 | Keast et al. |
| 2009/0182322 A1 | 7/2009 | D'Amelio et al. |
| 2009/0182331 A1 | 7/2009 | D'Amelio et al. |
| 2009/0182332 A1 | 7/2009 | Long et al. |
| 2009/0248021 A1 | 10/2009 | McKenna |
| 2009/0254080 A1 | 10/2009 | Honda |
| 2009/0264879 A1* | 10/2009 | McClurken ......... A61B 18/1206 606/33 |
| 2009/0270771 A1 | 10/2009 | Takahashi |
| 2009/0270853 A1 | 10/2009 | Yachi et al. |
| 2009/0287205 A1 | 11/2009 | Ingle |
| 2010/0022824 A1* | 1/2010 | Cybulski ............... A61B 1/051 600/104 |
| 2010/0036370 A1 | 2/2010 | Mirel et al. |
| 2010/0081863 A1 | 4/2010 | Hess et al. |
| 2010/0081864 A1 | 4/2010 | Hess et al. |
| 2010/0081883 A1 | 4/2010 | Murray et al. |
| 2010/0094323 A1 | 4/2010 | Isaacs et al. |
| 2010/0158307 A1 | 6/2010 | Kubota et al. |
| 2010/0187283 A1 | 7/2010 | Crainich et al. |
| 2010/0204802 A1 | 8/2010 | Wilson et al. |
| 2010/0222752 A1 | 9/2010 | Collins, Jr. et al. |
| 2010/0274278 A1 | 10/2010 | Fleenor et al. |
| 2010/0280368 A1 | 11/2010 | Can et al. |
| 2010/0298743 A1 | 11/2010 | Nield et al. |
| 2011/0009857 A1 | 1/2011 | Subramaniam et al. |
| 2011/0028964 A1 | 2/2011 | Edwards |
| 2011/0087224 A1 | 4/2011 | Cadeddu et al. |
| 2011/0118601 A1* | 5/2011 | Barnes ................. A61M 1/0058 600/439 |
| 2011/0125151 A1 | 5/2011 | Strauss et al. |
| 2011/0257680 A1 | 10/2011 | Reschke et al. |
| 2011/0270245 A1 | 11/2011 | Horner et al. |
| 2011/0278343 A1 | 11/2011 | Knodel et al. |
| 2011/0284014 A1 | 11/2011 | Cadeddu et al. |
| 2011/0290856 A1 | 12/2011 | Shelton, IV et al. |
| 2011/0295295 A1 | 12/2011 | Shelton, IV et al. |
| 2011/0306967 A1 | 12/2011 | Payne et al. |
| 2011/0313415 A1 | 12/2011 | Fernandez et al. |
| 2012/0016413 A1 | 1/2012 | Timm et al. |
| 2012/0022519 A1 | 1/2012 | Huang et al. |
| 2012/0022526 A1 | 1/2012 | Aldridge et al. |
| 2012/0041358 A1 | 2/2012 | Mann et al. |
| 2012/0078244 A1 | 3/2012 | Worrell et al. |
| 2012/0085358 A1 | 4/2012 | Cadeddu et al. |
| 2012/0109186 A1 | 5/2012 | Parrott et al. |
| 2012/0116222 A1 | 5/2012 | Sawada et al. |
| 2012/0116265 A1 | 5/2012 | Houser et al. |
| 2012/0265241 A1 | 10/2012 | Hart et al. |
| 2012/0296371 A1 | 11/2012 | Kappus et al. |
| 2013/0023925 A1 | 1/2013 | Mueller |
| 2013/0035685 A1 | 2/2013 | Fischer et al. |
| 2013/0123776 A1 | 5/2013 | Monson et al. |
| 2013/0158659 A1 | 6/2013 | Bergs et al. |
| 2013/0158660 A1 | 6/2013 | Bergs et al. |
| 2013/0253256 A1 | 9/2013 | Griffith et al. |
| 2013/0296843 A1 | 11/2013 | Boudreaux et al. |
| 2014/0001231 A1 | 1/2014 | Shelton, IV et al. |
| 2014/0001234 A1 | 1/2014 | Shelton, IV et al. |
| 2014/0005640 A1 | 1/2014 | Shelton, IV et al. |
| 2014/0005678 A1 | 1/2014 | Shelton, IV et al. |
| 2014/0005702 A1 | 1/2014 | Timm et al. |
| 2014/0005705 A1 | 1/2014 | Weir et al. |
| 2014/0005718 A1 | 1/2014 | Shelton, IV et al. |
| 2014/0014544 A1 | 1/2014 | Bugnard et al. |

(56) References Cited

U.S. PATENT DOCUMENTS

| | | | |
|---|---|---|---|
| 2014/0194864 A1 | 7/2014 | Martin et al. | |
| 2014/0194874 A1 | 7/2014 | Dietz et al. | |
| 2014/0194875 A1 | 7/2014 | Reschke et al. | |
| 2014/0207135 A1 | 7/2014 | Winter | |
| 2014/0257269 A1* | 9/2014 | Woloszko | A61B 18/042 606/34 |
| 2014/0263541 A1 | 9/2014 | Leimbach et al. | |
| 2014/0263552 A1 | 9/2014 | Hall et al. | |
| 2014/0303576 A1* | 10/2014 | Schultz | A61M 1/0094 604/319 |
| 2014/0350540 A1 | 11/2014 | Kitagawa et al. | |
| 2015/0032150 A1 | 1/2015 | Ishida et al. | |
| 2015/0080876 A1 | 3/2015 | Worrell et al. | |
| 2015/0250531 A1 | 9/2015 | Dycus et al. | |
| 2015/0257819 A1 | 9/2015 | Dycus et al. | |
| 2015/0272571 A1 | 10/2015 | Leimbach et al. | |
| 2015/0272659 A1 | 10/2015 | Boudreaux et al. | |
| 2015/0327918 A1 | 11/2015 | Sobajima et al. | |
| 2016/0045248 A1 | 2/2016 | Unger et al. | |
| 2016/0051316 A1 | 2/2016 | Boudreaux | |
| 2016/0066980 A1 | 3/2016 | Schall et al. | |
| 2016/0100747 A1 | 4/2016 | Nitsan et al. | |
| 2016/0143687 A1 | 5/2016 | Hart et al. | |
| 2016/0157923 A1 | 6/2016 | Ding | |
| 2016/0157927 A1 | 6/2016 | Corbett et al. | |
| 2016/0175029 A1 | 6/2016 | Witt et al. | |
| 2016/0199124 A1 | 7/2016 | Thomas et al. | |
| 2016/0199125 A1 | 7/2016 | Jones | |
| 2016/0270842 A1 | 9/2016 | Strobl et al. | |
| 2016/0270843 A1 | 9/2016 | Boudreaux et al. | |
| 2016/0278848 A1 | 9/2016 | Boudreaux et al. | |
| 2016/0296270 A1 | 10/2016 | Strobl et al. | |
| 2016/0367307 A1* | 12/2016 | Ishikawa | A61B 18/042 |
| 2017/0056097 A1 | 3/2017 | Monson et al. | |
| 2017/0105787 A1 | 4/2017 | Witt et al. | |
| 2017/0105789 A1 | 4/2017 | Boudreaux et al. | |
| 2017/0135751 A1 | 5/2017 | Rothweiler et al. | |
| 2017/0164972 A1 | 6/2017 | Johnson et al. | |
| 2017/0189102 A1 | 7/2017 | Hibner et al. | |
| 2017/0312014 A1 | 11/2017 | Strobl et al. | |
| 2017/0312015 A1 | 11/2017 | Worrell et al. | |
| 2017/0312017 A1 | 11/2017 | Trees et al. | |
| 2017/0312018 A1 | 11/2017 | Trees et al. | |
| 2017/0312019 A1 | 11/2017 | Trees et al. | |
| 2017/0325878 A1* | 11/2017 | Messerly | A61B 18/1206 |
| 2017/0325886 A1 | 11/2017 | Graham et al. | |
| 2017/0367751 A1 | 12/2017 | Ruddenklau et al. | |
| 2018/0085156 A1 | 3/2018 | Witt et al. | |
| 2018/0125571 A1 | 5/2018 | Witt et al. | |
| 2018/0228530 A1 | 8/2018 | Yates et al. | |
| 2018/0263683 A1 | 9/2018 | Renner et al. | |
| 2018/0280075 A1 | 10/2018 | Nott et al. | |
| 2018/0368906 A1 | 12/2018 | Yates et al. | |
| 2019/0000468 A1 | 1/2019 | Adams et al. | |
| 2019/0000470 A1 | 1/2019 | Yates et al. | |
| 2019/0000528 A1 | 1/2019 | Yates et al. | |
| 2019/0000530 A1 | 1/2019 | Yates et al. | |
| 2019/0000555 A1 | 1/2019 | Schings et al. | |
| 2019/0059979 A1* | 2/2019 | Shelton, IV | A61M 1/0031 |
| 2019/0059980 A1* | 2/2019 | Shelton, IV | A61B 18/14 |
| 2019/0099209 A1* | 4/2019 | Witt | A61B 18/1402 |
| 2019/0099212 A1 | 4/2019 | Davison et al. | |
| 2019/0099217 A1 | 4/2019 | Witt et al. | |
| 2020/0375651 A1 | 12/2020 | Witt et al. | |

FOREIGN PATENT DOCUMENTS

| | | |
|---|---|---|
| CN | 2868227 Y | 2/2007 |
| DE | 4300307 A1 | 7/1994 |
| DE | 29623113 U1 | 10/1997 |
| DE | 20004812 U1 | 9/2000 |
| DE | 10201569 A1 | 7/2003 |
| DE | 102005032371 A1 | 1/2007 |
| EP | 0171967 A2 | 2/1986 |
| EP | 0705571 A1 | 4/1996 |
| EP | 1862133 A1 | 12/2007 |
| EP | 2060238 A1 | 5/2009 |
| EP | 1747761 B1 | 10/2009 |
| EP | 1767164 B1 | 1/2013 |
| EP | 2578172 A2 | 4/2013 |
| ES | 2419159 A2 | 8/2013 |
| GB | 2032221 A | 4/1980 |
| JP | S537994 A | 1/1978 |
| JP | h08229050 A | 9/1996 |
| JP | 2002186627 A | 7/2002 |
| JP | 2009213878 A | 9/2009 |
| JP | 2010057926 A | 3/2010 |
| WO | WO-8103272 A1 | 11/1981 |
| WO | WO-9314708 A1 | 8/1993 |
| WO | WO-9800069 A1 | 1/1998 |
| WO | WO-9923960 A1 | 5/1999 |
| WO | WO-0024330 A1 | 5/2000 |
| WO | WO-0128444 A1 | 4/2001 |
| WO | WO-02080794 A1 | 10/2002 |
| WO | WO-2004078051 A2 | 9/2004 |
| WO | WO-2008130793 A1 | 10/2008 |
| WO | WO-2009067649 A2 | 5/2009 |
| WO | WO-2010104755 A1 | 9/2010 |
| WO | WO-2011008672 A2 | 1/2011 |
| WO | WO-2011044343 A2 | 4/2011 |
| WO | WO-2011144911 A1 | 11/2011 |
| WO | WO-2012044606 A2 | 4/2012 |
| WO | WO-2012061638 A1 | 5/2012 |
| WO | WO-2013131823 A1 | 9/2013 |

OTHER PUBLICATIONS

Henriques. F.C., "Studies in thermal injury V. The predictability and the significance of thermally induced rate processes leading to irreversible epidermal injury." Archives of Pathology, 434, pp. 489-502 (1947).

Arnoczky et al., "Thermal Modification of Conective Tissues: Basic Science Considerations and Clinical Implications," J. Am Acad Orthop Surg, vol. 8, No. 5, pp. 305-313 (Sep./Oct. 2000).

Chen et al., "Heat-Induced Changes in the Mechanics of a Collagenous Tissue: Isothermal Free Shrinkage," Transactions of the ASME, vol. 119, pp. 372-378 (Nov. 1997).

Chen et al., "Heat-Induced Changes in the Mechanics of a Collagenous Tissue: Isothermal, Isotonic Shrinkage," Transactions of the ASME, vol. 120, pp. 382-388 (Jun. 1998).

Chen et al., "Phenomenological Evolution Equations for Heat-Induced Shrinkage of a Collagenous Tissue," IEEE Transactions on Biomedical Engineering, vol. 45, No. 10, pp. 1234-1240 (Oct. 1998).

Harris et al., "Kinetics of Thermal Damage to a Collagenous Membrane Under Biaxial Isotonic Loading," IEEE Transactions on Biomedical Engineering, vol. 51, No. 2, pp. 371-379 (Feb. 2004).

Harris et al., "Altered Mechanical Behavior of Epicardium Due to Isothermal Heating Under Biaxial Isotonic Loads," Journal of Biomechanical Engineering, vol. 125, pp. 381-388 (Jun. 2003).

Lee et al., "A multi-sample denaturation temperature tester for collagenous biomaterials," Med. Eng. Phy., vol. 17, No. 2, pp. 115-121 (Mar. 1995).

Moran et al., "Thermally Induced Shrinkage of Joint Capsule," Clinical Orthopaedics and Related Research, No. 281, pp. 248-255 (Dec. 2000).

Wall et al., "Thermal modification of collagen," J Shoulder Elbow Surg, No. 8, pp. 339-344 (Jul./Aug. 1999).

Wells et al., "Altered Mechanical Behavior of Epicardium Under Isothermal Biaxial Loading," Transactions of the ASME, Journal of Biomedical Engineering, vol. 126, pp. 492-497 (Aug. 2004).

Gibson, "Magnetic Refrigerator Successfully Tested," U.S. Department of Energy Research News, accessed online on Aug. 6, 2010 at http://www.eurekaletorg/features/doe/2001-11/dl-mrs062802.php (Nov. 1, 2001).

Humphrey, J.D., "Continuum Thermomechanics and the Clinical Treatment of Disease and Injury," Appl. Mech. Rev., vol. 56, No. 2 pp. 231-260 (Mar. 2003).

(56) References Cited

OTHER PUBLICATIONS

National Semiconductors Temperature Sensor Handbook—http://www.national.com/appinfo/tempsensors/files/temphb.pdf; accessed online: Apr. 1, 2011.
Chen et al., "Heat-induced changes in the mechanics of a collagenous tissue: pseudoelastic behavior at 37° C.," Journal of Biomechanics, 31, pp. 211-216 (1998).
Kurt Gieck & Reiner Gieck, *Engineering Formulas* § Z.7 (7th ed. 1997).
Hayashi et al., "The Effect of Thermal Heating on the Length and Histologic Properties of the Glenohumeral Joint Capsule," American Journal of Sports Medicine, vol. 25, Issue 1, 11 pages (Jan. 1997), URL: http://www.mdconsult.com/das/article/body/156183648-2/jorg=journal&source=MI&sp=1 . . . , accessed Aug. 25, 2009.
Abbott, et al. Proceedings of the 2007 IEEEIRDJ International Conference on Intelligent Robots and Systems. 410-416, 2007.
Cadeddu et al., "Magnetic positioning system for trocarless laparoscopic instruments," American College of Surgeons Poster, 2004.
Cadeddu et al., "Novel magnetically guided intra-abdominal camera to facilitate laparoendoscopic single site surgery: initial human experience," Surgical Endoscopy, SAGES Oral Manuscript, 2009.
Cadeddu et al., "Transabdominal magnetic anchoring system for trocar-less laparoscopic surgery," American Urological Association Poster, 2002.
Cadeddu et al., "Transabdominal magnetic anchoring system for trocar-less laparoscopic surgery," Journal of Urology Abstract, 2002.
Castellvi et al., "Completely transvaginal NOTES cholecystectomy in a porcine model using novel endoscopic instrumentation," Accepted for Poster Presentation, SAGES Annual Meeting, 2009.
Castellvi et al., "Hybrid transgastric NOTES cholecystectomy in a porcine model using a magnetically anchored cautery and novel instrumentation," Submitted for Presentation, ASGE, 2009.
Castellvi et al., "Hybrid transvaginal NOTES sleeve gastrectomy in a porcine model using a magnetically anchored camera and novel instrumentation," Accepted for Poster Presentation, SAGES Annual Meeting, 2009.
Duchene et al., "Magnetic positioning system for trocarless laparoscopic instruments," Engineering and Urology Society Poster, 2004.
Fernandez et al., "Development of a transabdominal anchoring system for trocar-less laparoscopic surgery," ASME Proceedings of/MECE, 2003.
Gedeon et al., "Maximizing coupling strength of magnetically anchored notes instruments: How thick can we go?" Submittedfor Presentation, Poster, SAGES Annual Meeting, 2008.
Gedeon et al., "Maximizing coupling strength of magnetically anchored notes instruments: How thick can we go?" SAGES Annual Meeting Poster, 2008.
Park et al., "Trocar-less Instrumentation for Laparoscopy: Magnetic Positioning of Intra-Abdominal Camera and Retractor", Annals of Surgery, vol. 245, No. 3, pp. 379-384, Mar. 2007.
Peirs et al., "A miniature manipulator for integration in self-propelling endoscope," Sensors and Actuators, 92:343-9, 2001.
Raman et al., "Complete transvaginal NOTES nephrectomy using magnetically anchored instrumentation," Journal of Endourology, 23(3):, 2009.367-371,2009.
Rapaccini et al., "Gastric Wall Thickness in Normal and Neoplastic Subjects: A Prospective Study Performed by Abdominal Ultrasound", Gastrointestinal Radiology, vol. 13, pp. 197-199. 1988.
Scott et al., "A randomized comparison of laparoscopic, flexible endoscopic, and wired and wireless magnetic NOTES cameras on ex-vivo and in-vivo surgical performance," Digestive Disease Week (DDW), American Society for Gastrointestinal Endoscopy (ASGE) Annual Meeting Abstract, 2008.
Scott et al., "Completely transvaginal NOTES cholecystectomy using magnetically anchored instruments," Surg. Endosc., 21:2308-2316, 2007.
Scott et al., "Evaluation of a novel air seal access port for transvaginal notes cholecystectomy," Submitted for Presentation, SAGES Annual Meeting, 2008.
Scott et al., "Magnetically anchored instruments for transgastric endoscopic surgery," Oral Presentation for SAGES Annual Meeting, Emerging Technology Oral Abstract ET005, 2006.
Scott et al., "Optimizing magnetically anchored camera, light source, graspers, and cautery dissector for transvaginal notes cholecystectomy," Submitted for Presentation, SAGES Annual Meeting, 2008.
Scott et al., "Short-term survival outcomes following transvaginal NOTES cholecystectomy using magnetically anchored instruments," Oral Presentation, ASGE Annual Meeting/DDW, 2007.
Scott et al., "Trans gastric, transcolonic, and transvaginal cholecystectomy using magnetically anchored instruments," SAGES Annual Meeting Poster, 2007.
Scott et al., "Transvaginal NOTES cholecystectomy using magnetically anchored instruments," Abstract for Video Submission, ASGE II1h Annual Video Forum, 2007.
Scott et al., "Transvaginal single access 'pure' NOTES sleeve gastrectomy using a deployable magnetically anchored video camera," Digestive Disease Week (DDW), American Society for Gastrointestinal Endoscopy (ASGE) Annual Meeting Poster, 2008.
Swain et al., "Linear stapler formation of ileo-rectal, entero-enteral and gastrojejunal anastomoses during dual and single access 'pure' NOTES procedures: Methods, magnets and stapler modifications," Digestive Disease Week (DDW), American Society for Gastrointestinal Endoscopy (ASGE) Annual Meeting Abstract, 2008.
Swain et al., "Wireless endosurgery for NOTES," Digestive Disease Week (DDW), American Society for Gastrointestinal Endoscopy (ASGE) Annual Meeting Abstract, 2008.
Tang et al., "Live video manipulator for endoscopy and natural orifice transluminal endoscopic surgery (with videos)," Gastrointestinal Endoscopy, 68:559-564, 2008.
Zeltser et al., "Single trocar laparoscopic nephrectomy using magnetic anchoring and guidance system in the porcine model," The Journal of Urology, 178:288-291, 2007.
https://www.kjmagnetics.com/fieldcalculator.asp, retrieved Jul. 11, 2016, backdated to Nov. 11, 2011 via https://web.archive.org/web/20111116164447/http://www.kjmagnetics.com/fieldcalculator.asp.
Covidien Brochure, [Value Analysis Brief], LigaSure AdvanceTM Pistol Grip, dated Rev. Apr. 2010 (7 pages).
Covidien Brochure, LigaSure Impact™ Instrument LF4318, dated Feb. 2013 (3 pages).
Covidien Brochure, LigaSure Atlas™ Hand Switching Instruments, dated Dec. 2008 (2 pages).
Covidien Brochure, The LigaSure™ 5 mm Blunt Tip Sealer/Divider Family, dated Apr. 2013 (2 pages).
Covidien Brochure, The LigaSure Precise™ Instrument, dated Mar. 2011 (2 pages).
Sullivan, "Cost-Constrained Selection of Strand Diameter and Number in a Litz-Wire Transformer Winding," IEEE Transactions on Power Electronics, vol. 16, No. 2, Mar. 2001, pp. 281-288.
Sullivan, "Optimal Choice for Number of Strands in a Litz-Wire Transformer Winding," IEEE Transactions on Power Electronics, vol. 14, No. 2, Mar. 1999, pp. 283-291.
Wright, et al., "Time-Temperature Equivalence of Heat-Induced Changes in Cells and Proteins," Feb. 1998. ASME Journal of Biomechanical Engineering, vol. 120, pp. 22-26.
Douglas, S.C. "Introduction to Adaptive Filter". Digital Signal Processing Handbook. Ed. Vijay K. Madisetti and Douglas B. Williams. Boca Raton: CRC Press LLC, 1999.
Jang, J. et al. "Neuro-fuzzy and Soft Computing." Prentice Hall, 1997, pp. 13-89, 199-293, 335-393, 453-496, 535-549.
Erbe Electrosurgery VIO® 200 S, (2012), p. 7, 12 pages, accessed Mar. 31, 2014 at http://www.erbe-med. com/erbe/media/Marketing materialien/85140170 ERBE EN VIO 200 S D027541.
Leonard I. Malis, M.D., "The Value of Irrigation During Bipolar Coagulation," 1989.
AST Products, Inc., "Principles of Video Contact Angle Analysis," 20 pages, (2006).
Lim et al., "A Review of Mechanism Used in Laparoscopic Surgical Instruments," Mechanism and Machine Theory, vol. 38, pp. 1133-1147, (2003).

(56) References Cited

OTHER PUBLICATIONS

F. A. Duck, "Optical Properties of Tissue Including Ultraviolet and Infrared Radiation," pp. 43-71 in Physical Properties of Tissue (1990).
Orr et al., "Overview of Bioheat Transfer," pp. 367-384 in Optical-Thermal Response of Laser-Irradiated Tissue, A. J. Welch and M. J. C. van Gernert, eds., Plenum, New York (1995).
Campbell et al, "Thermal Imaging in Surgery," p. 19-3, in Medical Infrared Imaging, N. A. Diakides and J. D. Bronzino, Eds. (2008).
Huston et al., "Magnetic and Magnetostrictive Properties of Cube Textured Nickel for Magnetostrictive Transducer Applications," IEEE Transactions on Magnetics, vol. 9(4), pp. 636-640 (Dec. 1973).
Technology Overview, printed from www.harmonicscalpel.com, Internet site, website accessed on Jun. 13, 2007, (3 pages).
Gooch et al., "Recommended Infection-Control Practices for Dentistry, 1993," Published: May 28, 1993; [retrieved on Aug. 23, 2008]. Retrieved from the internet: URL: http//wonder.cdc.gov/wonder/prevguid/p0000191/p0000191.asp (15 pages).
Sherrit et al., "Novel Horn Designs for Ultrasonic/Sonic Cleaning Welding, Soldering, Cutting and Drilling," Proc. SPIE Smart Structures Conference, vol. 4701, Paper No. 34, San Diego, CA, pp. 353-360, Mar. 2002.
Hörmann et al., "Reversible and irreversible denaturation of collagen fibers." Biochemistry, 10, pp. 932-937 (1971).
Dean, D.A., "Electrical Impedance Spectroscopy Study of Biological Tissues," J. Electrostat, 66(3-4), Mar. 2008, pp. 165-177. Accessed Apr. 10, 2018: https://www.ncbi.nlm.nih.gov/pmc/articles/PMC2597841/.

* cited by examiner

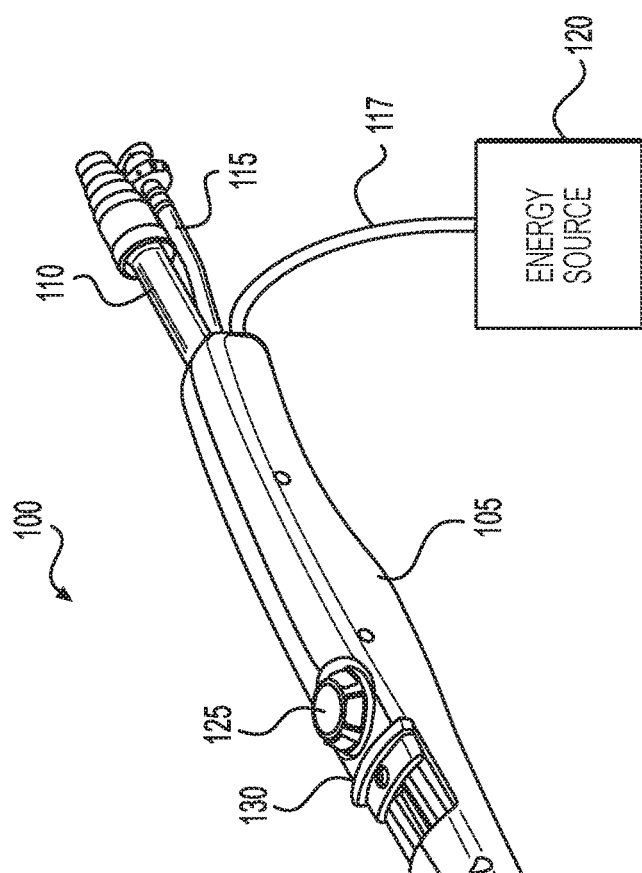
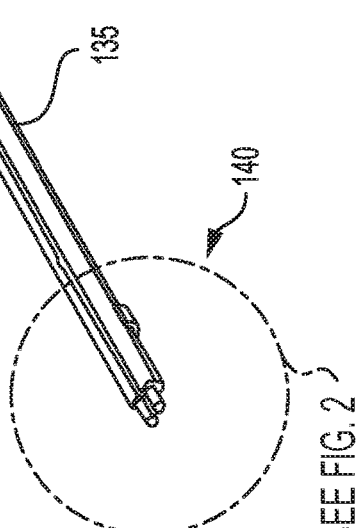
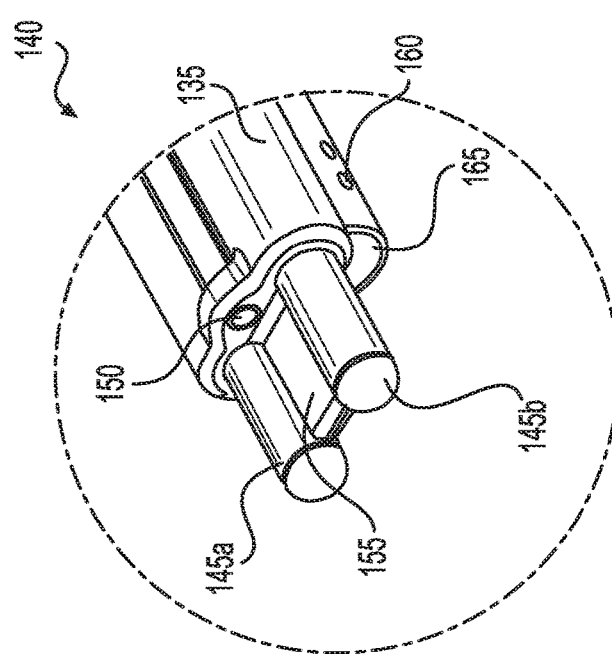
FIG. 1
FIG. 2

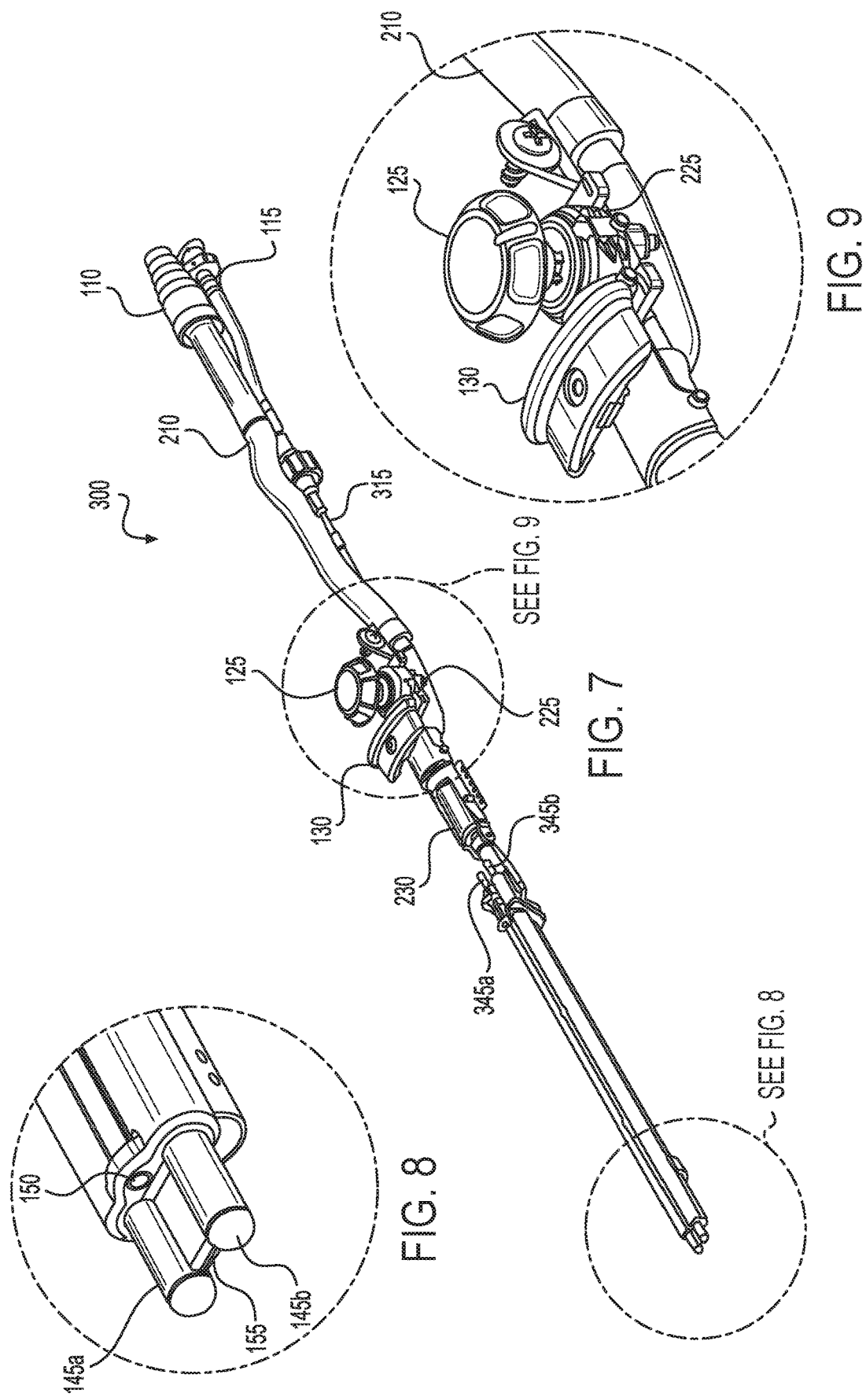

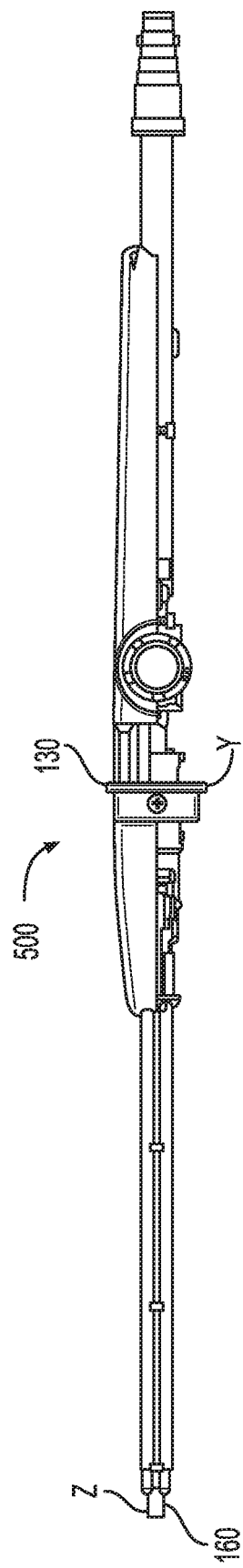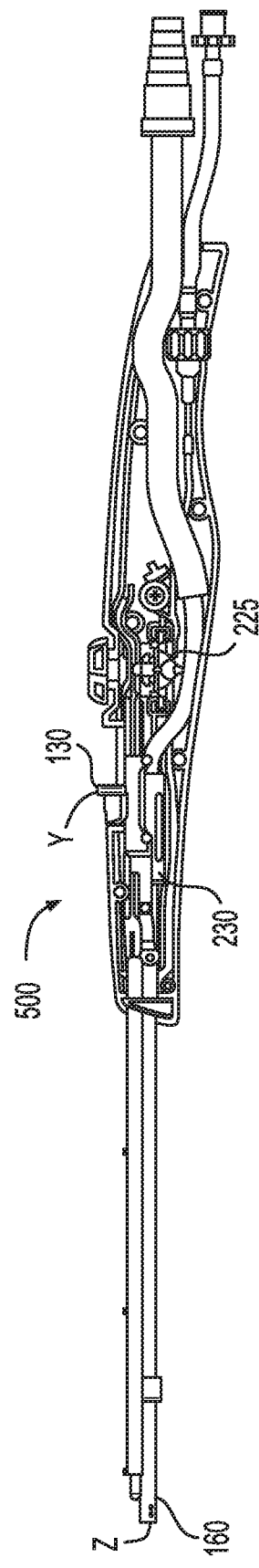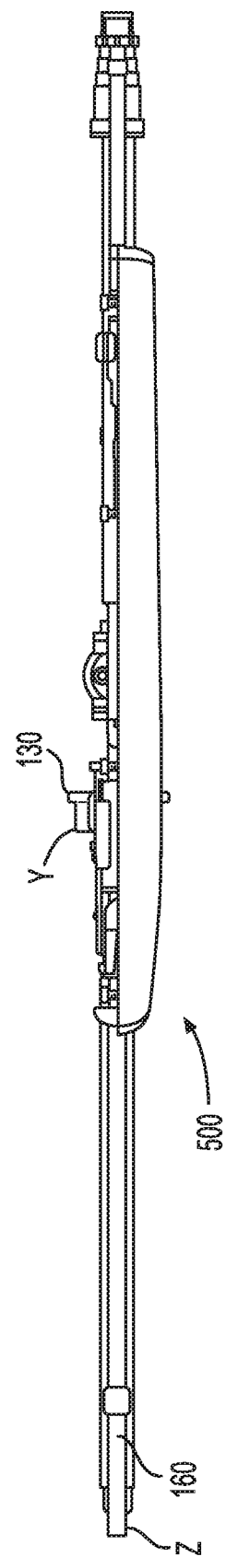

SYSTEMS AND METHODS FOR MANAGING FLUID AND SUCTION IN ELECTROSURGICAL SYSTEMS

BACKGROUND

Many internal surgical procedures require the removal of tissue as part of the surgical procedure. The removal of such tissue invariably results in severing multiple blood vessels leading to localized blood loss. Significant blood loss may comprise the patient's health by potentially leading to hypovolemic shock. Even minor blood loss may complicate the surgery by resulting in blood pooling into the surgical site, thereby obscuring the visibility of the tissue from the surgeons and surgical assistants. The problem of blood loss into the surgical site may be especially important in broad area surgeries, such as liver resection, in which multiple blood vessels may be severed during the procedure.

Typically, an electrosurgical device is used to seal the blood vessels, thereby preventing blood loss. Such electrosurgical devices may include bipolar devices that incorporate a pair of electrodes that are powered by RF (radiofrequency) energy to heat and coagulate the tissue and blood vessels. Direct application of the electrodes to the tissue may lead to unwanted effects such as localized tissue charring and fouling of the electrodes by charred tissue matter sticking to them.

A method to reduce charring and fouling may include introducing a saline fluid into the surgical site to irrigate the site. Alternatively, the saline fluid may be heated by the electrodes to form a steam to coagulate the tissue. In this manner, the tissue is not placed in direct contact with the electrodes and electrode fouling is prevented. Although a saline fluid may be used, any electrically conducting fluid (for example, an aqueous mixture containing ionic salts) may be used to promote steam-based coagulation. After the steam coagulates the tissue by transferring its heat thereto, the steam may condense to water. The resulting water may be used to clear the surgical site of unwanted material such as the remnants of the coagulated tissue. An aspirator or other vacuum device may be used to remove the mixture of water and tissue remnants. It may be difficult and inefficient for the surgeon to coagulate and aspirate the tissue especially if separate devices are required. Thus, a device incorporating the coagulation and aspiration functions is desirable.

The incorporation of both a saline source and an evacuation source for aspiration into a bipolar electrosurgical coagulation instrument may be problematic. If the aspirator operates continuously, then the saline may not reside in contact with the electrodes long enough to be heated and form steam. If the saline source operates continuously, then excess saline may be delivered to the surgical site and obscure the area from the surgeon. It is possible to have a device with multiple actuators to allow the surgeon to selectively emit a fluid to be vaporized by the electrodes and evacuate the surgical site. However, such multiple actuators may be clumsy to use and lead to hand and finger fatigue during a long surgical procedure.

Nevertheless, it is still possible that the electrodes may experience fouling from charred tissue matter sticking to them. Such charred material may interfere with the operation of the electrodes by acting as localized insulators at the electrode surfaces. Such localized insulation may distort or even reduce the electric fields produced by the electrodes, thereby reducing the effectiveness of the coagulation process. As a result, tissue coagulation may be reduced or impeded, thereby permitting blood to continue to flow into the surgical site despite the application of the electrical field to the electrodes. One method to address electrode fouling may be to remove the electrosurgical device from the surgical site and to manually remove the material from the electrodes. However, this method is not optimal as it may permit un-coagulated tissue to continue bleeding and will present an unwanted interruption to the surgical procedure.

Therefore, it is desirable to have an electrosurgical device that permits a surgeon to efficiently remove charred material from the surface of the electrodes while permitting the device to remain in situ.

SUMMARY

In one aspect, an electrosurgical device is presented that includes: a housing; a shaft extending distally from the housing; an end effector coupled to a distal end of the shaft, the end effector comprising: an electrode; a suction port; and a fluid port; and a control system communicatively coupled to the suction port and the fluid port and configured to control a rate of fluid flowing out of the fluid port and a rate of suction flowing into the suction port.

In another aspect, the electrosurgical device further includes: a first fluid path in fluid communication with the fluid port; and a second fluid path in fluid communication with the suction port; wherein the housing is configured to enclose a first portion of the first fluid path and a first portion of the second fluid path; and wherein the shaft is configured to enclose a second portion of the first fluid path and a second portion of the second fluid path.

In another aspect, the electrosurgical device further includes an impedance sensor configured to measure impedance experienced at the electrode.

In another aspect of the electrosurgical device, the control system is configured to control the rate of fluid flowing out of the fluid port based on the measured impedance experienced at the electrode.

In another aspect of the electrosurgical device, the control system is further configured to control the rate of suction flowing into of the suction port based on the measured impedance experienced at the electrode.

In another aspect, the electrosurgical device further includes a radio frequency (RF) current sensor configured to measure RF current applied to the electrode.

In another aspect of the electrosurgical device, the control system is configured to control the rate of fluid flowing out of the fluid port based on the measured RF current applied to the electrode.

In another aspect of the electrosurgical device, the control system is further configured to control the rate of suction flowing into of the suction port based on the measured RF current applied to the electrode.

In another aspect, the electrosurgical device further includes a temperature sensor configured to measure temperature of the fluid suctioned into the suction port.

In another aspect of the electrosurgical device, the control system is configured to control the rate of fluid flowing out of the fluid port based on the measured temperature of the fluid into the suction port.

In another aspect of the electrosurgical device, the control system is further configured to control the rate of suction flowing into of the suction port based on the measured temperature of the fluid into the suction port.

In another aspect of the electrosurgical device, the end effector further comprises a partially deflectable member that is configured to increase the rate of fluid out of the fluid port as the partially deflectable member increases in deflection.

In another aspect of the electrosurgical device, the control system is further configured to increase the rate of fluid flowing out of the fluid port the longer the electrode applies energy.

In another aspect of the electrosurgical device, the control system is further configured to decrease the rate of fluid flowing out of the fluid port the longer the electrode applies energy.

In another aspect, the electrosurgical device further includes a user interface console communicatively coupled to the control system and configured to receive an input from a user to manually control an initial fluid rate of the fluid port.

In another aspect of the electrosurgical device, the control system is further configured to automatically increase the fluid rate of the fluid port after the initial fluid rate is manually specified from the user interface console; wherein the automatic increase of the fluid rate occurs based on an earlier rise in measured temperature of the fluid at the suction port if the initial fluid rate is manually specified at a slower fluid rate, and the automatic increase of the fluid rate occurs based on a later rise in measured temperature of the fluid at the suction port if the initial fluid rate is manually specified at a faster fluid rate.

In another aspect of the electrosurgical device, the control system is configured to: detect an impedance spike based on a drastic change in impedance from the impedance sensor; and in response, increase the rate of fluid flowing out of the fluid port.

In another aspect, a method of a control system of an electrosurgical device is presented, the method comprising: accessing data from one or more sensors related to a physical characteristic of a function occurring at an end effector of the electrosurgical device; controlling a rate of fluid flowing to a fluid port of the electrosurgical device, based on the data related to the physical characteristic; and controlling a rate of suction flowing from a suction port of the electrosurgical device, based on the data related to the physical characteristic.

In another aspect of the method, the physical characteristic comprises a measure of impedance experienced at an electrode of the end effector of the electrosurgical device.

In another aspect of the method, the physical characteristic comprises a measure of RF current applied to an electrode of the end effector of the electrosurgical device.

In another aspect of the method, the physical characteristic comprises a temperature of fluid measured at the suction port at the end effector of the electrosurgical device.

BRIEF DESCRIPTION OF THE FIGURES

The features of the various aspects are set forth with particularity in the appended claims. The various aspects, however, both as to organization and methods of operation, together with advantages thereof, may best be understood by reference to the following description, taken in conjunction with the accompanying drawings as follows:

FIG. 1 illustrates a perspective view of one aspect of an electrosurgical device.

FIG. 2 illustrates an expanded view of one aspect of an end effector of the electrosurgical device depicted in FIG. 1.

FIG. 7 illustrates an additional perspective view of one aspect of the interior components of the electrosurgical device depicted in FIG. 1.

FIG. 8 illustrates an expanded perspective view of one aspect of an end effector of the electrosurgical device depicted in FIG. 7.

FIG. 9 illustrates an expanded perspective view of one aspect of activation controls of the electrosurgical device depicted in FIG. 7.

FIGS. 16, 17, and 18 illustrate plan views of the top, side, and bottom, respectively, of one aspect of the electrosurgical device depicted in FIG. 13 illustrating a second position of one aspect of a slide switch.

DETAILED DESCRIPTION

Applicant of the present application owns the following patent applications filed on Sep. 29, 2017 and which are each herein incorporated by reference in their respective entireties:

U.S. patent application Ser. No. 15/720,810, titled BIPOLAR ELECTRODE SALINE LINKED CLOSED LOOP MODULATED VACUUM SYSTEM, by inventors David A. Witt et al., filed on Sep. 29, 2017, now U.S. Patent Application Publication No. 2019/0099209.

U.S. patent application Ser. No. 15/720,822, titled IMPROVING SALINE CONTACT WITH ELECTRODES, by inventors Mark A. Davison et al., filed on Sep. 29, 2017, now U.S. Patent Application Publication No. 2019/0099212.

U.S. patent application Ser. No. 15/720,840, titled FLEXIBLE ELECTROSURGICAL INSTRUMENT, by inventors David A. Witt et al., filed on Sep. 29, 2017, now U.S. Patent Application Publication No. 2019/0099217.

Aspects of the present disclosure include control systems of an electrosurgical system for managing the flow of fluid, such as saline, and rates of aspiration or suction, in response to various states of conditions at a surgical site. The control systems may monitor and adjust to impedance at the surgical site, temperature of the surgical tissue, RF current of electrodes, and may account for certain undesirable conditions, such as the electrodes sticking. The control systems may include various automatic sensing scenarios, while also allowing for several manual conditions. Rather than rely on a user to manually control settings to adjust for fluid rate and suction rate, the control system(s) may relieve a user of these tasks and control more reliably the fluid and suction rates to produce more reliable results. The control systems described herein may increase safety and produce more accurate surgical procedures, due to the surgeon being able to devote more attention to perform the acts of surgery and not have to divert attention to manually controlling rates of suction and fluid flow.

Figure 3:
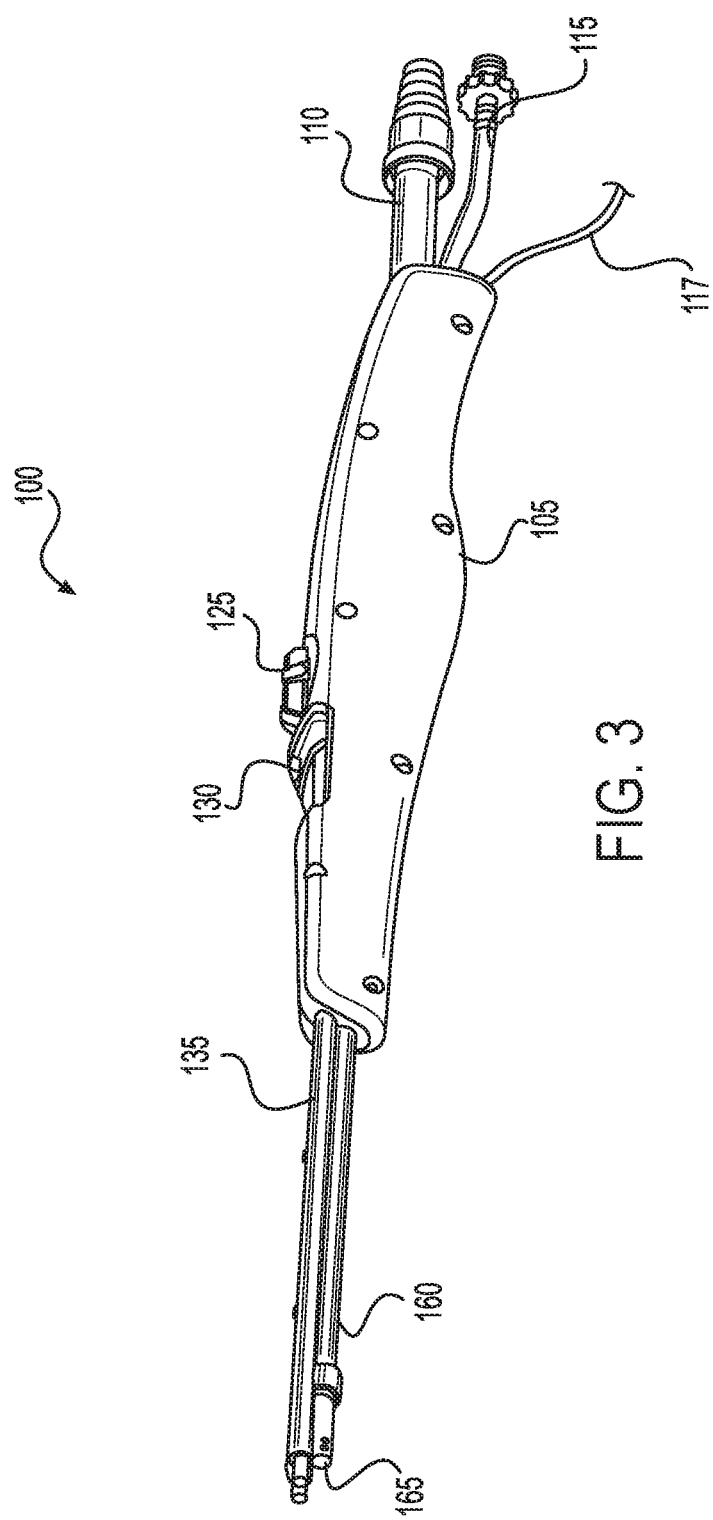
FIG. 3 illustrates a side perspective view of one aspect of the electrosurgical device depicted in FIG. 1.

FIGS. 1-3 depict views of one example of such an electrosurgical device 100, according to aspects of the present disclosure. For FIGS. 1-22, common reference numbers refer to common components within the figures.

The electrosurgical device 100 may include a housing 105 with a shaft 135 extending distally from the housing 105. The housing 105 may include, on a proximal end, a proximal fluid source port 115 and a proximal fluid evacuation port 110. In some electrosurgical device systems, the proximal fluid source port 115 may be placed in fluid communication with a source of a fluid, for example saline, buffered saline, Ringer's solution, or other electrically conducting fluids such as aqueous fluids containing ionic salts. The fluid source may operate as a gravity feed source or it may include components to actively pump the fluid into the proximal fluid source port 115. An actively pumping fluid source may include, without limitation, a power supply, a pump, a fluid source, and control electronics to allow a user to actively control the pumping operation of the actively pumping fluid source. In some electrosurgical device systems, the fluid evacuation port 110 may be placed in fluid communication with a vacuum source. The vacuum source may include a power supply, a pump, a storage component to store material removed by the vacuum source, and control electronics to allow a user to actively control the pumping operation of the vacuum source.

In addition, the housing 105 may include a connector to which a cable 117 of an energy source 120 may be attached. The energy source 120 may be configured to supply energy (for example RF or radiofrequency energy) to the electrodes 145a,b. The energy source 120 may include a generator configured to supply power to the electrosurgical device 100 through external means, such as through the cable 117. In certain instances, the energy source 120 may include a microcontroller coupled to an external wired generator. The external generator may be powered by AC mains. The electrical and electronic circuit elements associated with the energy source 120 may be supported by a control circuit board assembly, for example. The microcontroller may generally comprise a memory and a microprocessor ("processor") operationally coupled to the memory. The electronic portion of the energy source 120 may be configured to control transmission of energy to electrodes 145a,b at the end effector 140 of the electrosurgical device 100. It should be understood that the term processor as used herein includes any suitable microprocessor, microcontroller, or other basic computing device that incorporates the functions of a computer's central processing unit (CPU) on an integrated circuit or at most a few integrated circuits. The processor may be a multipurpose, programmable device that accepts digital data as input, processes it according to instructions stored in its memory, and provides results as output. It is an example of sequential digital logic, as it has internal memory. Processors operate on numbers and symbols represented in the binary numeral system. The energy source 120 may also include input devices to allow a user to program the operation of the energy source 120.

The housing 105 may also include one or more activation devices to permit a user to control the functions of the electrosurgical device 100. In some non-limiting examples, the electrosurgical device 100 may include a metering valve 125 that may be activated by a user to control an amount of fluid flowing through the electrosurgical device and provide, at the distal end, an amount of the fluid to the end effector 140. In some non-limiting examples, the metering valve 125 may also permit the user to control an amount of energy supplied by the energy source 120 to the electrodes 145a,b at the end effector 140. As an example, the metering valve 125 may comprise a screw activation pinch valve to regulate the flow of fluid through the electrosurgical device 100. Additionally, the metering valve 125 may have a push-button activation function to permit current to flow from the energy source 120 to the electrodes 145a,b upon depression of the push-button by a user. It may be recognized that in some non-limiting examples, the housing 105 may include the metering valve 125 to allow regulation of fluid flow through the electrosurgical device 100 and a separate energy control device to control the amount of current sourced to the electrodes 145a,b.

The housing 105 may also be attached to a shaft 135 at a distal end of the housing 105. An end effector 140 may be associated with a distal end of the shaft 135. The end effector 140 may include electrodes 145a,b that may be in electrical communication with the energy source 120 and may receive electrical power therefrom. In some non-limiting examples, a first electrode 145a may receive electrical energy of a first polarity (such as a positive polarity) from the energy supply 120 and the second electrode 145b may receive electrical energy of a second and opposing polarity (such as a negative polarity) from the energy supply 120. Alternatively, the first electrode 145a may be connected to a ground terminal of the energy supply 120, and the second electrode 145b may be connected to a varying AC voltage terminal of the energy supply 120. The electrodes 145a,b may extend beyond the distal end of the shaft 135. The extended ends of the electrodes 145a,b be separated by a diverter 155. The diverter 155 may contact the first electrode 145a at a first edge of the diverter 155, and the diverter 155 may contact the second electrode 145b at a second edge of the diverter 155. The diverter 155 may comprise an electrically insulating material and/or a heat resistant material, which may include, without limitation, a plastic such as a polycarbonate or a ceramic. The diverter 155 may be deformable or non-deformable. In some non-limiting examples, the housing 105 may include a mechanism to control a shape of a deformable diverter 155.

The end effector 140 may also include a fluid discharge port 150 that may be in fluid communication with the fluid source port 115 through a first fluid path. The first fluid path, such as a source fluid path (see 315 in FIG. 6), may permit the fluid to flow from the fluid source port 115 to the fluid discharge port 150. In some non-limiting examples, the fluid discharge port 150 may be positioned above the diverter 155 so that a fluid emitted by the fluid discharge port 150 may be collected on a top surface of the diverter 155. The end effector may also include a fluid aspiration port 165 that may be in fluid communication with the fluid evacuation port 110 through a second fluid path. The second fluid path, such as an aspirated fluid path (see 210 in FIGS. 7 and 9), may permit a liquid mixture generated at the surgical site to flow from the fluid aspiration port 165 to the fluid evacuation port 110. The liquid mixture may then be removed from the electrosurgical device 100 by the vacuum source and stored in the storage component for later removal.

In some non-limiting examples, the fluid aspiration port 165 may be formed at the distal end of an aspiration tube 160. The aspiration tube 160 may also form part of the aspirated fluid path 210. The aspiration tube 160 may be located within the shaft 135 or it may be located outside of and beneath the shaft 135. An aspiration tube 160 located outside of the shaft 135 may be in physical communication with an external surface of the shaft 135. In some examples, the aspiration tube 160 may have a fixed location with respect to the shaft 135. In some alternative examples, the aspiration tube 160 may be extendable in a distal direction with respect to the shaft 135. Extension of the extendable aspiration tube 160 may be controlled by means of an aspiration tube control device. As one non-limiting example, the aspiration tube control device may comprise a slide switch 130. The slide switch 130, in a first position (for example, in a proximal position), may cause the aspiration tube 160 to remain in a first or retracted position in which the aspiration port 165 is located essentially below the fluid discharge port 150. However, the slide switch 130 in a second position (for example in a distal position), may cause the aspiration tube 160 to extend in a distal direction to a fully extended position so that the aspiration port 165 is located distal from and beneath the fluid discharge port 150. In one example, the slide switch 130 may preferentially position the aspiration tube 160 in one of two positions, such as the retracted position and the fully extended position. It may be recognized, however, that the slide switch 130 may also permit the aspiration tube 160 to assume any position between the retracted position and the fully extended position. Regardless of the position of the aspiration tube 160 as disclosed above, the aspiration port 165 may be maintained at a location beneath a plane defined by the top surface of the diverter 155. In this manner, the diverter 155 is configured to prevent fluid emitted by the fluid discharge port 150 from directly being removed at the aspiration port 165.

Figure 4:
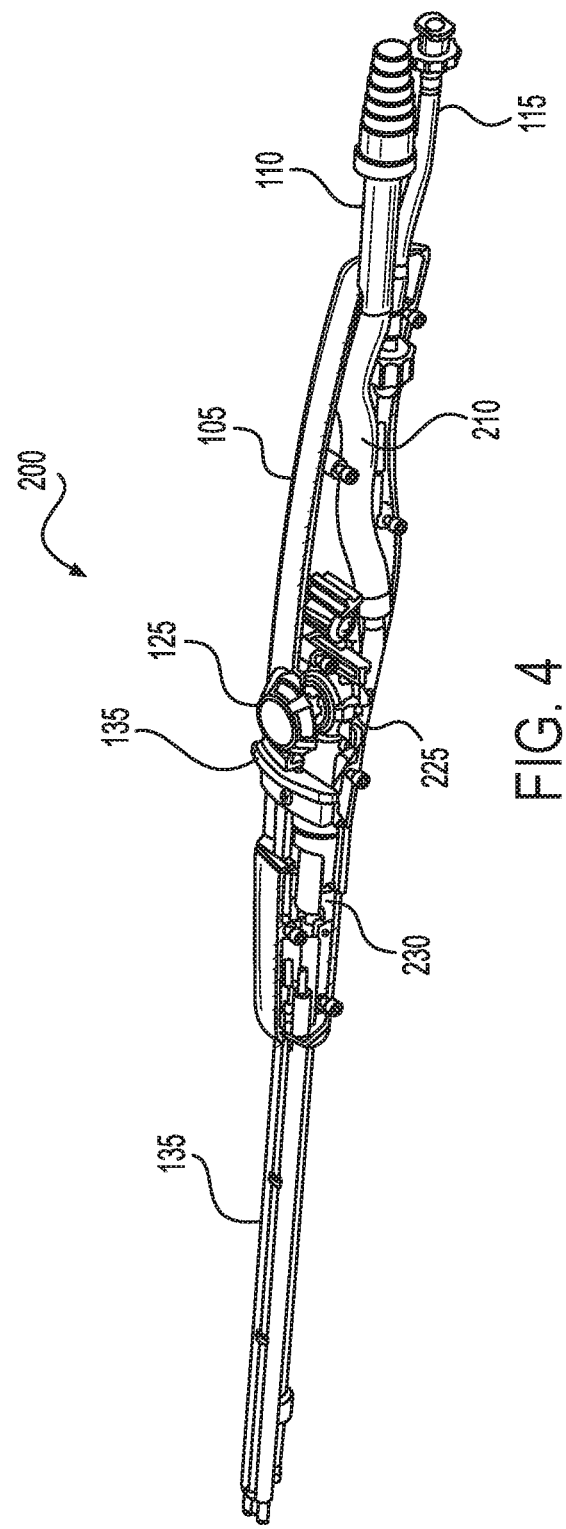
FIG. 4 illustrates a partial sectional perspective view of one aspect of the electrosurgical device depicted in FIG. 1.
Figure 5:
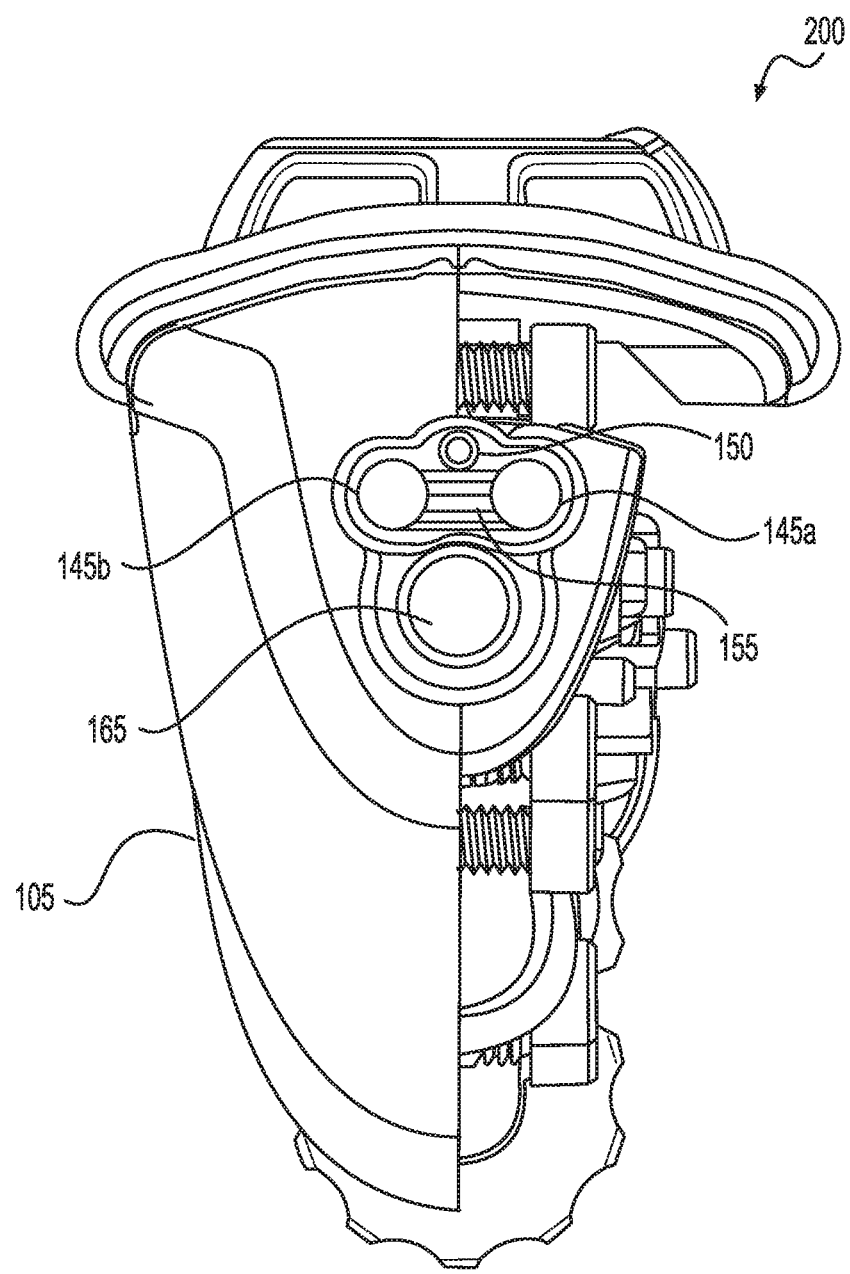
FIG. 5 illustrates a partial sectional plan front (distal) view of one aspect of the electrosurgical device depicted in FIG. 1.
Figure 6:
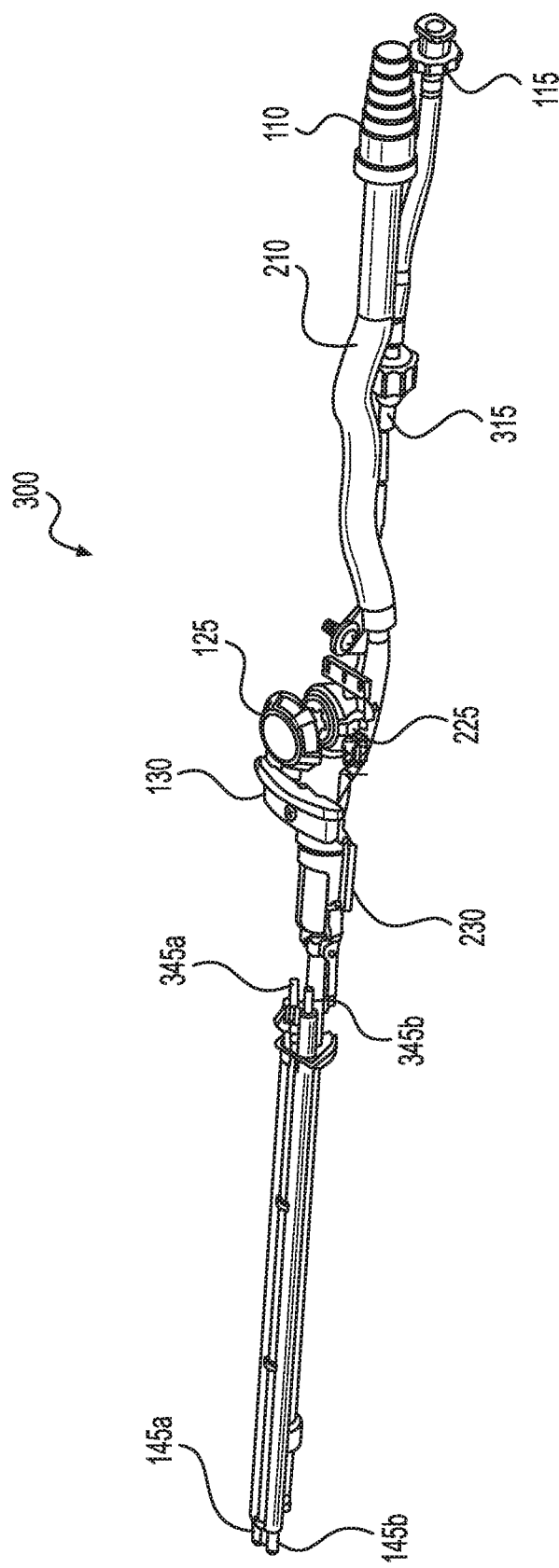
FIG. 6 illustrates a perspective view of one aspect of the interior components of the electrosurgical device depicted in FIG. 1.

FIGS. 4 and 5 present partial interior views of an electrosurgical device 200. In addition to the components disclosed above with respect to FIGS. 1-3, the electrosurgical device 200 includes an aspirated fluid path 210 that forms a fluid connection between the proximal fluid evacuation port 110 and the distal fluid aspiration port 165. Also illustrated are valve components 225 of the metering valve 125 and control components 230 of the aspiration tube such as, for example, a slide switch 130. Fluid discharge port 150, electrodes 145a,b, fluid aspiration port 165, and a portion of housing 105 are also illustrated in FIGS. 4 and 5.

FIGS. 6-9 present a variety of views of the interior components of electrosurgical device 300. FIG. 8 is a close-up view of the distal end of the electrosurgical device 300 shown in FIG. 7, and FIG. 9 is a close-up view of actuator components of the electrosurgical device 300 shown in FIG. 7 depicting the metering valve 125 and slide switch 130. Additional components depicted in FIGS. 6-9 include the source fluid path 315 that forms a fluid connection between the proximal fluid source port 115 and the distal fluid discharge port 150. In some examples, the valve components 225 of the metering valve 125 are disposed along the length of the source fluid path 315 permitting a user of electrosurgical device 300 to regulate a flow of fluid through the source fluid path 315 from the fluid source port 115 to the fluid discharge port 150. In some examples of the valve components 225, a screw actuator, such as a pinch valve, may be used to compress a portion of the source fluid path 315, thereby restricting a flow of fluid therethrough. It may be recognized that any number of fluid control valves may be used as valve components 225 including, without limitation, a ball valve, a butterfly valve, a choke valve, a needle valve, and a gate valve. It may be understood from FIGS. 6-9 that source fluid path 315 extends from fluid source port 115 through the housing 105 and through shaft 135 to the distal fluid discharge port 150. Similarly, it may be understood from FIGS. 6-9 that aspirated fluid path 210 extends form the proximal fluid evacuation port 110 through the housing 105 and through shaft 135 to the distal fluid aspiration port 165. Additionally, electrodes 145a,b may extend from housing 105 through shaft 135 and extend distally and protrude from the end of shaft 135. Alternatively, electrodes 145a,b may extend only through the shaft 135 and extend distally and protrude from the end of shaft 135. Proximal ends 345a,b of the electrodes 145a,b, may receive connectors to place the electrodes 145a,b in electrical communication with energy source 120. Electrodes 145a,b may receive the electrical energy from the energy source 120 to permit coagulation to the tissue in the surgical site either through direct contact of the tissue with the protruding portion of the electrodes 145a,b, or through heating a fluid contacting electrodes 145a,b.

Figure 10:
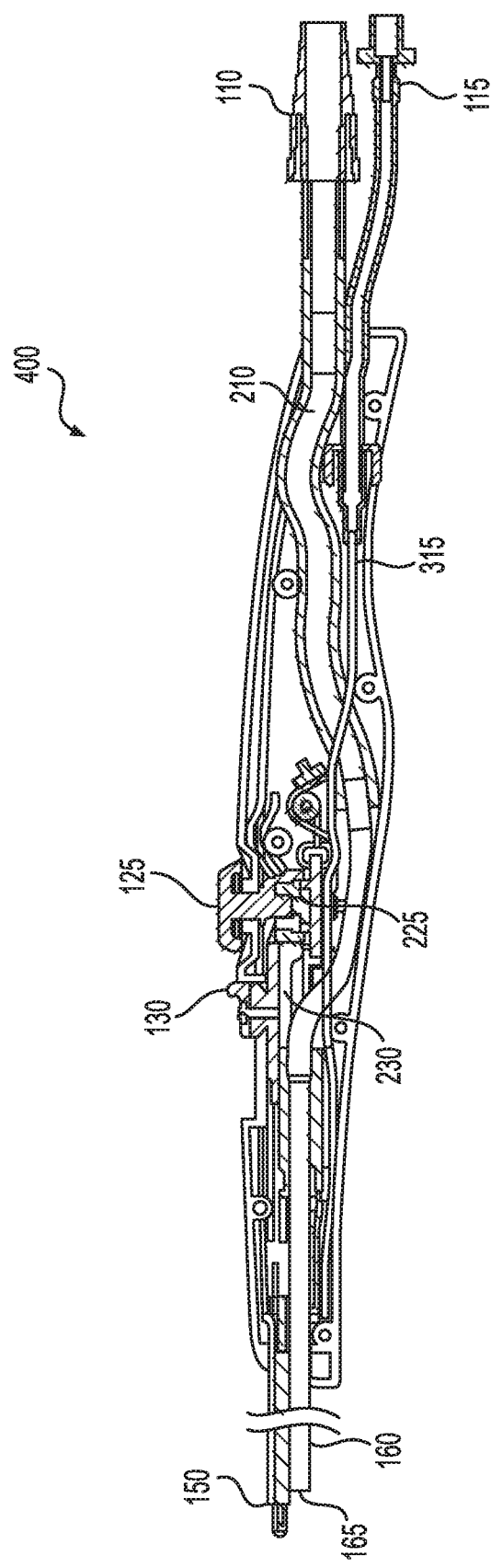
FIG. 10 illustrates a cross-sectional view of one aspect of the electrosurgical device depicted in FIG. 4.

FIG. 10 is a cross-sectional view of electrosurgical device 400. In particular, the cross-sectional view 400 illustrates the two fluid paths through the device. Thus, FIG. 10 illustrates source fluid path 315 in fluid communication with the proximal fluid source port 115 and the distal fluid discharge port 150. Additionally, FIG. 10 illustrates an example of a physical relationship between source fluid path 315 and the valve components 225 of the metering valve 125. FIG. 10 also illustrates an example in which the source fluid path 315 may extend through both the housing 105 and the shaft 135 (see e.g., FIG. 4). Further, FIG. 10 illustrates aspirated fluid path 210 in fluid communication with the proximal fluid evacuation port 110 and the distal fluid aspiration port 165. The aspirated fluid path 210 may also include an aspiration tube 160 that may be disposed at a distal end of the aspirated fluid path 210. The distal fluid aspiration port 165 may be formed at a distal end of the aspiration tube 160.

Figure 11:
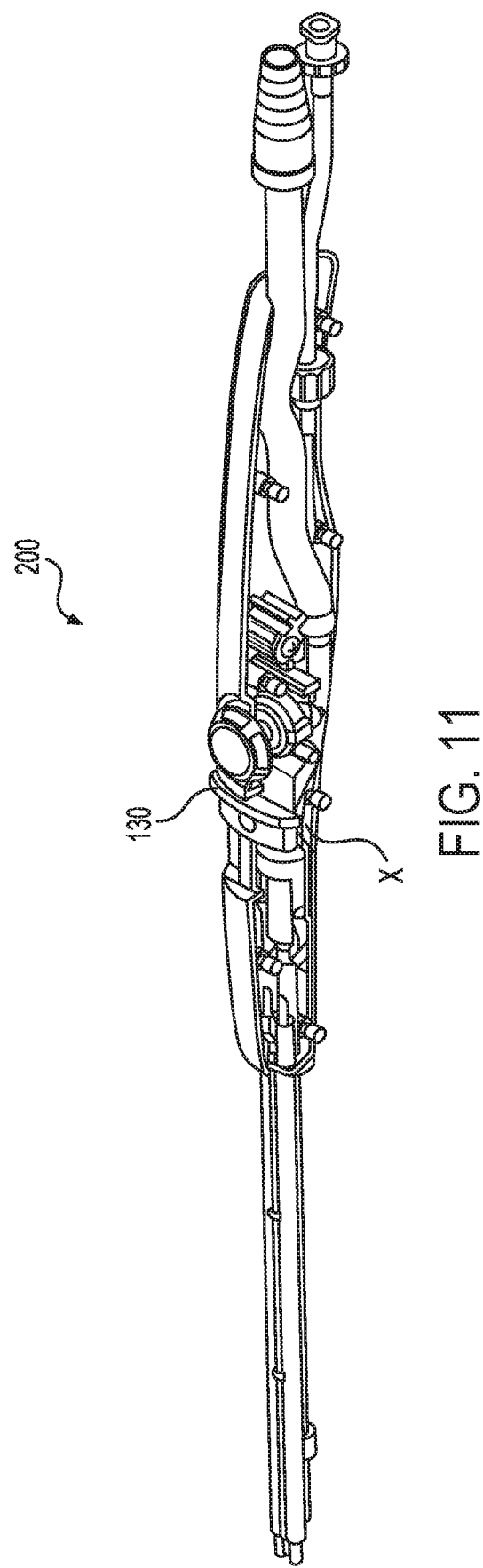
FIG. 11 illustrates partial sectional perspective view of one aspect of the electrosurgical device depicted in FIG. 4 illustrating a first position of one aspect of a slide switch.
Figure 12:
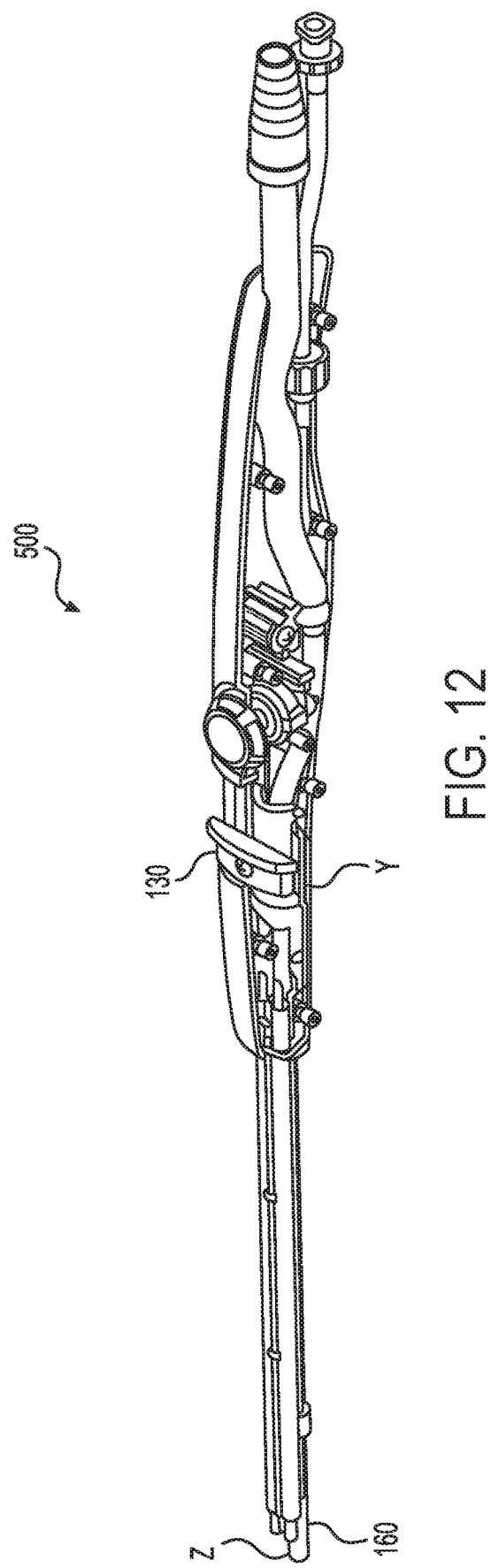
FIG. 12 illustrates partial sectional perspective view of one aspect of the electrosurgical device depicted in FIG. 4 illustrating a second position of one aspect of a slide switch.
Figure 14:
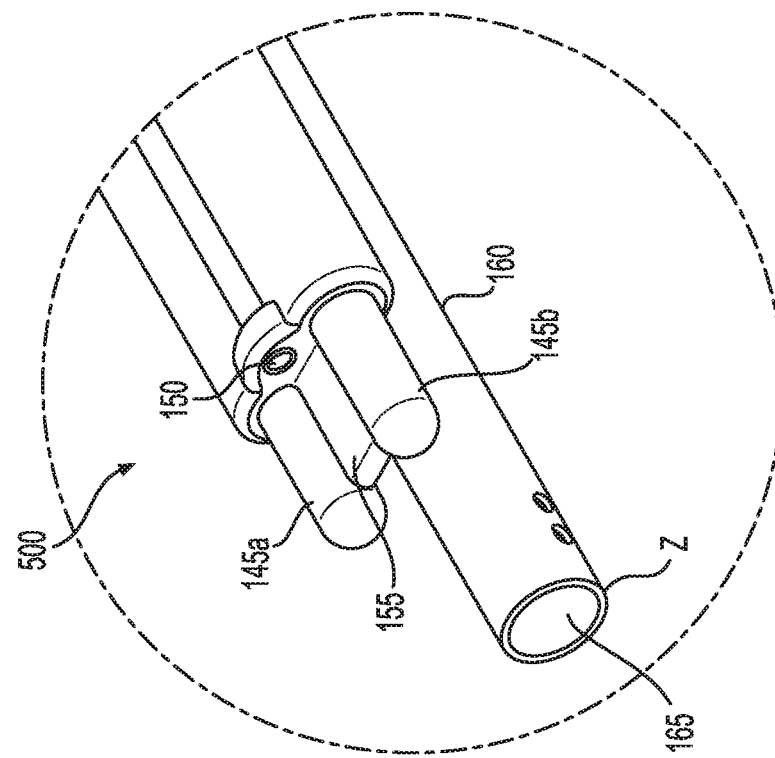
FIG. 14 illustrates an expanded perspective view of one aspect of an end effector of the electrosurgical device depicted in FIG. 13 illustrating an extended position of one aspect of an aspiration tube.
Figure 13:
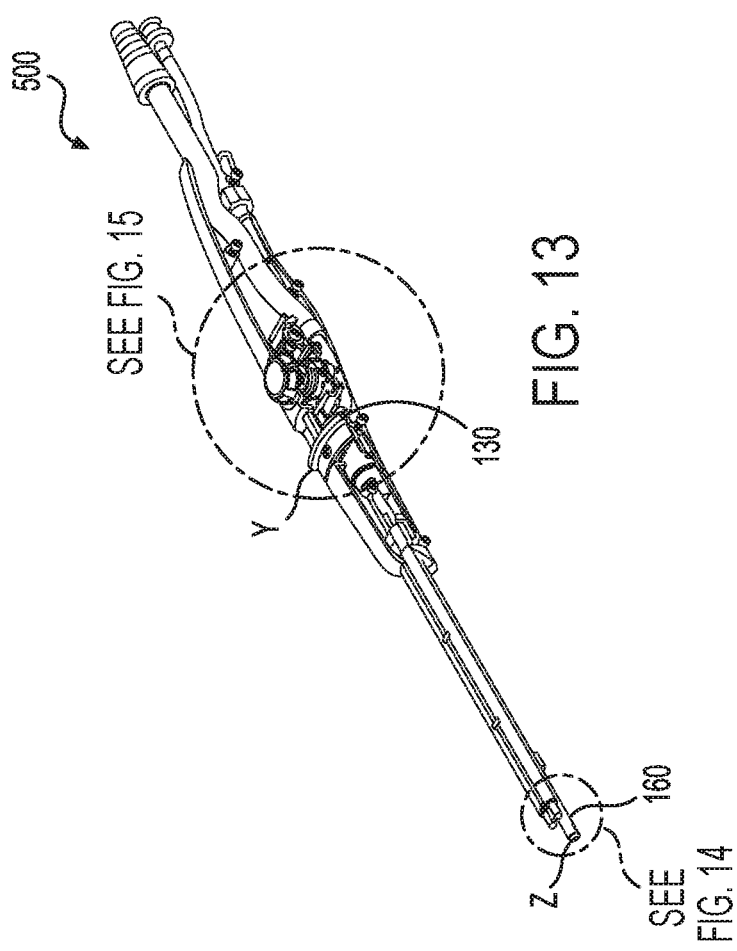
FIG. 13 illustrates an additional perspective view of one aspect of the interior components of the electrosurgical device depicted in FIG. 4 illustrating a second position of one aspect of a slide switch.
Figure 15:
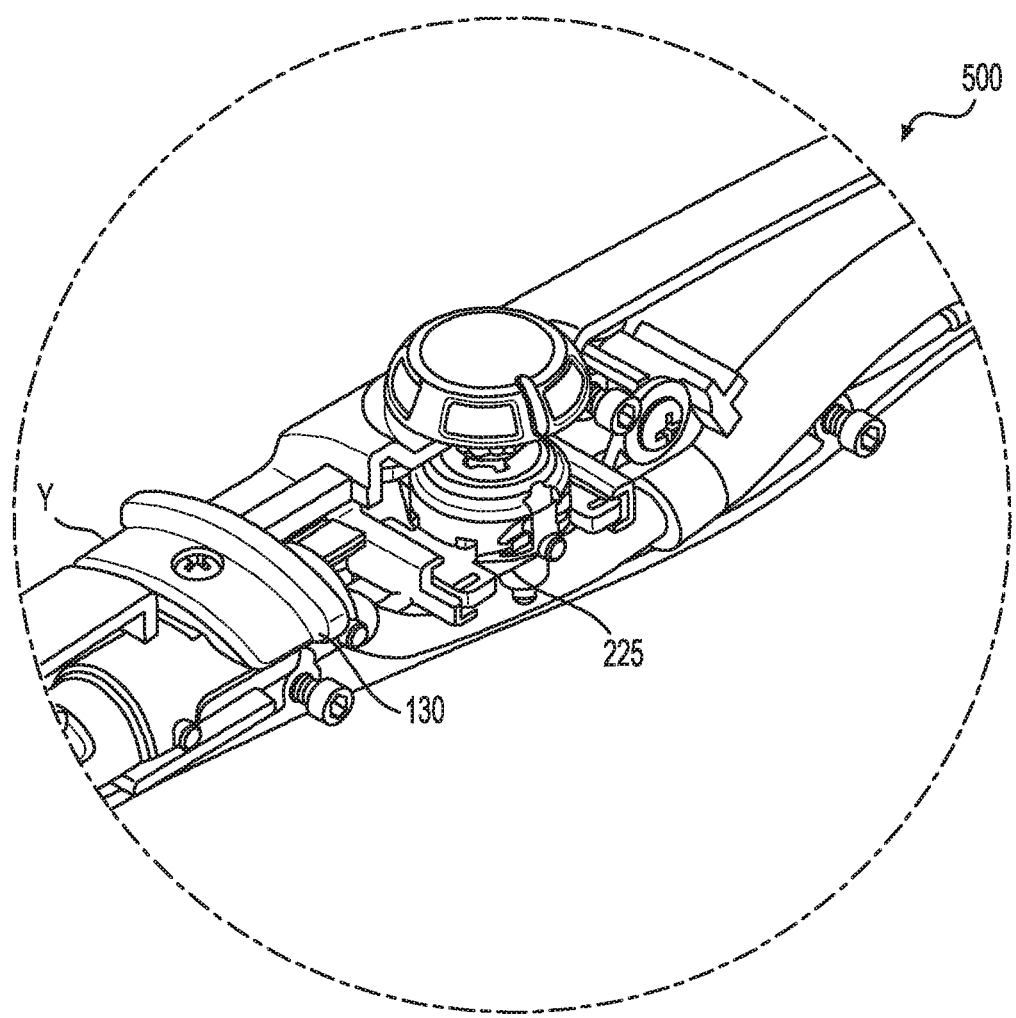
FIG. 15 illustrates an expanded perspective view of one aspect of activation controls of the electrosurgical device depicted in FIG. 13 illustrating a second position of one aspect of a slide switch.
Figure 19:
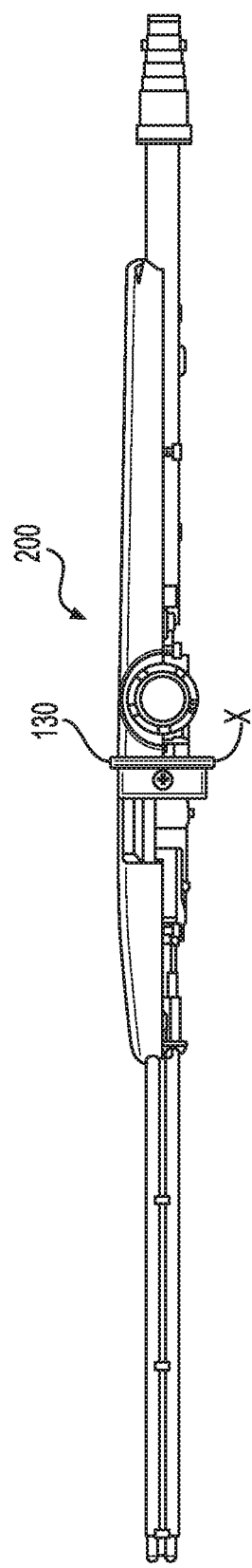
FIGS. 19, 20, and 21 illustrate plan views of the top, side, and bottom, respectively, of one aspect of the electrosurgical device depicted in FIG. 4 illustrating a first position of one aspect of a slide switch.
Figure 20:
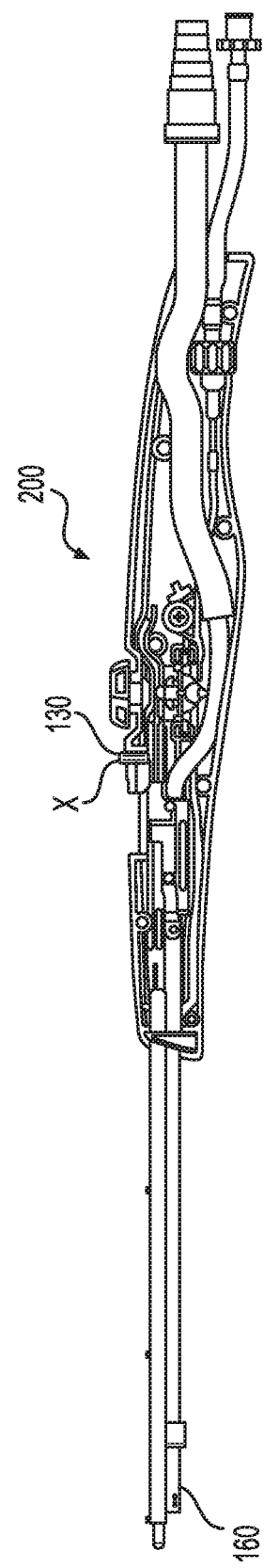
Figure 21:
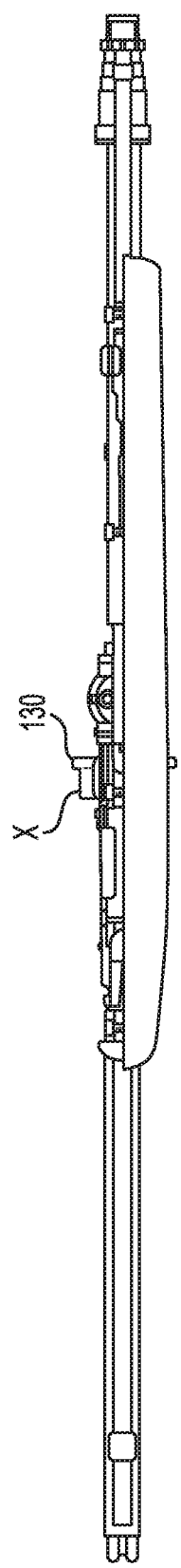

FIGS. 11-21 illustrate partial interior views of an electrosurgical device 200 having an aspiration tube 160 in a proximal or retracted position and an electrosurgical device 500 (FIG. 12) having an aspiration tube 160 in an distal or extended position Z. FIG. 11 is similar to FIG. 4 and particularly illustrates a first and proximal position X of the slide switch 130 (as a non-limiting example of an aspiration tube control device) along with a proximal or retracted position of aspiration tube 160. FIG. 12 particularly illustrates a second and distal position Y of the slide switch 130 (as a non-limiting example of an aspiration tube control device) in addition to a distal or extended position Z of aspiration tube 160. FIG. 13 illustrates an alternative perspective view of electrosurgical device 500. FIG. 14 is an expanded perspective view of the distal end of the electrosurgical device 500 shown in FIG. 13, particularly illustrating the distal end of aspiration tube 160 in the extended position Z. FIG. 15 is an expanded perspective view of actuator components of the electrosurgical device 500 shown in FIG. 13, particularly illustrating the second or distal position X of the slide switch 130. FIGS. 16, 17, and 18 present plan views of the top, side, and bottom, respectively, of electrosurgical device 500. FIGS. 16-18 may be compared with FIGS. 19, 20, and 21 which present plan views of the top, side, and bottom, respectively, of electrosurgical device 200. FIGS. 16-18 illustrate the distal positions Y and Z of slide switch 130 and aspiration tube 160, respectively. FIGS. 19-21 illustrate the proximal position X of slide switch 130 and the proximal or retracted position of aspiration tube 160.

Figure 22:
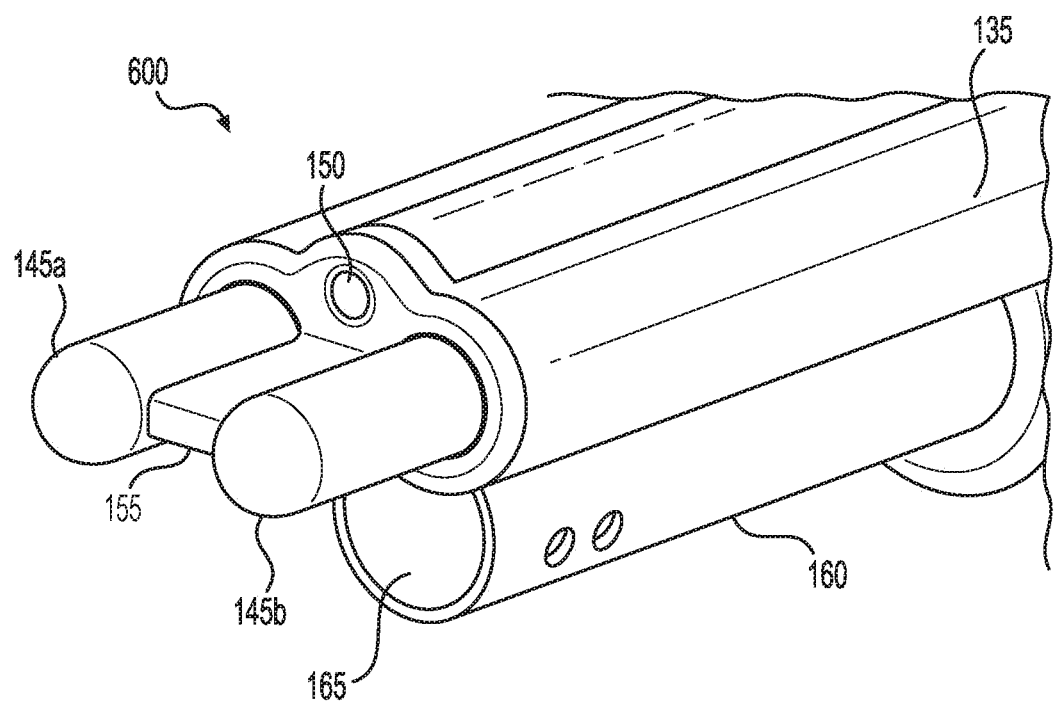
FIG. 22 illustrates a perspective view of one aspect of an end effector of the electrosurgical device depicted in FIG. 1.

FIG. 22 presents a perspective view of a general example of an end effector 600. As disclosed above, the end effector may be composed of a pair of electrodes 145a,b, extending from a shaft 135, a distal fluid discharge port 150, a diverter 155, and an aspiration port 165 that may be part of an aspiration tube 160. The diverter 155 may be placed between the pair of electrodes 145a,b in such a manner as to form a contact of a first edge of the diverter 155 with a surface of one electrode 145a, and a contact of a second edge of the diverter 155 with a surface on a second electrode 145b. In some examples, a proximal edge of the diverter 155 may form a mechanical communication with an end surface of the shaft 135. In this manner, fluid emitted by the distal fluid discharge port 150 may be retained on a first or top surface of the diverter 155. The fluid on the top surface of the diverter 155 may be retained on that surface for a sufficient time to maintain contact of the fluid with a surface of both electrodes 145a,b. If the fluid is an ionic fluid, current passing through the fluid between the electrodes 145a,b may heat the fluid sufficiently to form a steam capable of cauterizing tissue.

It may be recognized that the electrodes 145a,b may be fabricated to have any type of geometry that may improve the effectiveness of the electrodes 145a,b. For example, the electrodes 145a,b may be chamfered to result in oval distal ends in which the respective long axes are directed towards an inner portion of the end effector and pointing towards the diverter. Alternatively the distal portion of the electrodes 145a,b may have a circular or oval cross section, but the electrodes 145a,b may have a fabiform or kidney-shaped cross section closer (proximal) to the shaft 135.

Figure 23:
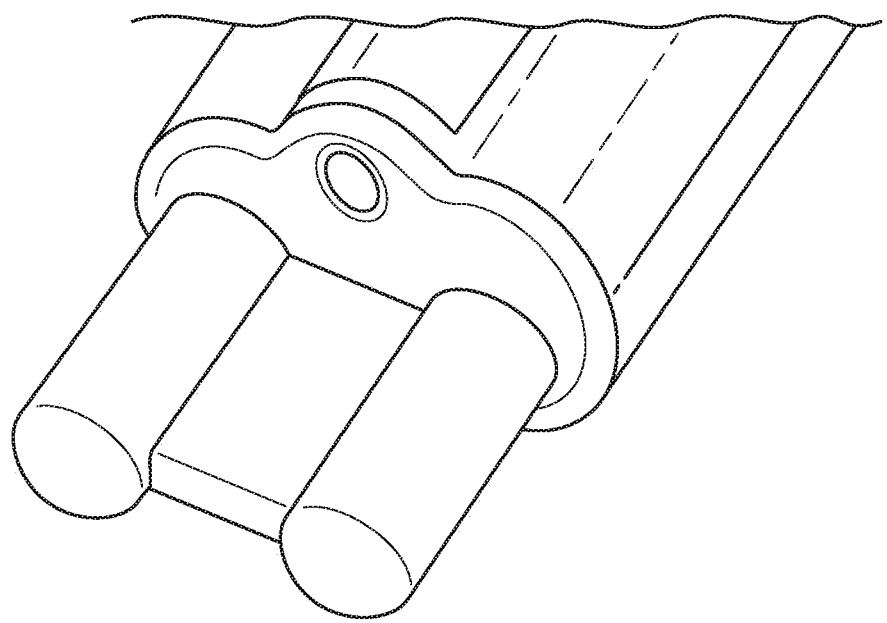
FIG. 23 illustrates a perspective view of a model of one aspect of an end effector of the electrosurgical device depicted in FIG. 1.

FIG. 23 depicts a perspective view of a fabricated model of the end effector 600 as depicted in FIG. 22.

Aspects of the present disclosure include control systems of an electrosurgical system for managing the flow of fluid, such as saline, and rates of aspiration or suction, in response to various states of conditions at the surgical site. The control systems may monitor and adjust to impedance at the surgical site, temperature of the surgical tissue, RF current of electrodes, and may account for certain undesirable conditions, such as the electrodes sticking. The control systems may include various automatic sensing scenarios, while also allowing for several manual conditions.

Figure 24:
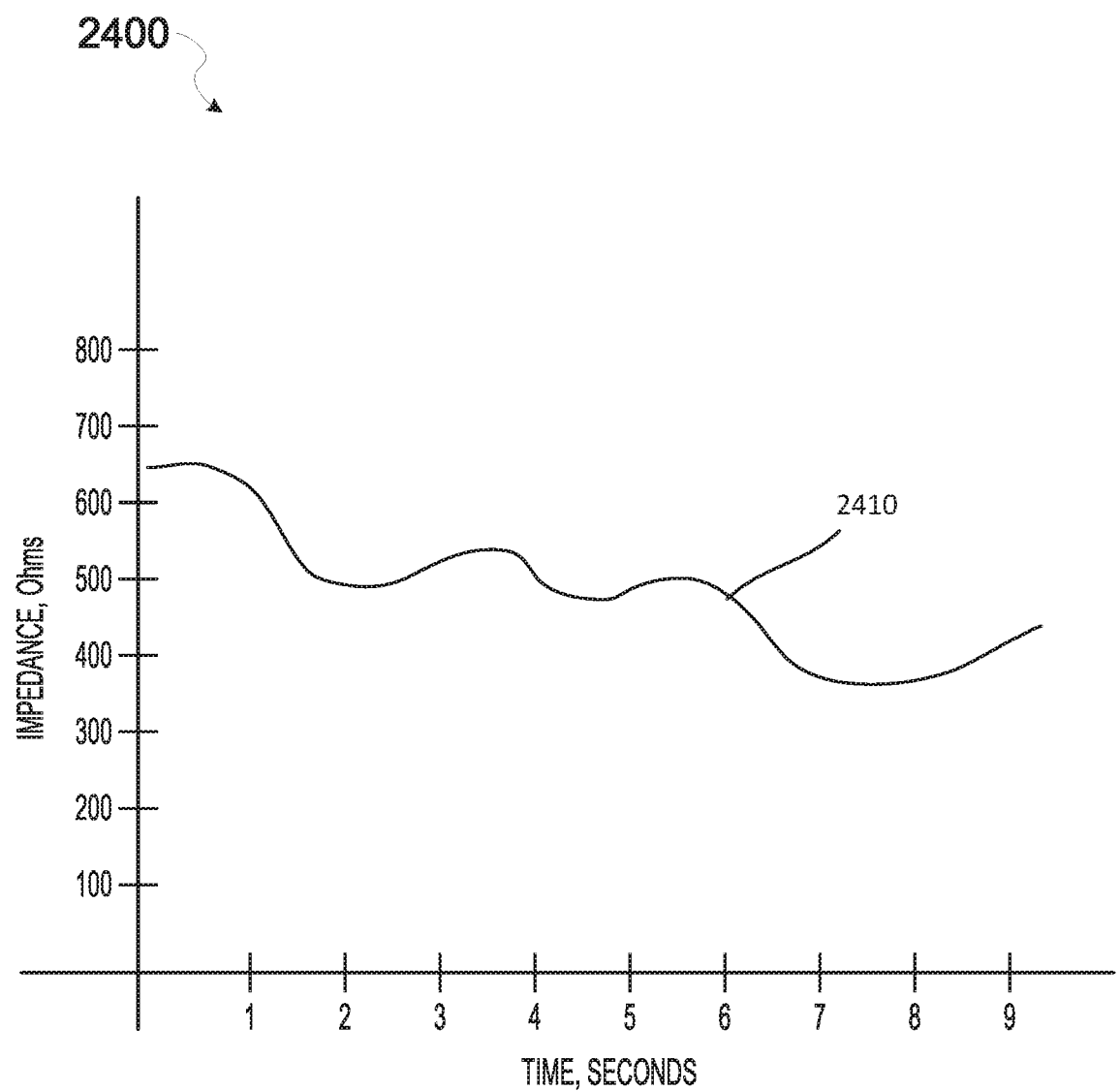
FIG. 24 shows an example plot of an amount of impedance experienced by an end effector providing electrosurgical energy to coagulate tissue at the surgical site, over a period of time.

Referring to FIG. 24, graph 2400 shows an example plot 2410 of an amount of impedance experienced by an end effector (e.g., end effector 140) providing electrosurgical energy to coagulate tissue at the surgical site, over a period of time. In this example, the amount of impedance, expressed in ohms, gradually changes at the surgical site. This is a sign that amount of fluid flowing to the surgical site and appropriate amount of suction is well-managed, in that too much or too little fluid would create wild imbalances in measured impedance. The various example techniques described herein for managing flow of fluid and suction are designed to establish such a smooth curve in impedance over time.

Figure 25:
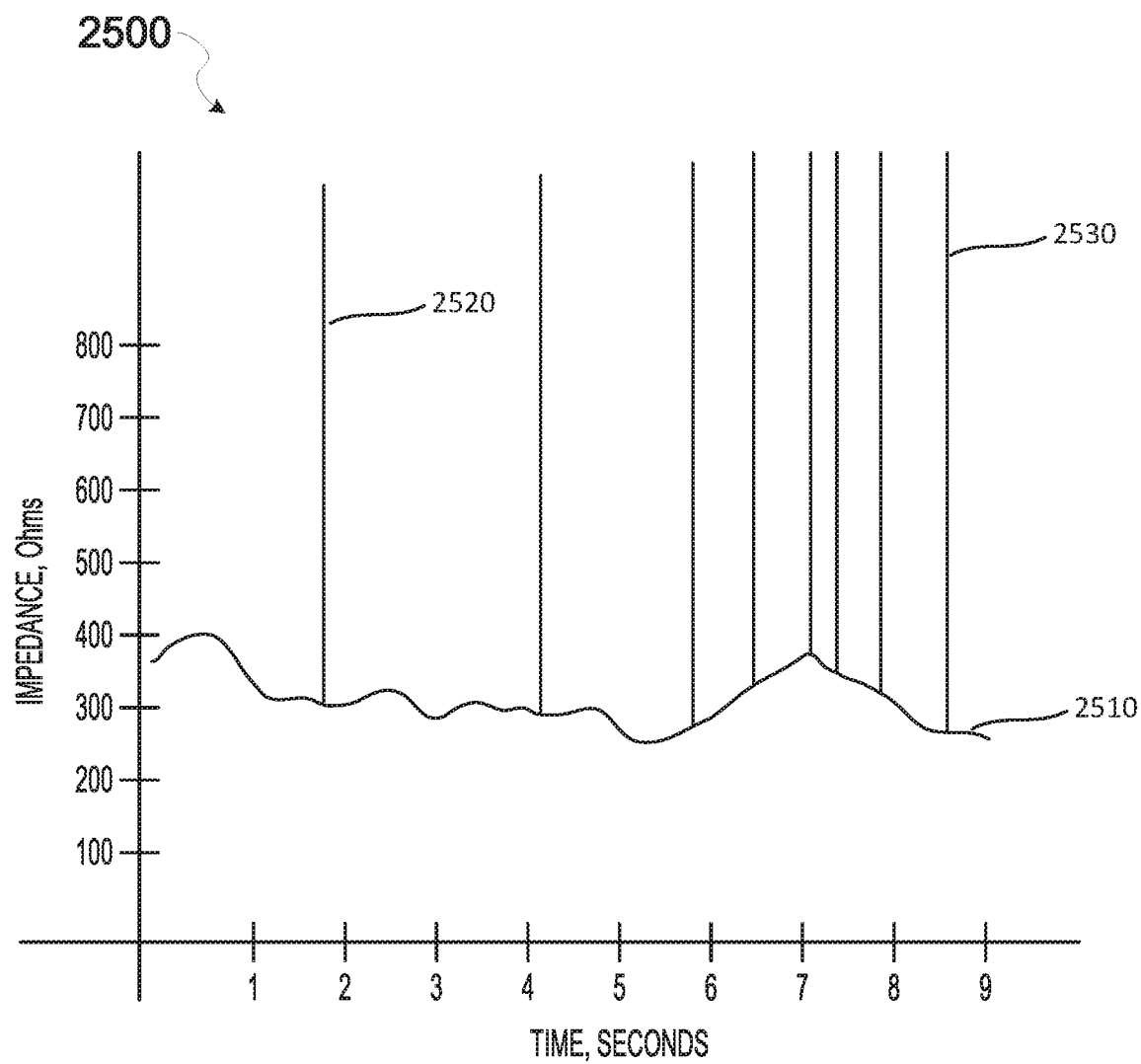
FIG. 25 shows an example of an undesirable impedance plot, including many impedance spikes, amidst an ordinary level of impedance over time as indicated by the plot line.

Referring to FIG. 25, graph 2500 shows an example of an undesirable impedance plot, including many impedance spikes, e.g., spikes 2520 and 2530, amidst an ordinary level of impedance over time as indicated by the plot line 2510. It has been observed that sudden impedance spikes are a precursor and an indicator of sticking by the electrodes. Unwanted sticking by the electrodes can create a danger that the electrodes may apply to much energy to a particular location at the surgical site, possibly causing errors during surgery. It is therefore desirable to adjust the fluid rate automatically as much as possible based on sensed conditions at the surgical site to prevent impedance spikes, and ultimately reduce the possibility of sticking by the electrodes. FIGS. 26-39 describe various aspects to address these problems.

Figure 26:
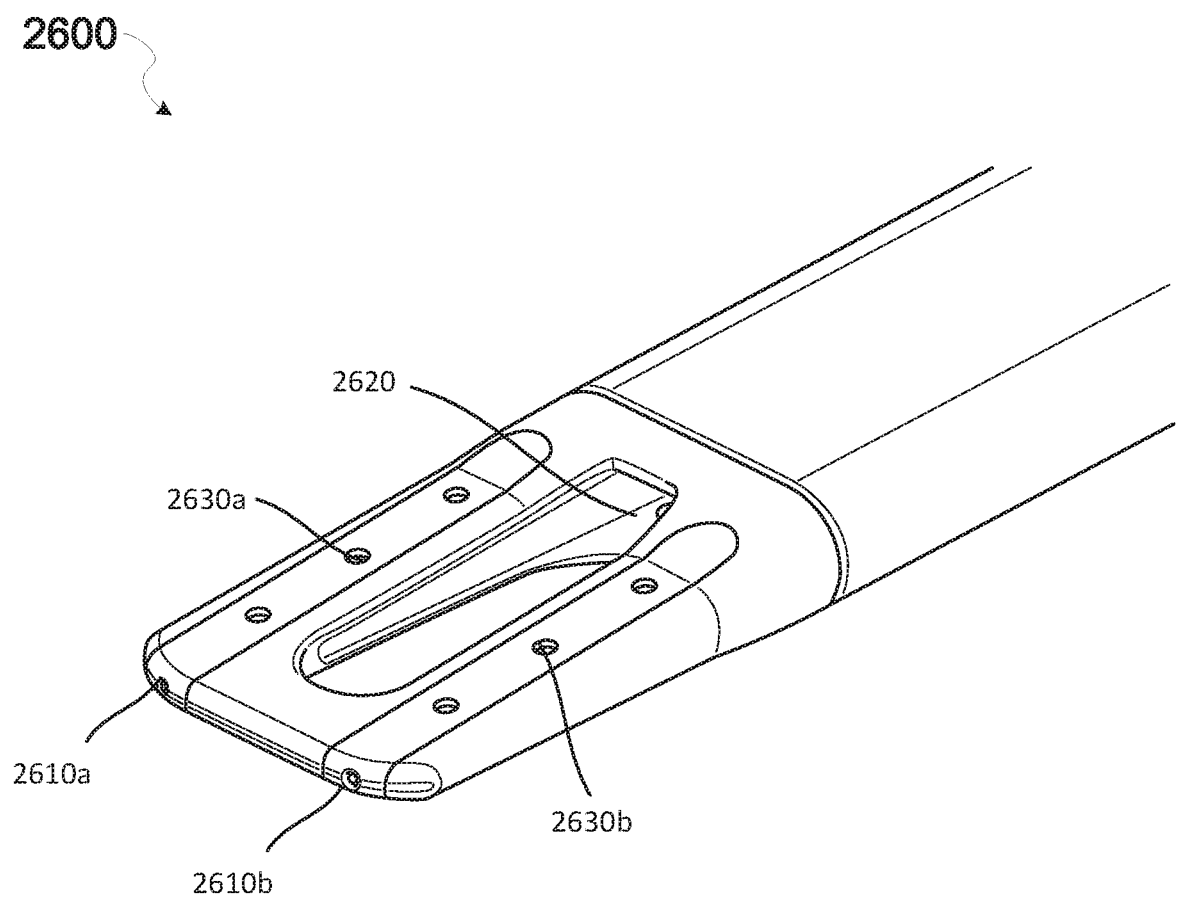
FIG. 26 provides an additional example of an end effector with a physically deflectable member to help regulate fluid flow, according to some aspects.

Referring to FIG. 26, illustration 2600 provides an additional example of an end effector with a physically deflectable member to help regulate fluid flow, according to some aspects. As shown, the end effector of illustration 2600 is shaped in a bendable and flat configuration, similar to a spatula. The middle is hollow, to allow space for the suction port 2620. Electrodes 2610*a* and 2610*b* are located at the end of the end effector, while fluid ports, such as ports 2630*a* and 2630*b*, are spaced along the bendable portion of the end effector. In this example, there are a total of 12 fluid ports, six on the top and six on the bottom. In other examples not shown, fluid ports may also be positioned at the distal end of the end effector, while the electrodes may be positioned at other strategic locations.

Figure 27:
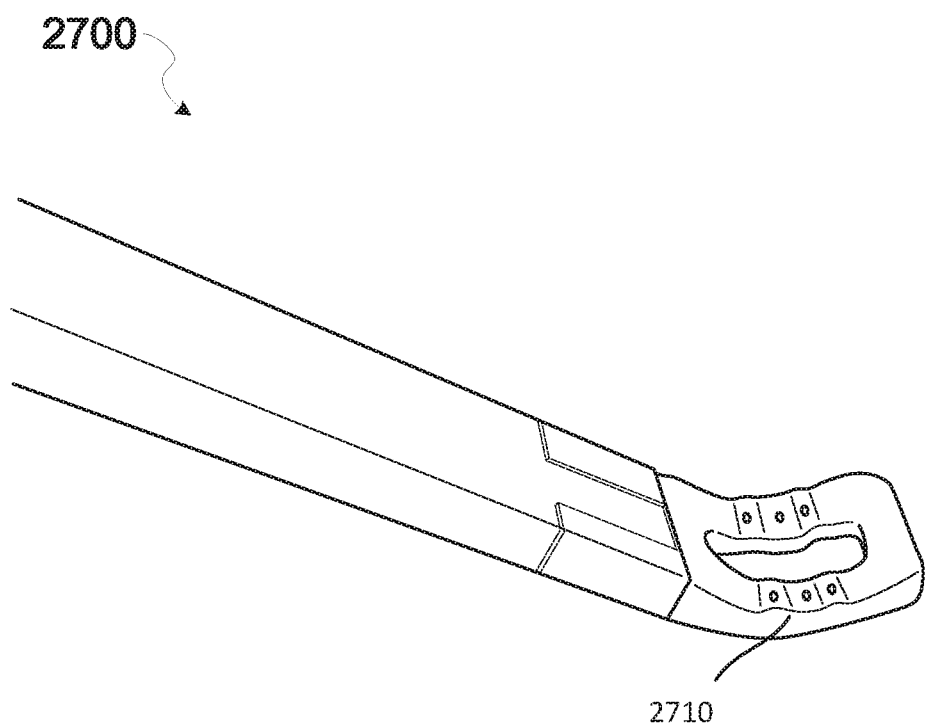
FIG. 27 provides an example of how this physically deflectable member of FIG. 26 may appear and operate when deflected by pressing against a surface.

Referring to FIG. 27, illustration 2700 provides an example of how this physically deflectable member may appear and operate when deflected by pressing against a surface. The deflected portion is shown at position 2710. In some aspects, a minimum flow or "weep" of saline automatically flows even when the end effector is not deflected. In some aspects, increasing the deflection of the end effector operates the fluid valve such that more fluid flows with increasing deflection. In some aspects, this physical deflection may be combined with other mechanisms that control the flow of saline.

Figure 28:
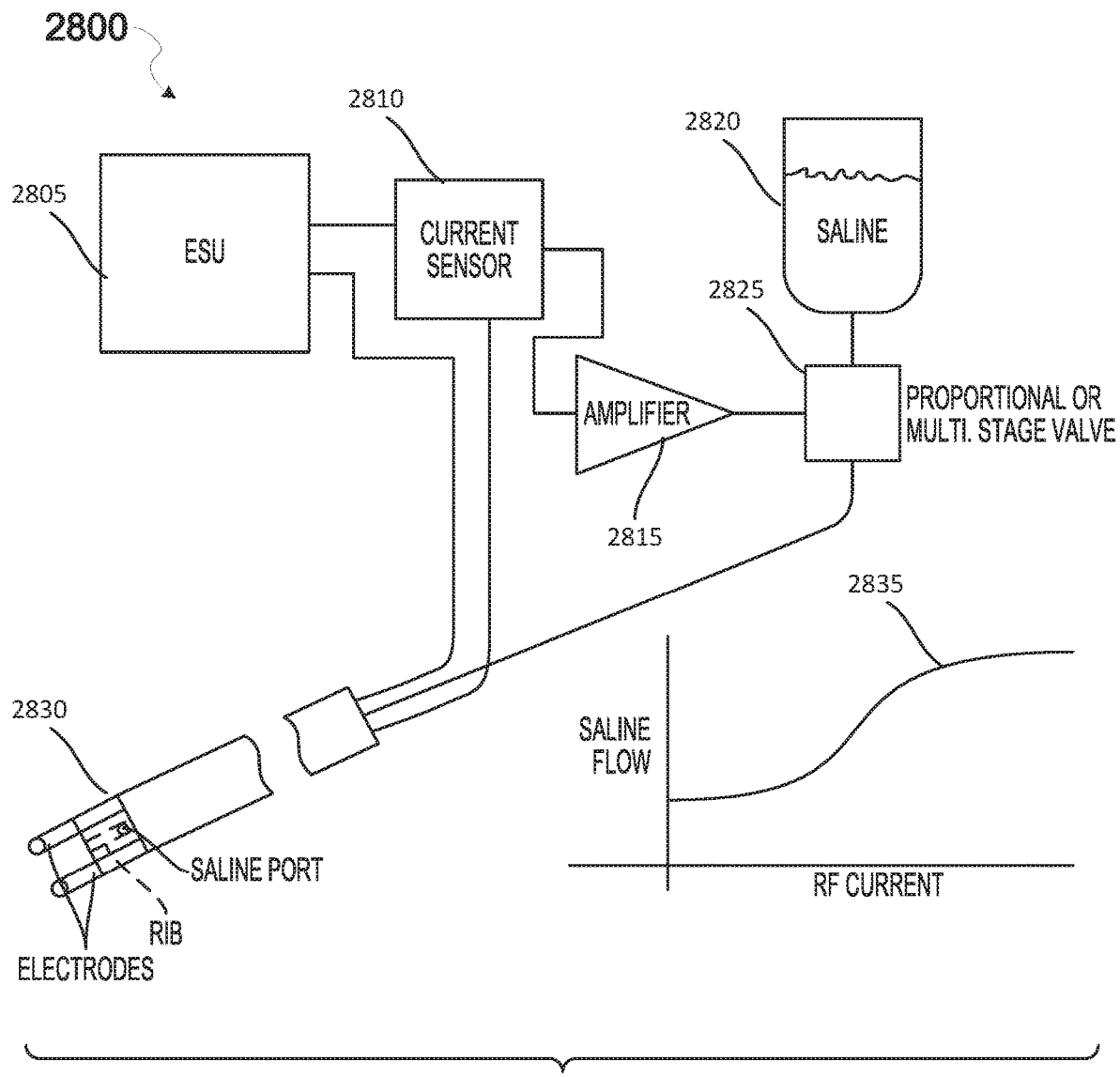
FIG. 28 shows a block diagram of various functional components of an electrosurgical system configured to vary the saline flow at the end effector based on measured RF current, according to some aspects.

Referring to FIG. 28, illustration 2800 shows a block diagram of various functional components of an electrosurgical system configured to vary the saline flow at the end effector 2830 based on measured RF current, according to some aspects. The electrosurgical system includes an electrosurgical unit (ESU) 2805 that is configured to provide power to the system. At least one current sensor 2810 is coupled to the ESU 2805 and is configured to measure an amount of RF current that is being supplied by the ESU 2005. The RF current may be dictated by one or more mechanisms on the electrosurgical device (e.g. device 100), and may be controlled at least in part by a human user operating the device. In some aspects, an amplifier 2815 is configured to magnify the signal of the current sensor to feed into a proportional or multistage valve 2825. The amount of RF current, as expressed through the amplifier 2815, can be used to control the proportional or multistage valve 2825. The fluid, such as saline 2820, passes through the valve 2825 at a rate according to an amount of current provided by the ESU 2805. In some aspects, the amount of saline flow is a function of the RF current according to the graph shown in plot 2835, as just one example. In general, the amount of saline flow may be designed to appropriately match the amount of energy supplied at the electrodes of the end effector 2830, based on how much RF current is being supplied. The current may be proportional to the work being done in the tissue at the surgical site. Higher current tends to mean that the surgeon is in contact with a lot of tissue, and turning up the flow rate automatically would appropriately match the situation the surgeon is facing.

Figure 29:
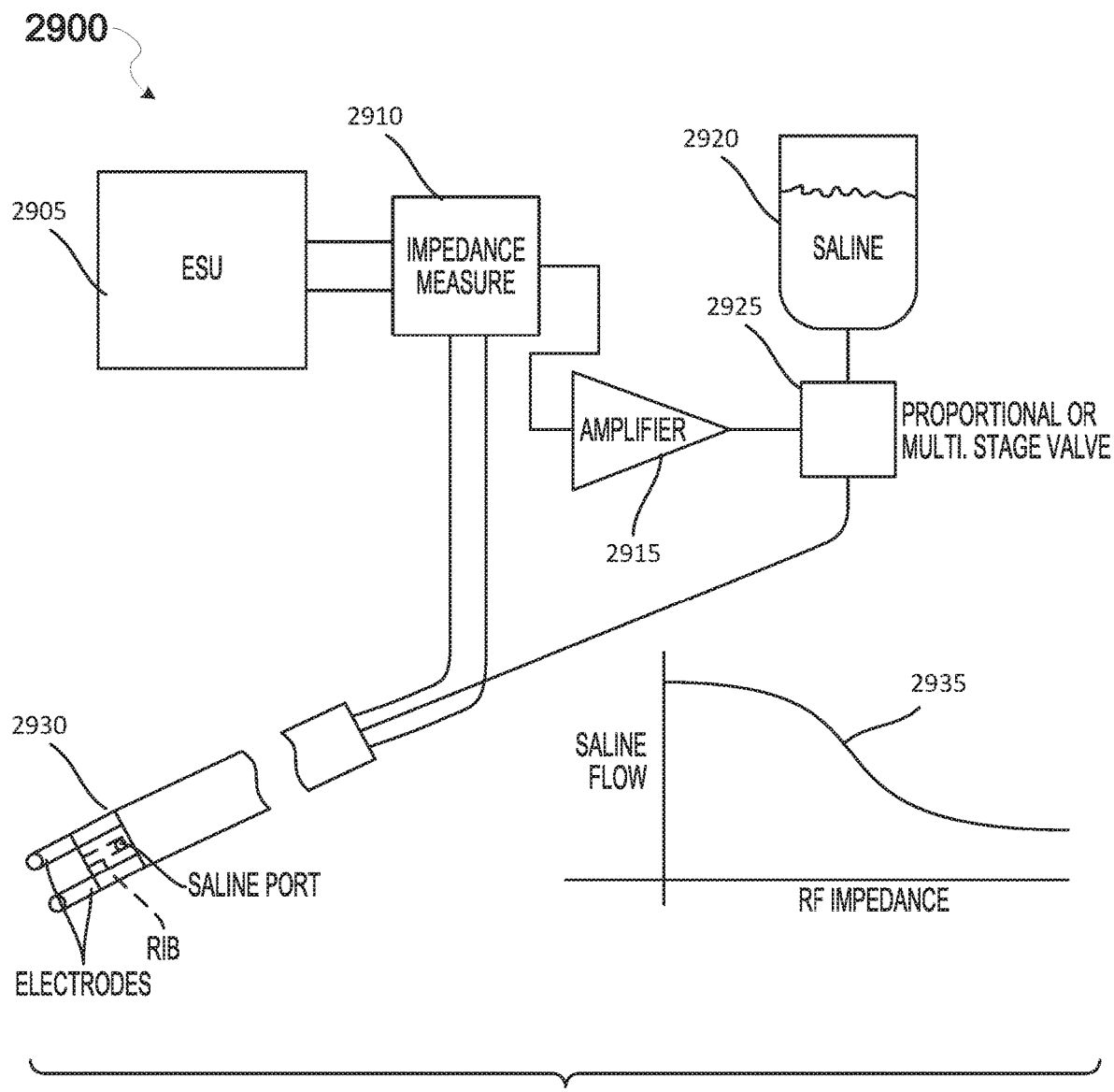
FIG. 29 shows a block diagram of various functional components of an electrosurgical system configured to vary the saline flow at the end effector, based on measured RF impedance, according to some aspects.

Referring to FIG. 29, illustration 2900 shows a block diagram of various functional components of an electrosurgical system configured to vary the saline flow at the end effector 2930, based on measured RF impedance, according to some aspects. Similar to illustration 2800, the electrosurgical system includes an ESU 2905 that is configured to provide power to the system. At least one impedance measure or monitor 2910 is coupled to the ESU 2905 and the electrosurgical device (e.g. device 100), and is configured to measure an amount of impedance experienced at the surgical site. In some aspects, the impedance monitor 2910 may include current and voltage sensor measures configured to calculate RF tissue impedance. In some aspects, an amplifier 2915 is configured to magnify the signal from the impedance measure 2910 and is fed into a proportional or multistage valve 2925. The fluid, such as saline 2920, passes through the valve 2925 at a rate according to an amount inversely proportional to the measured impedance. In some aspects, the amount of saline flow is a function of the measured RF impedance according to the graph shown in plot 2935, just as one example. In general, the amount of saline flow may be designed to appropriately counterbalance the amount of measured impedance at the surgical site. The RF impedance may be inversely proportional to the saline flow. Low tissue impedance generally implies that there is a lot of work to be done in the tissue, and saline flow should therefore be increased. Higher impedance means that the surgeon is probably in contact with less tissue or the tissue is mostly coagulated, and therefore the flow can be reduced.

Figure 30:
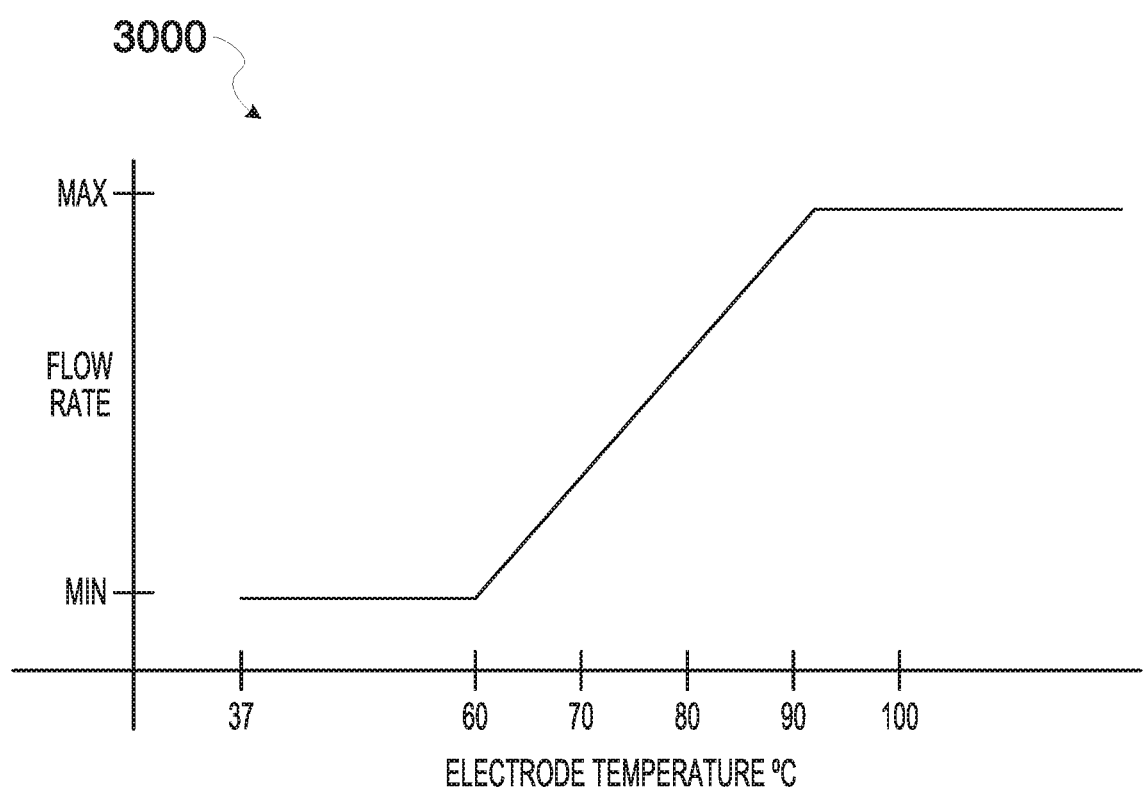
FIG. 30 shows how, in some aspects, the amount of saline flow may be measured against electrode temperature.

Referring to FIG. 30, in some aspects, the amount of saline flow may be measured against electrode temperature. Illustration 3000 shows a plot representing how a control algorithm may be configured to vary the saline flow rate based on measured temperature of the electrodes during surgery. In this example, there are predetermined minimums and maximums of the flow rate, and the flow rate may vary in a linear proportion as the temperature increases from 60° C. to 90° C. One or more temperature sensors may be communicatively coupled to one or more of the electrodes at an end effector, which may be coupled to a proportional or multistage valve (e.g., valves 2825 or 2925), which may be used to control the flow of saline through it. In some aspects, the control system may be configured to monitor temperature in addition to one or more of tissue impedance and RF current. That is, multiple types of sensors may be included in the control system, such that the flow rate of saline may be varied according to any of these different measurements. In some aspects, a user of the system may be able to specify which sensors would control the flow rate.

Figure 31:
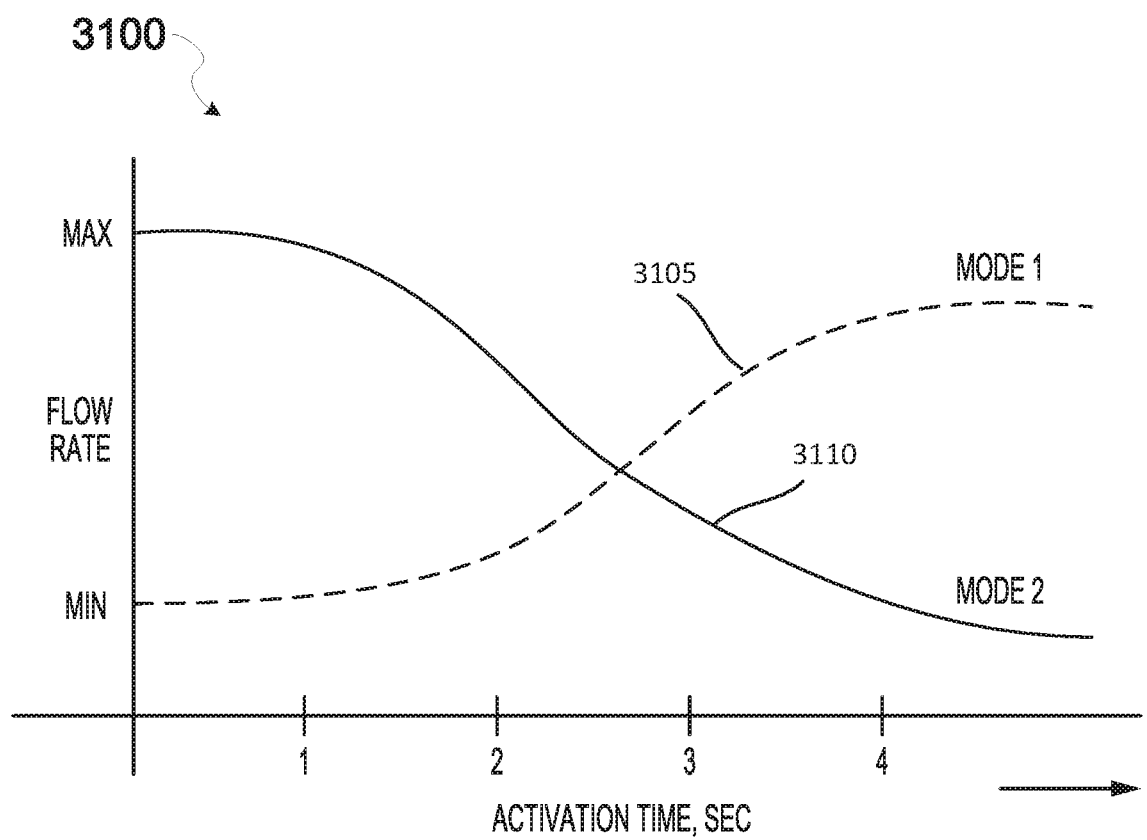
FIG. 31 shows how, in some aspects, the saline flow may depend on activation time of the electrodes.

Referring to FIG. 31, in some aspects, the saline flow may depend on activation time of the electrodes. Illustration 3100 shows a plot of two different modes that reflect different amounts of saline flow for a given amount of activation time. In certain modes of operation, saline flow is increased over a given activation time in order to provide more irrigation as the surgeon is working at the surgical site. This concept is reflected by the curve 3105 of mode 1. In this case, the amount of saline is provided substantially after a couple seconds of activation time have elapsed, reflecting providing more fluid after a brief amount of time of the electrodes working at the surgical site. Mode 1 reflects providing more fluid to cool the surgical site in order to satisfy a need that is developing at that very moment. In other modes of operation, saline flow starts at a maximum rate at the beginning of activation, and then decreases to a minimum. This provides maximum irrigation during the very first part of tissue contact and decreases as less saline is required to aid in the coagulation function. This is reflected graphically in the curve 3110 of mode 2. In some aspects, in activation button or other mechanism for activating the RF is tied to a proportional or multistage variable valve that controls the flow of saline (e.g., valves 2825 or 2925). As the activation time increases, the control signal to the valve changes to either increase or decrease the flow according to the setting of either mode 1 or mode 2, respectively.

Figure 32:
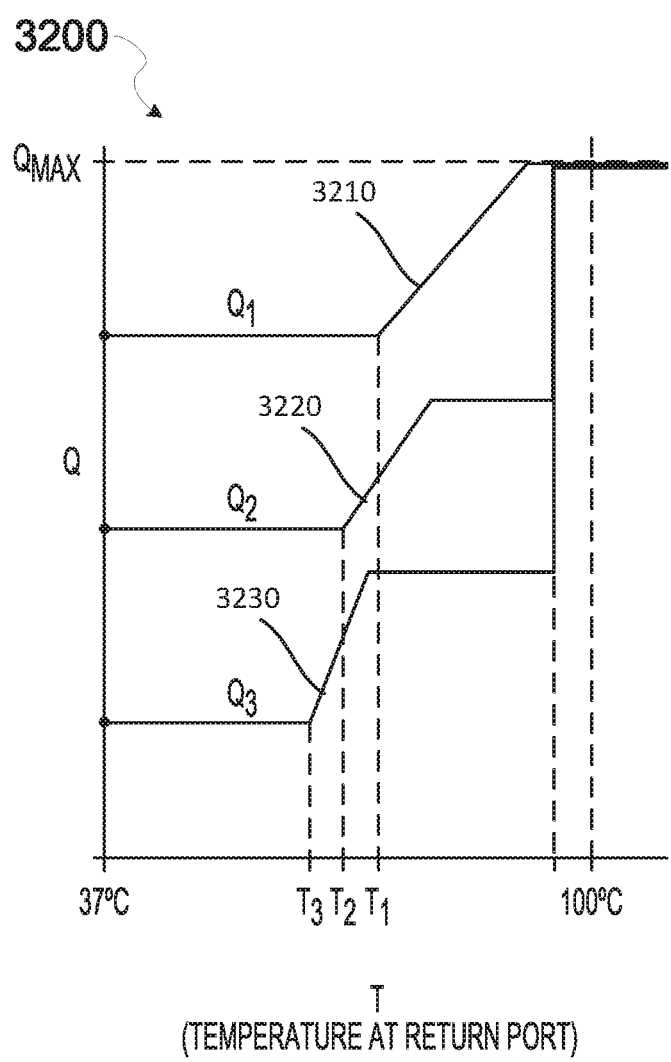
FIG. 32 shows how, in some aspects, at least a portion of the flow rate may be adjustable by the user, while other portions thereafter may be adjusted automatically.

Referring to FIG. 32, in some aspects, at least a portion of the flow rate may be adjustable by the user, while other portions thereafter may be adjusted automatically. Illustration 3200 provides a graph of 3 different plots 3210, 3220, and 3230, showing how an initial flow rate can be set manually and then adjusted automatically thereafter. In this case, the temperature of the return port, e.g., the suction port, is monitored. A user first sets a nominal flow rate, shown as the lower horizontal line in each of the three plots 3210, 3220, and 3230. As return temperature increases, the flow may be increased automatically to compensate for the higher temperature return fluid and to keep the coagulation and tissue effect at or near a desired temperature. This is reflected in the rise of lines in each of the plots after the 1st horizontal lines. In this example, the settings initially at lower temperatures start rising at an earlier increase in temperature (e.g., T3, T2, and T1, respectively, where T3<T2<T1). If ever the measure temperature at the return port reaches a near maximum temperature, the flow rate may then be increased to a maximum in response, for all cases, as shown in illustration 3200. In some aspects, this concept to partially manually select and partially auto adjust may be applied to different measurements, such as temperature of the electrodes, tissue impedance, or RF current. In other words, the concept of enabling a portion of the control system to be manually selectable may be applied to any of the previous control systems described herein.

Figure 33:
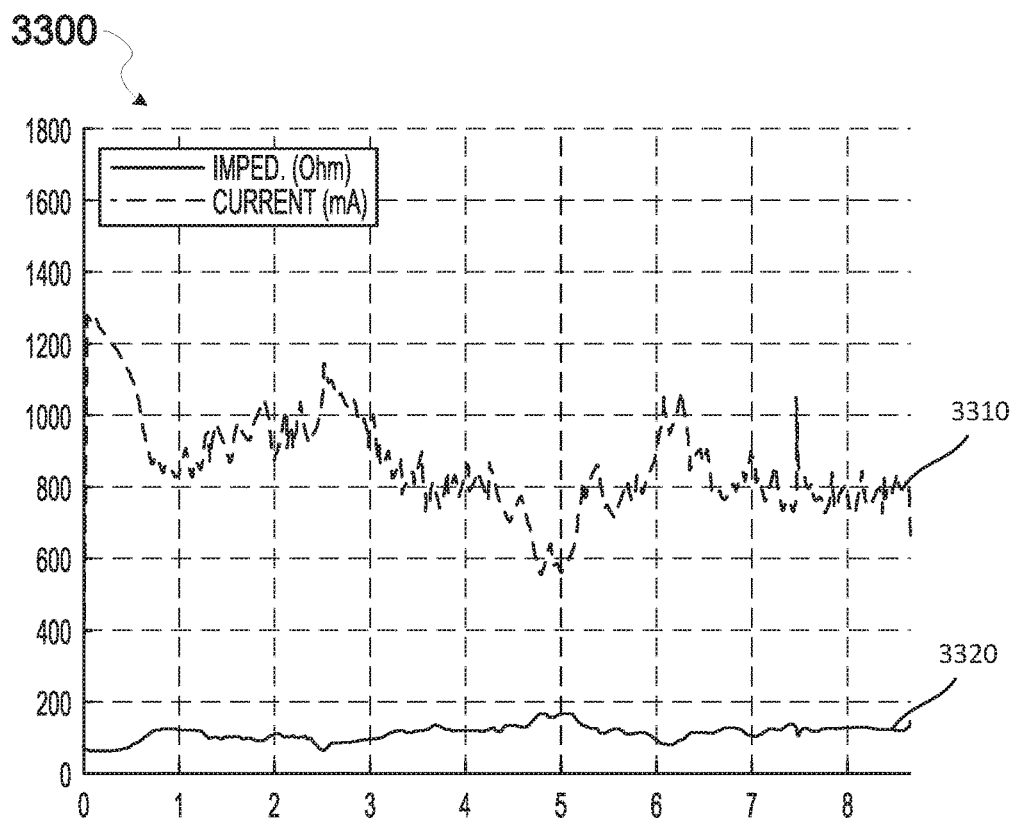
FIG. 33 provides a data plot of both a level of impedance and of current at a surgical site over time, where the data plot shows a smooth impedance line over time, indicating no sticking at the surgical site.
Figure 34:
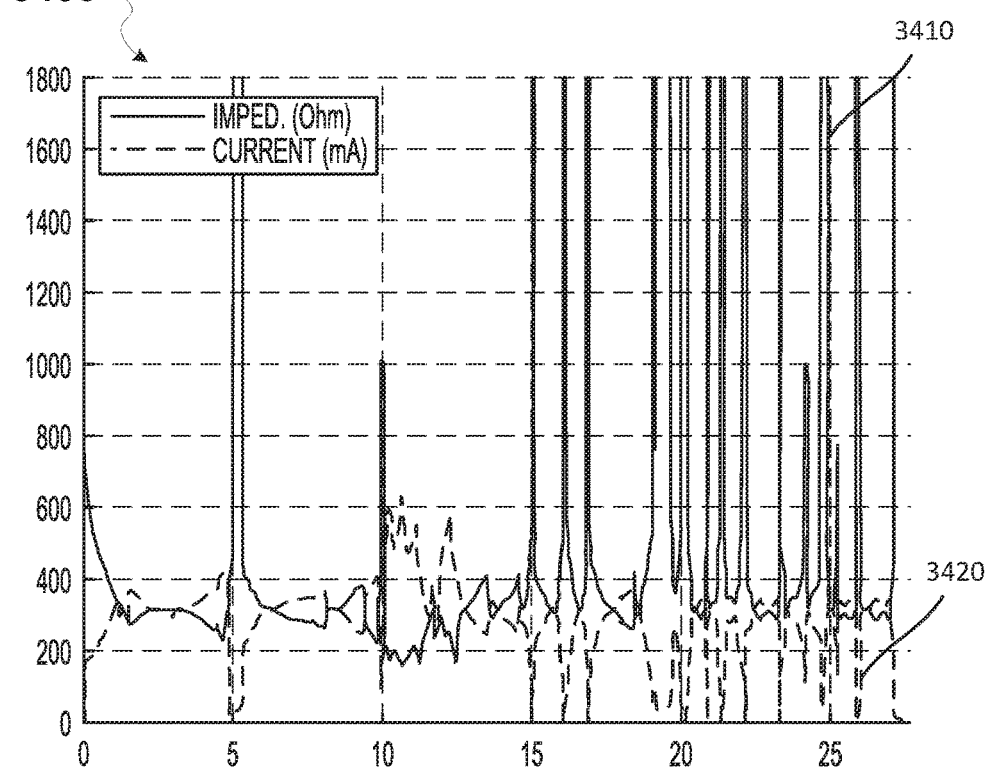
FIG. 34 shows a data plot including a large number of impedance spikes, along with a plot of the current, over time.

Referring to FIGS. 33 and 34, in some aspects, a control system to manage the fluid flow of an electrosurgical system may also be configured to monitor impedance spikes in order to prevent or reduce the occurrence of the electrodes sticking to the tissue at the surgical site. In general, keeping the electrodes cool and lubricated with fluid, such as saline, helps reduce the occurrence of sticking. Increasing the flow of saline as appropriate, according to various indicia, will offset heat generated at the surgical site and prevent or at least reduce the occurrence of sticking. One notable sign is an impedance spike. It has been observed that sudden spikes in the impedance are a precursor and an indicator of sticking. Thus, in some aspects, the control system may be configured to adjust the flow to increase automatically upon observation of an impedance spike. FIG. 33 provides a data plot 3300 of both a level of impedance 3320 and of current 3310 at a surgical site over time. Data plot 3300 shows a smooth impedance line over time, indicating no sticking at the surgical site.

In contrast, referring to FIG. 34, data plot 3400 shows a large number of impedance spikes (e.g., spike 3410, etc.), along with a plot of the current, over time. A control system may be configured to determine whenever an amount of impedance drastically increases over a short amount of time, say over one or two sampling points. This is highly likely to represent an impedance spike, and as a result, the control system may be configured to automatically increase the flow of saline or other fluid automatically. It is noted that this conditional check occurring in the control system can be implemented with any of the other control algorithms described herein. That is, the control system may be configured to perform normally according to any of the other conditions described in the control algorithms previously, and then may perform an override procedure to automatically increase the flow of saline or other fluid when an impedance spike is detected.

Still referring to FIG. 34, is worth noting that the current plot 3420 shows corresponding drops in current whenever there are impedance spikes. This makes sense because of the general inverse nature of impedance to current, and also when contemplating the fact that an impedance spike tends to suggest that a circuit through the electrodes and he surgical site cannot be completed anymore, there by causing a drop in the current reading. As such, in some aspects, the control system may be configured to monitor sudden drops in current while power is still being applied, as an alternative or additional way to determine when to automatically increase the flow of saline or other fluid.

Aspects of the present disclosure also include methods for controlling the suction functionality of the electrosurgical device in order to vary the amount of suction applied at the surgical site. In general, it is desirable to generate an amount of suction that is portion it to the amount of fluid at the surgical site. A rate of suction that is constant may fail to account for a sufficient number of scenarios that have varying amounts of fluid flow. Too much vacuum may not allow the intended tissue to coagulate, which then allows the tissue to dry out quickly, causing the electrodes to stick to the tissue. Too little vacuum tends to leave extra saline unattended at the tissue surface, which then leads to unintended extra surface burning. In general, it is desirable to change the rate of suction at an amount or frequency that is appropriate to the other factors at the surgical site, such as the amount of saline flowing and the temperature in the target tissue or at the surgical site generally.

Thus, in some aspects, the suction can be modulated on and off with a variable duty cycle and rate, such as two seconds on one second off, which can repeat. This is an example of a 66% duty cycle at a three second rate. This can be accomplished, for example, by turning on and off the vacuum order, opening and closing bypass valves, opening and closing direct valves on the vacuum line, and so forth. A control system may be configured to control these different mechanisms according to a control algorithm that specifies an appropriate variable duty cycle rate. The duty cycle rate may be changeable by the control system, in order to increase or decrease the amount of suction.

In some aspects, the suction can be modulated as a function of the power settings on the generator or a measure of the power delivered to the tissue. For example, an increase of power would result in a corresponding increase in the suction. This increase, or any change in the suction, can be accomplished by changing the rate and duty cycle as previously described, or by increasing or decreasing apertures, remote from the tissue site, on the vacuum line that effectively bypasses the suction at the tissue site. In general, the control system may be configured to manipulate the duty cycle rate and/or the control of these apertures.

Figure 35:
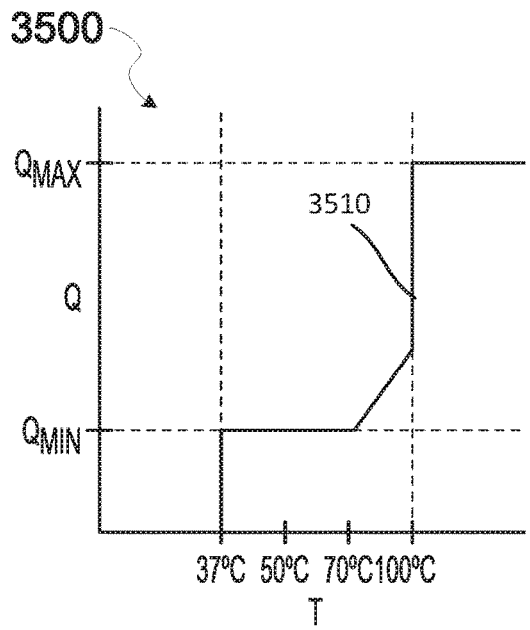
FIG. 35 shows a data plot of an example of automatic adjustment of fluid flow rate (Q) as a function of the measured temperature of exiting fluid (T).
Figure 36:
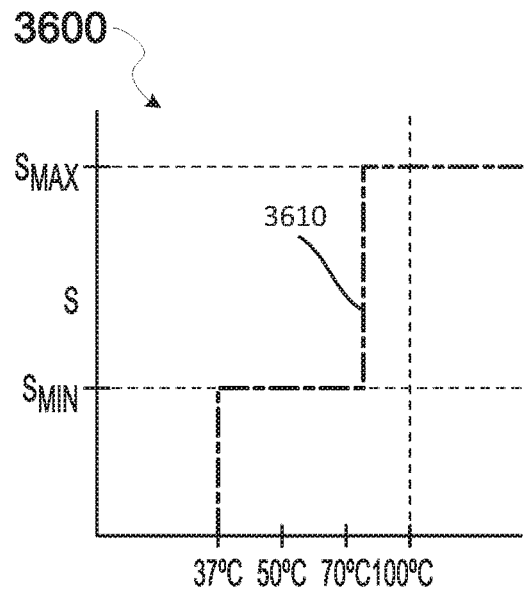
FIG. 36 shows a data plot of an example of automatic adjustment of suction (S) as a function of the measured temperature of exiting fluid (T).
Figure 37:
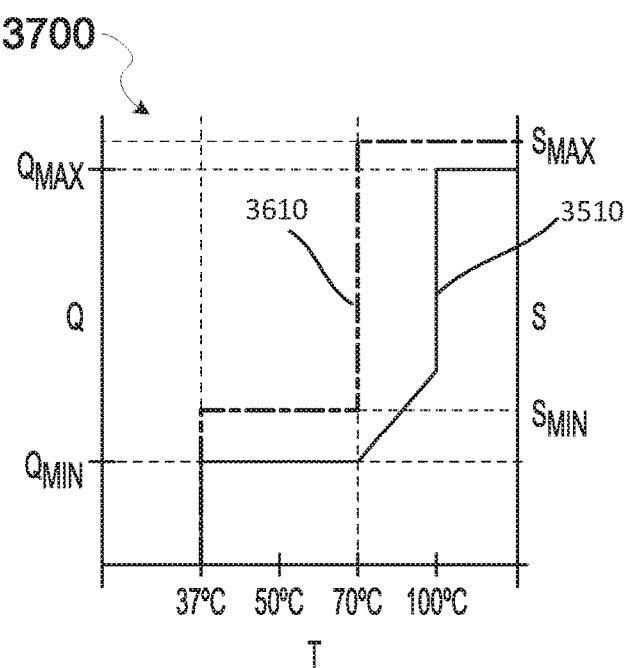
FIG. 37 shows a superposition of the data plots of FIG. 35 and FIG. 36.

Referring to FIGS. 35-37, shown are plots that illustrate how a rate of suction can correspond to a rate of fluid flow, according to some aspects. In FIG. 35, plot 3500 shows an example of automatic adjustment of the fluid flow rate (Q), as a function of measured temperature of exiting fluid (T). The solid line 3510 shows that the rate of fluid starts at a minimum at certain measured low temperatures. The flow rate may increase steadily once the temperature is measured between 70 to 100° C. The flow rate may then be set to a maximum upon reaching a maximum temperature of 100° C. This is just one example of how the flow rate may be automatically adjusted, and other control algorithms as described above may also apply here.

Referring to FIG. 36, plot 3600 shows an example of automatic adjustment of the suction (S), as a function of the measured temperature of exiting fluid (T). The dashed and dotted line 3610 shows that the rate of suction starts at a minimum at certain measured low temperatures. The suction rate may increase to be at a maximum prior to reaching a maximum fluid temperature, as shown.

Referring to FIG. 37, plot 3700 shows a superposition of the two lines 3510 and 3610 to illustrate more clearly the interactions between the rate of suction and the rate of fluid flow, according to some aspects. In this example, it can be seen that the minimum rate of suction is higher than the minimum flow rate, and the maximum suction rate is higher than the maximum flow rate. Also, all temperatures, the rate of suction is generally higher than the rate of fluid flow. However, the rate of suction is not drastically higher than the rate of fluid flow at any given temperature, which reflects the desire to sufficiently vacuum the fluid but not drastically so that the surgical site gets to hot and burns.

Figure 38:
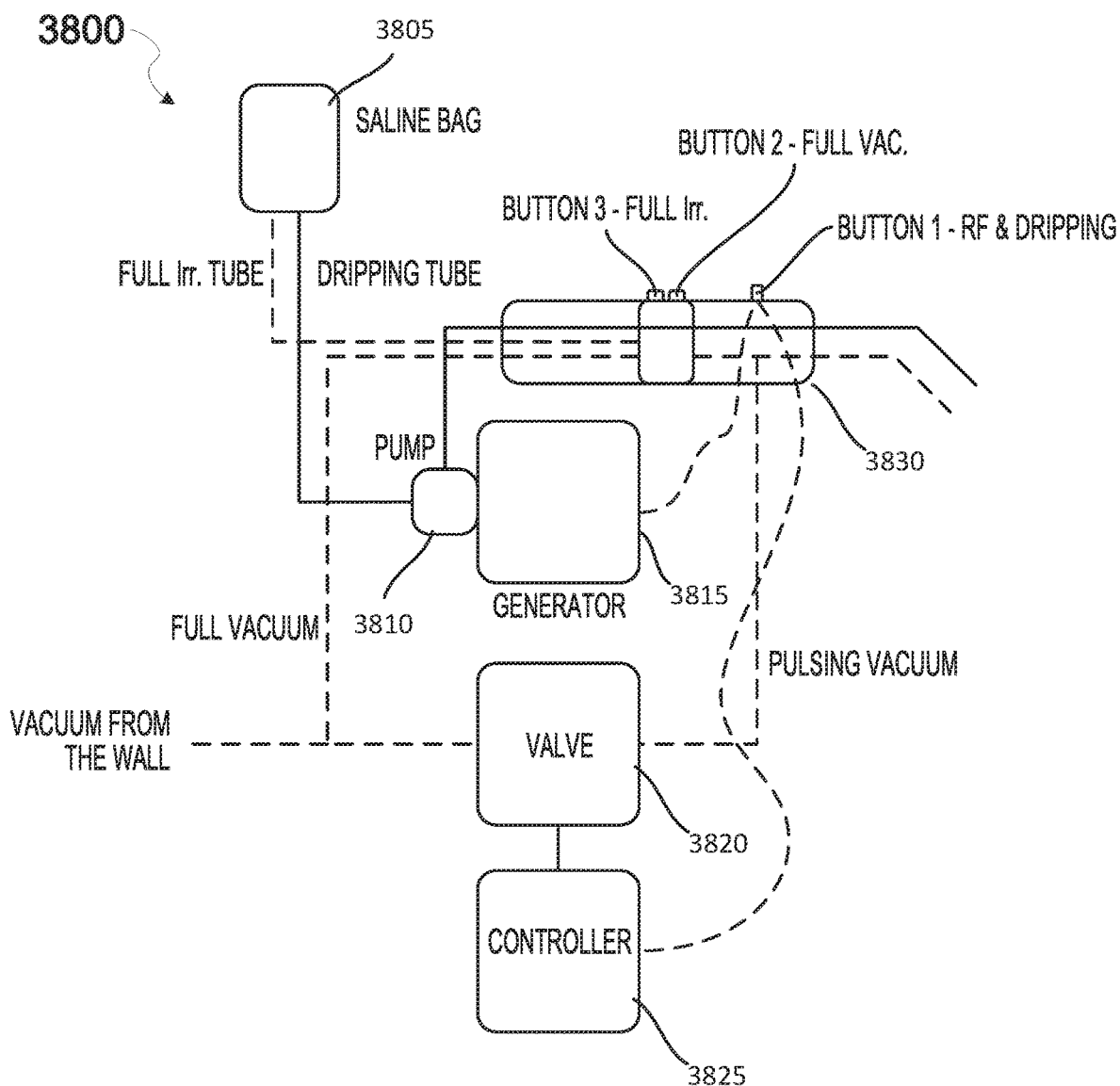
FIG. 38 shows a block diagram of an example of functional elements that are used in implementing a control system for managing fluid flow and suction.

Referring to FIG. 38, block diagram 3800 provides one example of functional elements that are used in implementing a control system for managing fluid flow and suction, according to some aspects of the present disclosure. In this example, a fluid source, such as saline bag 3805 is fluidically coupled to the electrosurgical device 3830. In this example, there are two tubes connected to the saline bag 3805: a full irrigation tube and a dripping tube. The full irrigation tube may allow for steady flow of the fluid directly into the electrosurgical device 3830. This may be accessed when maximum fluid flow is desired. In other cases, the dripping tube may be used, which is connected to a pump 3810 that is controlled by a generator 3815. The generator 3815 may be activated by a button or switch on the electrosurgical device, e.g., button 1 as shown. In some cases, the switch may be a dial or keypad that allows the user to select multiple options for more specific settings to control the flow rate. In this example, another button, e.g., button 3, may be used to enable the full irrigation functionality. In other cases, a single button or switch may be used to activate irrigation generally, which may be tied to the generator 3815 as well as the full irrigation tube. In other cases, a single button or switch may be used to activate irrigation through a single flow tube from the saline bag 3005, in which a pump 3810 and a generator 3815 may be used to control all flow rates, including enabling full irrigation. Examples of these systems are described in previous figures, above.

Still referring to FIG. 38, the vacuum or aspiration system may include a vacuum source, such as a vacuum from the wall, and a valve 3820 and controller 3825. The vacuum source may come from a generator and is plugged into a wall, as an alternative example. In this example, the electrosurgical device 3830 allows for two paths of enabling the vacuum functionality: a full vacuum path and the pulsing vacuum path. In this example, a tube running directly from the vacuum is connected to the electrosurgical device 3830 to allow for maximum vacuum functionality. A separate tube may connect from the valve 3822 another port and the electrosurgical device 3830 to allow for pulsing vacuum functionality. The controller 3825 may be configured to control the valve 3820, to allow for a ratio of opening and closing of the valve 3820 to mimic or simulate pulsing vacuuming, which may effectively produce varying or fractional amounts of the suction. In this example, button 1 may control the pulsing vacuum functionality, as it is connected to the controller 3025. Button 2 may control the full vacuum functionality. In other examples, a single button or switch may be used to activate the vacuum or suction generally, which may be tied to the controller 3025 as well as a full vacuum tube. In this way, the valve 3820 may be configured to allow for full suction when it is completely open, as well as fractional rates of suction due to the controller 3825 creating a duty cycle rate of opening and closing, or by having the valve 3820 include or be a part of multiple valves that can be opened to relieve vacuum pressure. Examples of these systems are described in previous figures, above.

It will be appreciated that the terms "proximal" and "distal" are used throughout the specification with reference to a clinician manipulating one end of an instrument used to treat a patient. The term "proximal" refers to the portion of the instrument closest to the clinician and the term "distal" refers to the portion located furthest from the clinician. It will further be appreciated that for conciseness and clarity, spatial terms such as "vertical," "horizontal," "up," or "down" may be used herein with respect to the illustrated aspects. However, surgical instruments may be used in many orientations and positions, and these terms are not intended to be limiting or absolute.

Various aspects of surgical instruments are described herein. It will be understood by those skilled in the art that the various aspects described herein may be used with the described surgical instruments. The descriptions are provided for example only, and those skilled in the art will understand that the disclosed examples are not limited to only the devices disclosed herein, but may be used with any compatible surgical instrument or robotic surgical system.

Reference throughout the specification to "various aspects," "some aspects," "one example," "one aspect," "an aspect," "one form," or "a form" means that a particular feature, structure, or characteristic described in connection with the aspect is included in at least one example. Thus, appearances of the phrases "in various aspects," "in some aspects," "in one example," or "in one aspect" in places throughout the specification are not necessarily all referring to the same aspect. Furthermore, the particular features, structures, or characteristics illustrated or described in connection with one example may be combined, in whole or in part, with features, structures, or characteristics of one or more other aspects without limitation.

While various aspects herein have been illustrated by description of several aspects and while the illustrative aspects have been described in considerable detail, it is not the intention of the applicant to restrict or in any way limit the scope of the appended claims to such detail. Additional advantages and modifications may readily appear to those skilled in the art. For example, it is generally accepted that endoscopic procedures are more common than laparoscopic procedures. Accordingly, the present invention has been discussed in terms of endoscopic procedures and apparatus. However, use herein of terms such as "endoscopic", should not be construed to limit the present invention to an instrument for use only in conjunction with an endoscopic tube (e.g., trocar). On the contrary, it is believed that the present invention may find use in any procedure where access is limited to a small incision, including but not limited to laparoscopic procedures, as well as open procedures.

It is to be understood that at least some of the figures and descriptions herein have been simplified to illustrate elements that are relevant for a clear understanding of the disclosure, while eliminating, for purposes of clarity, other elements. Those of ordinary skill in the art will recognize, however, that these and other elements may be desirable. However, because such elements are well known in the art, and because they do not facilitate a better understanding of the disclosure, a discussion of such elements is not provided herein.

While several aspects have been described, it should be apparent, however, that various modifications, alterations and adaptations to those aspects may occur to persons skilled in the art with the attainment of some or all of the advantages of the disclosure. For example, according to various aspects, a single component may be replaced by multiple components, and multiple components may be replaced by a single component, to perform a given function or functions. This application is therefore intended to cover all such modifications, alterations and adaptations without departing from the scope and spirit of the disclosure as defined by the appended claims.

Any patent, publication, or other disclosure material, including, but not limited to U.S. patents, U.S. patent application publications, U.S. patent applications, foreign patents, foreign patent applications, non-patent publications referred to in this specification and/or listed in any Application Data Sheet, or any other disclosure material are incorporated herein by reference in whole or in part, is incorporated herein only to the extent that the incorporated materials does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

While various details have been set forth in the foregoing description, it will be appreciated that the various aspects of the techniques for operating a generator for digitally generating electrical signal waveforms and surgical instruments may be practiced without these specific details. One skilled in the art will recognize that the herein described components (e.g., operations), devices, objects, and the discussion accompanying them are used as examples for the sake of conceptual clarity and that various configuration modifications are contemplated. Consequently, as used herein, the specific exemplars set forth and the accompanying discussion are intended to be representative of their more general classes. In general, use of any specific exemplar is intended to be representative of its class, and the non-inclusion of specific components (e.g., operations), devices, and objects should not be taken limiting.

Further, while several forms have been illustrated and described, it is not the intention of the applicant to restrict or limit the scope of the appended claims to such detail. Numerous modifications, variations, changes, substitutions, combinations, and equivalents to those forms may be implemented and will occur to those skilled in the art without departing from the scope of the present disclosure. Moreover, the structure of each element associated with the described forms can be alternatively described as a means for providing the function performed by the element. Also, where materials are disclosed for certain components, other materials may be used. It is therefore to be understood that the foregoing description and the appended claims are intended to cover all such modifications, combinations, and variations as falling within the scope of the disclosed forms. The appended claims are intended to cover all such modifications, variations, changes, substitutions, modifications, and equivalents.

For conciseness and clarity of disclosure, selected aspects of the foregoing disclosure have been shown in block diagram form rather than in detail. Some portions of the detailed descriptions provided herein may be presented in terms of instructions that operate on data that is stored in one or more computer memories or one or more data storage devices (e.g. floppy disk, hard disk drive, Compact Disc (CD), Digital Video Disk (DVD), or digital tape). Such descriptions and representations are used by those skilled in the art to describe and convey the substance of their work to others skilled in the art. In general, an algorithm refers to a self-consistent sequence of steps leading to a desired result, where a "step" refers to a manipulation of physical quantities and/or logic states which may, though need not necessarily, take the form of electrical or magnetic signals capable of being stored, transferred, combined, compared, and otherwise manipulated. It is common usage to refer to these signals as bits, values, elements, symbols, characters, terms, numbers, or the like. These and similar terms may be associated with the appropriate physical quantities and are merely convenient labels applied to these quantities and/or states.

Unless specifically stated otherwise as apparent from the foregoing disclosure, it is appreciated that, throughout the foregoing disclosure, discussions using terms such as "processing" or "computing" or "calculating" or "determining" or "displaying" or the like, refer to the action and processes of a computer system, or similar electronic computing device, that manipulates and transforms data represented as physical (electronic) quantities within the computer system's registers and memories into other data similarly represented as physical quantities within the computer system memories or registers or other such information storage, transmission or display devices.

In a general sense, those skilled in the art will recognize that the various aspects described herein which can be implemented, individually and/or collectively, by a wide range of hardware, software, firmware, or any combination thereof can be viewed as being composed of various types of "electrical circuitry." Consequently, as used herein "electrical circuitry" includes, but is not limited to, electrical circuitry having at least one discrete electrical circuit, electrical circuitry having at least one integrated circuit, electrical circuitry having at least one application specific integrated circuit, electrical circuitry forming a general purpose computing device configured by a computer program (e.g., a general purpose computer configured by a computer program which at least partially carries out processes and/or devices described herein, or a microprocessor configured by a computer program which at least partially carries out processes and/or devices described herein), electrical circuitry forming a memory device (e.g., forms of random access memory), and/or electrical circuitry forming a communications device (e.g., a modem, communications switch, or optical-electrical equipment). Those having skill in the art will recognize that the subject matter described herein may be implemented in an analog or digital fashion or some combination thereof.

The foregoing detailed description has set forth various forms of the devices and/or processes via the use of block diagrams, flowcharts, and/or examples. Insofar as such block diagrams, flowcharts, and/or examples contain one or more functions and/or operations, it will be understood by those within the art that each function and/or operation within such block diagrams, flowcharts, and/or examples can be implemented, individually and/or collectively, by a wide range of hardware, software, firmware, or virtually any combination thereof. In one form, several portions of the subject matter described herein may be implemented via an application specific integrated circuits (ASIC), a field programmable gate array (FPGA), a digital signal processor (DSP), or other integrated formats. However, those skilled in the art will recognize that some aspects of the forms disclosed herein, in whole or in part, can be equivalently implemented in integrated circuits, as one or more computer programs running on one or more computers (e.g., as one or more programs running on one or more computer systems), as one or more programs running on one or more processors (e.g., as one or more programs running on one or more microprocessors), as firmware, or as virtually any combination thereof, and that designing the circuitry and/or writing the code for the software and or firmware would be well within the skill of one of skill in the art in light of this disclosure. In addition, those skilled in the art will appreciate that the mechanisms of the subject matter described herein are capable of being distributed as one or more program products in a variety of forms, and that an illustrative form of the subject matter described herein applies regardless of the particular type of signal bearing medium used to actually carry out the distribution. Examples of a signal bearing medium include, but are not limited to, the following: a recordable type medium such as a floppy disk, a hard disk drive, a Compact Disc (CD), a Digital Video Disk (DVD), a digital tape, a computer memory, etc.; and a transmission type medium such as a digital and/or an analog communication medium (e.g., a fiber optic cable, a waveguide, a wired communications link, a wireless communication link (e.g., transmitter, receiver, transmission logic, reception logic, etc.), etc.).

In some instances, one or more elements may be described using the expression "coupled" and "connected" along with their derivatives. It should be understood that these terms are not intended as synonyms for each other. For example, some aspects may be described using the term "connected" to indicate that two or more elements are in direct physical or electrical contact with each other. In another example, some aspects may be described using the term "coupled" to indicate that two or more elements are in direct physical or electrical contact. The term "coupled," however, also may mean that two or more elements are not in direct contact with each other, but yet still co-operate or interact with each other. It is to be understood that depicted architectures of different components contained within, or connected with, different other components are merely examples, and that in fact many other architectures may be implemented which achieve the same functionality. In a conceptual sense, any arrangement of components to achieve the same functionality is effectively "associated" such that the desired functionality is achieved. Hence, any two components herein combined to achieve a particular functionality can be seen as "associated with" each other such that the desired functionality is achieved, irrespective of architectures or intermedial components. Likewise, any two components so associated also can be viewed as being "operably connected," or "operably coupled," to each other to achieve the desired functionality, and any two components capable of being so associated also can be viewed as being "operably couplable," to each other to achieve the desired functionality. Specific examples of operably couplable include but are not limited to physically mateable and/or physically interacting components, and/or wirelessly interactable, and/or wirelessly interacting components, and/or logically interacting, and/or logically interactable components, and/or electrically interacting components, and/or electrically interactable components, and/or optically interacting components, and/or optically interactable components.

In other instances, one or more components may be referred to herein as "configured to," "configurable to," "operable/operative to," "adapted/adaptable," "able to," "conformable/conformed to," etc. Those skilled in the art will recognize that "configured to" can generally encompass active-state components and/or inactive-state components and/or standby-state components, unless context requires otherwise.

While particular aspects of the present disclosure have been shown and described, it will be apparent to those skilled in the art that, based upon the teachings herein, changes and modifications may be made without departing from the subject matter described herein and its broader aspects and, therefore, the appended claims are to encompass within their scope all such changes and modifications as are within the true scope of the subject matter described herein. It will be understood by those within the art that, in general, terms used herein, and especially in the appended claims (e.g., bodies of the appended claims) are generally intended as "open" terms (e.g., the term "including" should be interpreted as "including but not limited to," the term "having" should be interpreted as "having at least," the term "includes" should be interpreted as "includes but is not limited to," etc.). It will be further understood by those within the art that if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to claims containing only one such recitation, even when the same claim includes the introductory phrases "one or more" or "at least one" and indefinite articles such as "a" or "an" (e.g., "a" and/or "an" should typically be interpreted to mean "at least one" or "one or more"); the same holds true for the use of definite articles used to introduce claim recitations.

In addition, even if a specific number of an introduced claim recitation is explicitly recited, those skilled in the art will recognize that such recitation should typically be interpreted to mean at least the recited number (e.g., the bare recitation of "two recitations," without other modifiers, typically means at least two recitations, or two or more recitations). Furthermore, in those instances where a convention analogous to "at least one of A, B, and C, etc." is used, in general such a construction is intended in the sense one having skill in the art would understand the convention (e.g., "a system having at least one of A, B, and C" would include but not be limited to systems that have A alone, B alone, C alone, A and B together, A and C together, B and C together, and/or A, B, and C together, etc.). In those instances where a convention analogous to "at least one of A, B, or C, etc." is used, in general such a construction is intended in the sense one having skill in the art would understand the convention (e.g., "a system having at least one of A, B, or C" would include but not be limited to systems that have A alone, B alone, C alone, A and B together, A and C together, B and C together, and/or A, B, and C together, etc.). It will be further understood by those within the art that typically a disjunctive word and/or phrase presenting two or more alternative terms, whether in the description, claims, or drawings, should be understood to contemplate the possibilities of including one of the terms, either of the terms, or both terms unless context dictates otherwise. For example, the phrase "A or B" will be typically understood to include the possibilities of "A" or "B" or "A and B."

With respect to the appended claims, those skilled in the art will appreciate that recited operations therein may generally be performed in any order. Also, although various operational flows are presented in a sequence(s), it should be understood that the various operations may be performed in other orders than those which are illustrated, or may be performed concurrently. Examples of such alternate orderings may include overlapping, interleaved, interrupted, reordered, incremental, preparatory, supplemental, simultaneous, reverse, or other variant orderings, unless context dictates otherwise. Furthermore, terms like "responsive to," "related to," or other past-tense adjectives are generally not intended to exclude such variants, unless context dictates otherwise.

With respect to the use of substantially any plural and/or singular terms herein, those having skill in the art can translate from the plural to the singular and/or from the singular to the plural as is appropriate to the context and/or application. The various singular/plural permutations are not expressly set forth herein for sake of clarity.

In certain cases, use of a system or method may occur in a territory even if components are located outside the territory. For example, in a distributed computing context, use of a distributed computing system may occur in a territory even though parts of the system may be located outside of the territory (e.g., relay, server, processor, signal-bearing medium, transmitting computer, receiving computer, etc. located outside the territory).

A sale of a system or method may likewise occur in a territory even if components of the system or method are located and/or used outside the territory. Further, implementation of at least part of a system for performing a method in one territory does not preclude use of the system in another territory.

In summary, numerous benefits have been described which result from employing the concepts described herein. The foregoing description of the one or more forms has been presented for purposes of illustration and description. It is not intended to be exhaustive or limiting to the precise form disclosed. Modifications or variations are possible in light of the above teachings. The one or more forms were chosen and described in order to illustrate principles and practical application to thereby enable one of ordinary skill in the art to utilize the various forms and with various modifications as are suited to the particular use contemplated. It is intended that the claims submitted herewith define the overall scope.

Various aspects of the subject matter described herein are set out in the following numbered clauses:

Example 1

An electrosurgical device comprising: a housing; a shaft extending distally from the housing; an end effector coupled to a distal end of the shaft, the end effector comprising: an electrode; a suction port; and a fluid port; and a control system communicatively coupled to the suction port and the fluid port and configured to control a rate of fluid flowing out of the fluid port and a rate of suction flowing into the suction port.

Example 2

The electrosurgical device of Example 1, further comprising: a first fluid path in fluid communication with the fluid port; and a second fluid path in fluid communication with the suction port; wherein the housing is configured to enclose a first portion of the first fluid path and a first portion of the second fluid path; and wherein the shaft is configured to enclose a second portion of the first fluid path and a second portion of the second fluid path.

Example 3

The electrosurgical device of one or more of Examples 1-2, further comprising an impedance sensor configured to measure impedance experienced at the electrode.

Example 4

The electrosurgical device of Example 3, wherein the control system is configured to control the rate of fluid flowing out of the fluid port based on the measured impedance experienced at the electrode.

Example 5

The electrosurgical device of Example 4, wherein the control system is further configured to control the rate of suction flowing into of the suction port based on the measured impedance experienced at the electrode.

Example 6

The electrosurgical device of one or more of Examples 1-5, further comprising a radio frequency (RF) current sensor configured to measure RF current applied to the electrode.

Example 7

The electrosurgical device of Example 6, wherein the control system is configured to control the rate of fluid flowing out of the fluid port based on the measured RF current applied to the electrode.

Example 8

The electrosurgical device of Example 7, wherein the control system is further configured to control the rate of suction flowing into of the suction port based on the measured RF current applied to the electrode.

Example 9

The electrosurgical device of one or more of Examples 1-8, further comprising a temperature sensor configured to measure temperature of the fluid suctioned into the suction port.

Example 10

The electrosurgical device of Example 9, wherein the control system is configured to control the rate of fluid flowing out of the fluid port based on the measured temperature of the fluid into the suction port.

Example 11

The electrosurgical device of Example 10, wherein the control system is further configured to control the rate of suction flowing into of the suction port based on the measured temperature of the fluid into the suction port.

Example 12

The electrosurgical device of one or more of Examples 1-11, wherein the end effector further comprises a partially deflectable member that is configured to increase the rate of fluid out of the fluid port as the partially deflectable member increases in deflection.

Example 13

The electrosurgical device of one or more of Examples 1-12, wherein the control system is further configured to increase the rate of fluid flowing out of the fluid port the longer the electrode applies energy.

Example 14

The electrosurgical device of one or more of Examples 1-13, wherein the control system is further configured to decrease the rate of fluid flowing out of the fluid port the longer the electrode applies energy.

Example 15

The electrosurgical device of one or more of Examples 1-14, further comprising a user interface console communicatively coupled to the control system and configured to receive an input from a user to manually control an initial fluid rate of the fluid port.

Example 16

The electrosurgical device of Example 15, wherein the control system is further configured to automatically increase the fluid rate of the fluid port after the initial fluid rate is manually specified from the user interface console; wherein the automatic increase of the fluid rate occurs based on an earlier rise in measured temperature of the fluid at the suction port if the initial fluid rate is manually specified at a slower fluid rate, and the automatic increase of the fluid rate occurs based on a later rise in measured temperature of the fluid at the suction port if the initial fluid rate is manually specified at a faster fluid rate.

Example 17

The electrosurgical device of one or more of Examples 3-16, wherein the control system is configured to: detect an impedance spike based on a drastic change in impedance from the impedance sensor; and in response, increase the rate of fluid flowing out of the fluid port.

Example 18

A method of a control system of an electrosurgical device, the method comprising: accessing data from one or more sensors related to a physical characteristic of a function occurring at an end effector of the electrosurgical device; controlling a rate of fluid flowing to a fluid port of the electrosurgical device, based on the data related to the physical characteristic; and controlling a rate of suction flowing from a suction port of the electrosurgical device, based on the data related to the physical characteristic.

Example 19

The method of Example 18, wherein the physical characteristic comprises a measure of impedance experienced at an electrode of the end effector of the electrosurgical device.

Example 20

The method of one or more of Examples 18-19, wherein the physical characteristic comprises a measure of RF current applied to an electrode of the end effector of the electrosurgical device.

Example 21

The method of one or more of Examples 18-20, wherein the physical characteristic comprises a temperature of fluid measured at the suction port at the end effector of the electrosurgical device.

What is claimed is:

1. An electrosurgical device comprising:
   a housing;
   a shaft extending distally from the housing;
   an end effector coupled to a distal end of the shaft, the end effector comprising:
      a first electrode and a second electrode;
      a diverter comprising a planar top surface, a planar bottom surface in opposition to the planar top surface, a first terminal lateral side in mechanical communication with an inner side of an exposed longitudinal extent of the first electrode and a second terminal lateral side in mechanical communication with an inner side of an exposed longitudinal extent of the second electrode;
      a suction port, wherein the suction port is maintained at a location beneath the planar top surface of the diverter;
      a fluid port disposed above the planar top surface of the diverter; and
      a control system communicatively coupled to the suction port and the fluid port and configured to control a fluid flow rate of a fluid flowing out of the fluid port and a rate of suction of a fluid flowing into the suction port.

2. The electrosurgical device of claim 1, further comprising:
   a first fluid path in fluid communication with the fluid port; and
   a second fluid path in fluid communication with the suction port;
   wherein the housing is configured to enclose a first portion of the first fluid path and a first portion of the second fluid path; and
   wherein the shaft is configured to enclose a second portion of the first fluid path and a second portion of the second fluid path.

3. The electrosurgical device of claim 1, further comprising an impedance sensor configured to measure an impedance value at the first electrode or the second electrode.

4. The electrosurgical device of claim 3, wherein the control system is configured to control the fluid flow rate of the fluid flowing out of the fluid port based on the measured impedance value.

5. The electrosurgical device of claim 4, wherein the control system is further configured to control the rate of suction of the fluid flowing into the suction port based on the measured impedance value.

6. The electrosurgical device of claim 3, wherein the control system is configured to:
   detect an impedance spike based on a drastic change in impedance from the impedance sensor; and
   in response, increase the fluid flow rate of the fluid flowing out of the fluid port.

7. The electrosurgical device of claim 1, further comprising a radio frequency (RF) current sensor configured to measure RF current applied to the first electrode or the second electrode.

8. The electrosurgical device of claim 7, wherein the control system is configured to control the fluid flow rate of the fluid flowing out of the fluid port based on the measured RF current.

9. The electrosurgical device of claim 8, wherein the control system is further configured to control the rate of suction of the fluid flowing into the suction port based on the measured RF current.

10. The electrosurgical device of claim 1, further comprising a temperature sensor configured to measure temperature of the fluid suctioned into the suction port.

11. The electrosurgical device of claim 10, wherein the control system is configured to control the fluid flow rate of the fluid flowing out of the fluid port based on the measured temperature of the fluid suctioned into the suction port.

12. The electrosurgical device of claim 11, wherein the control system is further configured to control the rate of suction of the fluid flowing into the suction port based on the measured temperature of the fluid suctioned into the suction port.

13. The electrosurgical device of claim 1, wherein the end effector further comprises a partially deflectable member that is configured to increase the fluid flow rate of the fluid flowing out of the fluid port as the partially deflectable member increases in deflection.

14. The electrosurgical device of claim 1, wherein the control system is further configured to increase the fluid flow rate of the fluid flowing out of the fluid port the longer the first electrode and the second electrode apply energy.

15. The electrosurgical device of claim 1, wherein the control system is further configured to decrease the fluid flow rate of the fluid flowing out of the fluid port the longer the first electrode and the second electrode apply energy.

16. The electrosurgical device of claim 1, further comprising a user interface console communicatively coupled to the control system and configured to receive an input from a user to manually control an initial value of the fluid flow rate of the fluid flowing out of the fluid port.

17. The electrosurgical device of claim 16, wherein the control system is further configured to automatically increase the fluid flow rate of the fluid flowing out of the fluid port after the initial value of the fluid flow rate is manually specified from the user interface console; wherein the automatic increase of the fluid flow rate occurs based on an earlier rise in measured temperature of the fluid flowing into the suction port if the initial value of the fluid flow rate is manually specified at a slower fluid rate, and the automatic increase of the fluid flow rate occurs based on a later rise in measured temperature of the fluid flowing into the suction port if the initial value of the fluid flow rate is manually specified at a faster fluid rate.

\* \* \* \* \*